(12) United States Patent
Liu et al.

(10) Patent No.: US 7,115,767 B2
(45) Date of Patent: Oct. 3, 2006

(54) TETRALINE DERIVATIVES AS GHRELIN RECEPTOR MODULATORS

(75) Inventors: Bo Liu, Waukegan, IL (US); Gang Liu, Gurnee, IL (US); Lissa T. J. Nelson, Highland Park, IL (US); Jyoti R. Patel, Libertyville, IL (US); Hing L. Sham, Vernon Hills, IL (US); Zhili Xin, Lake Bluff, IL (US); Hongyu Zhao, Buffalo Grove, IL (US)

(73) Assignee: Abbott Laboratories, Abbott Park, IL (US)

( * ) Notice: Subject to any disclaimer, the term of this patent is extended or adjusted under 35 U.S.C. 154(b) by 0 days.

(21) Appl. No.: 10/893,484

(22) Filed: Jul. 16, 2004

(65) Prior Publication Data
US 2005/0014794 A1    Jan. 20, 2005

Related U.S. Application Data

(60) Provisional application No. 60/488,250, filed on Jul. 18, 2003.

(51) Int. Cl.
C07C 271/06 (2006.01)
A61K 31/27 (2006.01)
C07D 211/06 (2006.01)
A61K 31/401 (2006.01)

(52) U.S. Cl. .................. 560/27; 514/480; 514/534; 514/535; 514/577; 514/616; 514/617; 564/155; 564/180; 562/511; 560/43; 560/128

(58) Field of Classification Search ............... 514/534, 514/535, 617, 480, 577, 616; 564/180, 155; 560/43, 27, 128; 562/511
See application file for complete search history.

(56) References Cited

U.S. PATENT DOCUMENTS

| 5,238,955 A | * | 8/1993 | Brunner et al. ........... 514/492 |
| 5,362,878 A | * | 11/1994 | Chang et al. ............. 546/296 |
| 5,436,261 A | * | 7/1995 | Cordi et al. .............. 514/393 |
| 5,656,634 A | * | 8/1997 | Chang et al. ............. 514/256 |

FOREIGN PATENT DOCUMENTS

| GB | 2001956 | * | 2/1979 |
| JP | 56-57754 | * | 5/1981 |

OTHER PUBLICATIONS

Abbady et al, J. Chem., U.A.R., 8, No. 1, 33-39(1965).*
RN 5060-85-5, 1965.*
Asakawa, A., et al., "Ghrelin Is an Appetite-Stimulatory Signal From Stomach With Structural Resemblance to Motilin", *Gastroenterology*, 120:337-345 (2001).
Cummings, D.E., et al., "Plasma Ghrelin Levels after Diet-Induced Weight Loss or Gastric Bypass Surgery", *The New England Journ. Of Med.*, 346(21):1623-1630 (2002).

Frohman, L. A., & Jansson, J-O., "Growth Hormone-Releasing Hormone", *Endocrine Reviews*, 7(3):223-253 (1986).
Howard, A.D., et al., "A Receptorin Pituitary and Hypothalamus That Functions inGrowth Hormone Release", *Science*, 273:974-977 (1996).
Kamegai, J., et al., "Central Effect of Ghrelin, an Endogenous Growth Hormone Secretagogue, on Hypothalamic Peptide Gene Expression", *Endocrinology*, 141(12):4797-4800 (2000).
Kojima, M., et al., "Ghrelin is a growth-hormone-releasing acylated peptide from stomach", *Nature*, 402:656-660 (1999).
Momany, F.A., et al., "Design, Synthesis, and Biological Activity of Peptides which Release Growth Hormone *in Vitro*", *Endocrinology*, 108(1):31-39 (1981).
Murakami, N., et al., "Role for central ghrelin in food intake and secretion profile of stomach ghrelin in rats", *Journ of Endociniology*, 174:283-288 (2002).
Nakazato, M., et al., "A role for ghrelin in the central regulation of feeding", *Nature*, 409:194-198 (2001).
Shintani, M., et al., "Ghrelin, an Endogenous Growth Hormone Secretagogue, Is a Novel Orexigenic Peptide That Antagonizes Leptin Action Through the Activation of Hypothalamic Neuropeptide Y/Y1 Receptor Pathway", *Diabetes*, 50(2):227-232 (2001).
Shuto, Y., et al., "Hypothalamic growth hormone secretagogue receptor regulates ggrowth hormone secretion, feeding, and adiposity", *The Journ of Clin Invest.*, 109(11):1429-1436 (2002).
Svensson, J., et al., "Two-Month Treatment of Obese Subjects with the Oral Growth Hormone (GH) Secretagogue MK-677 Increases GH Secretion, Fat-Free Mass, and Energy Expenditure", *Journ of Clin Endocrin.*, 83(2):362-369 (1998).

* cited by examiner

*Primary Examiner*—Shailendra Kumar
(74) *Attorney, Agent, or Firm*—Andrew M. Parial; Johanna M. Corbin

(57) ABSTRACT

The present invention is related to compounds of formula (I),

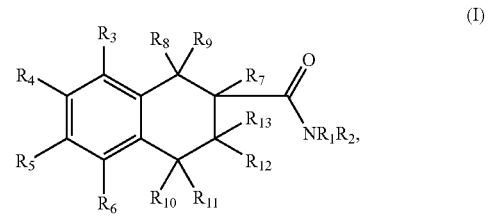

or a therapeutically suitable salt or prodrug thereof, the preparation of the compounds, compositions containing the compounds and the use of the compounds in the prevention or treatment of disorders regulated by ghrelin including anorexia, cancer cachexia, eating disorders, age-related decline in body composition, weight gain, obesity, and diabetes mellitus.

21 Claims, No Drawings

TETRALINE DERIVATIVES AS GHRELIN RECEPTOR MODULATORS

This applications claims priority from U.S. Provisional Patent Application Ser. No. 60/488,250, filed Jul. 18, 2003.

TECHNICAL FIELD

The present invention is directed to compounds that are modulators of the ghrelin receptor, the preparation of the compounds, compositions containing the compounds and the use of the compounds in the prevention or treatment of disorders regulated by ghrelin including anorexia, cancer cachexia, eating disorders, age-related decline in body composition, weight gain, obesity, and diabetes mellitus.

BACKGROUND OF THE INVENTION

Stimulation of food intake is important in connection with patients suffering from anorexia due to chronic medical conditions, eating disorders, and other conditions in which excessive weight loss has produced a detrimental effect on the patients' health.

Obesity is a common and very serious public health problem as it increases a person's risk for a number of serious conditions, including diabetes, heart disease, stroke, high blood pressure, and some types of cancers. Considerable increase in the number of obese individuals over the past two decades has created profound public health implications. Although studies have demonstrated that reduction in obesity by diet and exercise reduces the associated risk factors dramatically, these treatments are largely unsuccessful considering obesity is strongly associated with genetically inherited factors that contribute to increased appetite, preferences for highly caloric foods, reduced physical activity, and increased lipogenic metabolism.

Growth hormone (GH) is not only of importance for linear body growth but is also of major importance for the maintenance of body composition, metabolism and heart function in adult life. GH release from the anterior pituitary is regulated by the stimulatory peptide GH-releasing hormone (GHRH) and the inhibitory peptide somatostatin (Frohman, L; Jansson, J.-O. Endocr. Rev. (1986) 7:223–253). Early research identified small GH-releasing peptides (GH-RPs) derived from the pentapeptide met-enkephalin (Momany, F; Browers, C, et al: Endocrinology (1981) 108:31–39). Further efforts led to the development of a number of peptidyl and non-peptidyl growth hormone secrectgogues (GHSs), including the orally-active, non-peptidyl GH secretagogue MK677 (Svensson, J; Lohn, L; Jansson, J.-O. et al: J. Clin. Endocrinol. Metab. (1998) 83:362–369). Later efforts cloned a seven-transmembrane GPCR that was a target for the GHSs (Howard, A; Feighner, S.; Cully, D. et al: Science (1996) 273:974–977).

This GHS-receptor (GHS-R) is localized in the hypothalamus and in the pituitary, but also in other brain areas such as the hippocampus as well as the pancreas. Recently, an endogenous ligand for the GHS-R, ghrelin, an acylated peptide consisting of 28 amino acids was isolated (Kojima, M; Hosoda, H; Date, Y; Nakazoto, M.; Matsuo, H; Kangawa, K: Nature (1999), 402:656–660). Since then, ghrelin has been found to be localized in the hypothalamic-pituitary area where it stimulates the release of GH to the circulation, but is also found in the highest concentration in the stomach.

Biological evidence indicates that ghrelin has an important role in the regulation of metabolism and energy expenditure. Ghrelin was found to stimulate food intake and weight gain when administered either systemically or intraventricularly in rodents (Nakazato M, Murakami N, Date Y, Kojima M, Matsuo H, Kangawa K, et al. Nature 2001;409:194–198) (Asakawa A, Inui A, Kaga T, Yuzuriha H, Nagata T, Ueno N, et al. Gastroenterology 2001;120:337–345). Ghrelin was also found to be more potent than any other orexigenic peptide except neuropeptide Y (NPY). The orexigenic activity of centrally administered ghrelin is thought to be mediated by brain NPY and AGRP, two neuropeptides with potent orexigenic actions (Kamegai J, Tamura H, Shimizu T, Ishii S, Sugihara H, Wakabayashi I. Endocrinology 2000;141:4797–4800). It was also recognized that the appetite activity of centrally administered ghrelin can be blocked by co administration of a NPY-Y1 receptor antagonist. In addition, ghrelin was found to reverse leptin-induced inhibition of food intake (Shintani M, Ogawa Y, Ebihara K, Aizawa-Abe M, Miyanaga F, Takaya K, et al. Diabetes 2001;50:227–232). Ghrelin exerts its actions in the arcuate nucleus and paraventricular nucleus to influence the interplay of NPY, AGRP and a-MSH circuits. Ghrelin may also act via afferent vagal pathways that terminate in the hypothalamus. In obese patients, the increase in the plasma ghrelin level with diet-induced weight loss is consistent with the hypothesis that ghrelin has a role in the long-term regulation of body weight. Gastric bypass in obese patients is associated with markedly suppressed ghrelin levels, possibly contributing to the weight-reducing effect of the procedure (Cummings, D. E. et al: N Engl J Med 2002;346:1623–30).

Intracerebroventricular treatment with the anti-ghrelin antiserum against the N-terminal region twice a day for 5 days in rats decreased significantly both daily food intake and body weight (Murakami, N; T Hayashida, T; T Kuroiwa, T; K Nakahara, K; Ida, T; Mondal, M S; Nakazato, M; Kojima M; Kangawa, K. Journal of Endocrinology (2002) 174, 283–288). Transgenic (Tg) rats expressing an antisense ghrelin receptor mRNA under the control of the promoter for tyrosine hydroxylase (TH) selectively attenuated ghrelin receptor protein expression in the arcuate nucleus (Arc). Tg rats had lower body weight and less adipose tissue than did control rats. Daily food intake was reduced, and the stimulatory effect of GHS treatment on feeding was abolished in Tg rats (Shuto, Y; Shibasaki, T; Otagiri, A; et al: J. Clin. Invest. 109:1429–1436 (2002)). These data suggest that ghrelin receptor modulators may be beneficial in the treatment of anorexia, cancer cachexia, eating disorders, age-related decline in body composition, weight gain, obesity and disorders associated with obesity such as diabetes mellitus.

SUMMARY OF THE INVENTION

The present invention is directed to compounds of formula (I),

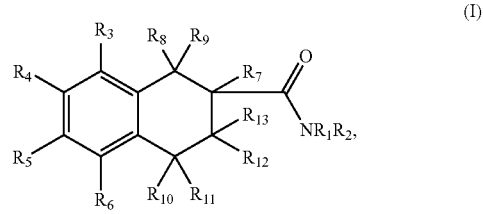

or a therapeutically suitable salt or prodrug thereof, wherein $R_1$ and $R_2$ are each independently a member selected from the group consisting of hydrogen, alkyl, aryl, arylalkyl, cycloalkyl, cycloalkylalkyl, cycloalkenyl, cycloalkenylalkyl, heterocycle, heterocyclealkyl; or $R_1$ and $R_2$ taken together with the nitrogen atom to which they are attached, together form a heterocycle;

$R_3$, $R_4$, $R_5$, and $R_6$ are each independently a member selected from the group consisting of hydrogen, alkoxy, alkoxyalkyl, alkyl, alkenyl, alkenylalkoxy, aryl, cyano, cycloalkyl, halo, haloalkyl, heterocycle, hydroxy, hydroxyalkyl, nitro, sulfonyl, $R_aR_bN—$, $R_aR_b$Nalkyl, $R_aR_b$Ncarboxyalkyl, $R_aR_b$Ncarboxyalkenyl and $R_aR_b$Nsulfonyl;

$R_7$ is a member selected from the group consisting of hydrogen, alkenyl, alkyl, alkoxy, alkoxycarbonyl, aryl, hydroxy, haloalkyl, cycloalkyl, heterocycle, $R_cR_dN—$, $R_cR_d$Ncarboxy and $R_cR_d$Nsulfonyl;

$R_8$, $R_9$, $R_{10}$, $R_{11}$, $R_{12}$ and $R_{13}$ are each independently a member selected from the group consisting of hydrogen, alkoxy, alkoxyalkyl, alkyl, alkenyl, alkenylalkoxy, aryl, cyano, halo, haloalkyl, heterocycle, hydroxy, hydroxyalkyl, $R_aR_bN—$, $R_aR_b$Nalkyl, $R_aR_b$Ncarboxyalkyl;

$R_a$ and $R_b$ are each independently a member selected from the group consisting of hydrogen, alkenyloxycarbonyl, alkoxyalkyl, alkyl, alkylcarbonyl, alkoxycarbonyl, alkoxycarbonylalkylalkoxyalkoxycarbonyl, alkylsulfonyl, alkynyloxycarbonyl, aryl, arylalkyl, arylalkoxycarbonyl, aryloxyalkyl, aryloxyalkylcarbonyl, cycloalkyl, cycloalkoxycarbonyl, cycloalkylalkyl, cycloalkylalkoxycarbonyl, heterocycle, heterocyclecarbonyl, heterocyclealkyl, heterocyclealkoxylcarbonyl, hydroxyalkoxycarbonyl, haloalkoxycarbonyl, $R_cR_d$Ncarbonyl, $R_cR_d$Ncarbonylalkyl, $R_cR_d$Nalkyl, $R_cR_d$Nalkoxycarbonyl;

$R_c$ and $R_d$ are each independently a member selected from the group consisting of hydrogen, alkenyloxycarbonyl, alkoxyalkyl, alkyl, alkylcarbonyl, alkylNHalkylcarbonyl, alkoxycarbonyl, alkoxycarbonylalkyl, alkoxyalkoxycarbonyl, alkylsulfonyl, alkynyloxycarbonyl, aryl, arylalkyl, arylalkoxycarbonyl, aryloxyalkyl, aryloxyalkylcarbonyl, cycloalkyl, cycloalkoxycarbonyl, cycloalkylalkyl, cycloalkylalkoxycarbonyl, heterocycle, heterocyclecarbonyl, heterocyclealkyl, heterocyclealkoxylcarbonyl, hydroxyalkoxycarbonyl, haloalkoxycarbonyl, nitroalkoxycarbonyl, $R_eR_f$Ncarbonyl, $R_eR_f$Ncarbonylalkyl, $R_eR_f$Nalkyl, $R_eR_f$Nalkoxycarbonyl;

$R_e$ and $R_f$ are each independently a member selected from the group consisting of hydrogen, alkyl.

According to one embodiment of the present invention there is provided a method of treating disorders regulated by ghrelin including obesity, eating disorders, weight gain and diabetes mellitus comprising administration of a thereaputically effective amount of a compounds of formula (I).

According to still another embodiment, the present invention is directed to a pharmaceutical composition comprising a therapeutically effective amount of a compound of formula (I) in combination with a pharmaceutically suitable carrier.

DETAILED DESCRIPTION OF THE INVENTION

Definitions

As used throughout this specification and the appended claims, the following terms have the following meanings:

The term "alkenyl," as used herein, refers to a straight or branched chain hydrocarbon containing from 2 to 10 carbons and containing at least one carbon-carbon double bond formed by the removal of two hydrogens. Representative examples of alkenyl include, but are not limited to, ethenyl, 2-propenyl, 2-methyl-2-propenyl, 3-butenyl, 4-pentenyl, 5-hexenyl, 2-heptenyl, 2-methyl-1-heptenyl, and 3-decenyl.

The term "alkenylalkoxy," as used herein, referes to an alkenyl group, as defined herein, appended to the parent molecular moeith through an alkoxy group, as defined herein.

The term "alkenyloxy," as used herein, referes to an alkenyl group, as defined herein, appended to the parent molecular moeith through an oxy group, as defined herein.

The term "alkenyloxycarbonyl," as used herein, referes to an alkenyloxy group, as defined herein, appended to the parent molecular moeith through an carbonyl group, as defined herein.

The term "alkoxy," as used herein, refers to an alkyl group, as defined herein, appended to the parent molecular moiety through an oxygen atom. Representative examples of alkoxy include, but are not limited to, methoxy, ethoxy, propoxy, 2-propoxy, butoxy, tert-butoxy, pentyloxy, and hexyloxy.

The term "alkoxyalkoxy," as used herein, refers to an alkoxy group, as defined herein, appended to the parent molecular moiety through an alkoxy group.

The term "alkoxyalkoxycarbonyl," as used herein, refers to an alkoxyalkoxy group, as defined herein, appended to the parent molecular moiety through a carbonyl group.

The term "alkoxyalkyl," as used herein, refers to an alkoxy group, as defined herein, appended to the parent molecular moiety through an alkyl group, as defined herein. Representative examples of alkoxyalkyl include, but are not limited to, tert-butoxymethyl, 2-ethoxyethyl, 2-methoxyethyl, and methoxymethyl.

The term "alkoxycarbonyl," as used herein, refers to an alkoxy group, as defined herein, appended to the parent molecular moiety through a carbonyl group, as defined herein. Representative examples of alkoxycarbonyl include, but are not limited to, methoxycarbonyl, ethoxycarbonyl, and tert-butoxycarbonyl.

The term "alkoxycarbonylalkyl," as used herein, refers to an alkoxycarbonyl group, as defined herein, appended to the parent molecular moiety through a alkyl group, as defined herein.

The term "alkyl," as used herein, refers to a straight or branched chain hydrocarbon containing from 1 to 10 carbon atoms. Representative examples of alkyl include, but are not limited to, methyl, ethyl, n-propyl, iso-propyl, n-butyl, sec-butyl, iso-butyl, tert-butyl, n-pentyl, isopentyl, neopentyl, n-hexyl, 3-methylhexyl, 2,2-dimethylpentyl, 2,3-dimethylpentyl, n-heptyl, n-octyl, n-nonyl, and n-decyl.

The term "alkylcarbonyl," as used herein, refers to an alkyl group, as defined herein, appended to the parent molecular moiety through a carbonyl group, as defined herein. Representative examples of alkylcarbonyl include, but are not limited to, acetyl, 1-oxopropyl, 2,2-dimethyl-1-oxopropyl, 1-oxobutyl, and 1-oxopentyl.

The term "alkylsulfonyl," as used herein, refers to an alkyl group, as defined herein, appended to the parent molecular moiety through a sulfonyl group, as defined herein. Representative examples of alkylsulfonyl include, but are not limited to, methylsulfonyl and ethylsulfonyl.

The term "alkynyl," as used herein, refers to a straight or branched chain hydrocarbon group containing from 2 to 10 carbon atoms and containing at least one carbon-carbon triple bond. Representative examples of alkynyl include, but are not limited, to acetylenyl, 1-propynyl, 2-propynyl, 3-butynyl, 2-pentynyl, and 1-butynyl.

The term "alkynyloxy," as used herein, refers to an alkynyl group appended to the parent molecular moiety through an oxy group.

The term "alkynyloxycarbonyl," as used herein, refers to an alkynyloxy group appended to the parent molecular moiety through a carbonyl group.

The term "aryl," as used herein, refers to a monocyclic-ring system, or a bicyclic- or a tricyclic-fused ring system wherein one or more of the fused rings are aromatic. Representative examples of aryl include, but are not limited to, anthracenyl, azulenyl, fluorenyl, indanyl, indenyl, naphthyl, phenyl, and tetrahydronaphthyl.

The aryl groups of this invention can be substituted with 0, 1, 2, or 3 substituents independently a member selected from alkenyl, alkoxy, alkoxyalkyl, alkoxyalkylNHalkyl, alkoxycarbonyl, alkoxycarbonylalkyl, alkyl, alkylNHalkyl, alkylcarbonyl, alkylcarbonylalkyl, alkylcarbonyloxy, alkylsulfonyl, alkylthio, alkynyl, arylalkylNHalkyl, aryloxyalkylNHalkyl, carboxy, carboxyalkyl, cyano, cyanoalkyl, cycloalkoxyalkylNHalkyl, cycloalkylNHalkyl, cycloalkenylalkylNHalkyl, formyl, halogen, haloalkyl, heterocycle, heterocyclealkyl, heterocyclealkylNHcarbonyl, heterocyclecarbonyl, haloalkyl, hydroxy, hydroxyalkyl, mercapto, nitro, phenyl, $R_gR_jN$— and $R_gR_jN$alkyl- wherein $R_g$ and $R_j$ are each independently a member selected from the group consisting of hydrogen, alkyl, alkylcarbonyl, alkylsulfonyl, aryl, arylalkyl, cycloalkyl, cycloalkylalkyl, heterocyclealkyl.

The term "arylalkoxy," as used herein, refers to an aryl group, as defined herein, appended to the parent molecular moiety through an alkoxy group, as defined herein. Representative examples of arylalkoxy include, but are not limited to, 2-phenylethoxy, 3-naphth-2-ylpropoxy, and 5-phenylpentyloxy.

The term "arylalkoxycarbonyl," as used herein, refers to an arylalkoxy group, as defined herein, appended to the parent molecular moiety through a carbonyl group, as defined herein.

The term "arylalkyl," as used herein, refers to an aryl group, as defined herein, appended to the parent molecular moiety through an alkyl group, as defined herein. Representative examples of arylalkyl include, but are not limited to, benzyl, 2-phenylethyl, 3-phenylpropyl, and 2-naphth-2-ylethyl.

The term "aryloxy," as used herein, refers to an aryl group, as defined herein, appended to the parent molecular moiety through an oxy group, as defined herein.

The term "aryloxyalkyl," as used herein, refers to an aryloxy group, as defined herein, appended to the parent molecular moiety through an alkyl group, as defined herein.

The term "aryloxyalkylcarbonyl," as used herein, refers to an aryloxyalkyl group, as defined herein, appended to the parent molecular moiety through a carbonyl group, as defined herein.

The term "arylcarbonyl," as used herein, refers to an aryl group, as defined herein, appended to the parent molecular moiety through a carbonyl group, as defined herein. Representative examples of arylcarbonyl include, but are not limited to, benzoyl and naphthoyl.

The term "carbonyl," as used herein, refers to a —C(O)— group.

The term "carboxy," as used herein, refers to a —CO$_2$H group.

The term "carboxyalkyl," as used herein, refers to a carboxy group, as defined herein, appended to the parent molecular moiety through an alkyl group, as defined herein.

Representative examples of carboxyalkyl include, but are not limited to, carboxymethyl, 2-carboxyethyl, and 3-carboxypropyl.

The term "cyano," as used herein, refers to a —CN group.

The term "cyanoalkyl," as used herein, refers to a cyano group, as defined herein, appended to the parent molecular moiety through an alkyl group, as defined herein. Representative examples of cyanoalkyl include, but are not limited to, cyanomethyl, 2-cyanoethyl, and 3-cyanopropyl.

The term "cycloalkyl," as used herein, refers to a monocyclic, bicyclic, or tricyclic ring system. Monocyclic ring systems are exemplified by a saturated cyclic hydrocarbon group containing from 3 to 8 carbon atoms. Examples of monocyclic ring systems include cyclopropyl, cyclobutyl, cyclopentyl, cyclohexyl, cycloheptyl, and cyclooctyl. Bicyclic ring systems are exemplified by a bridged monocyclic ring system in which two non-adjacent carbon atoms of the monocyclic ring are linked by an alkylene bridge of between one and three additional carbon atoms. Representative examples of bicyclic ring systems include, but are not limited to, bicyclo(3.1.1)heptane, bicyclo(2.2.1)heptane, bicyclo(2.2.2)octane, bicyclo(3.2.2)nonane, bicyclo(3.3.1)nonane, and bicyclo(4.2.1)nonane. Tricyclic ring systems are exemplified by a bicyclic ring system in which two non-adjacent carbon atoms of the bicyclic ring are linked by a bond or an alkylene bridge of between one and three carbon atoms. Representative examples of tricyclic-ring systems include, but are not limited to, tricyclo(3.3.1.0$^{3,7}$) nonane and tricyclo(3.3.1.1$^{3,7}$)decane (adamantane).

The cycloalkyl groups of this invention can be substituted with 0, 1, 2, or 3 substituents independently a member selected from alkenyl, alkoxy, alkoxyalkyl, alkoxyalkylNHalkyl, alkoxycarbonyl, alkoxycarbonylalkyl, alkyl, alkylNHalkyl, alkylcarbonyl, alkylcarbonylalkyl, alkylcarbonyloxy, alkylsulfonyl, alkylthio, alkynyl, arylalkylNHalkyl, aryloxyalkylNHalkyl, carboxy, carboxyalkyl, cyano, cyanoalkyl, cycloalkoxyalkylNHalkyl, cycloalkylNHalkyl, cycloalkenylalkylNHalkyl, formyl, halogen, haloalkyl, heterocycle, heterocyclealkyl, heterocyclealkylNHcarbonyl, heterocyclecarbonyl, hydroxy, hydroxyalkyl, mercapto, nitro, phenyl, $R_gR_jN$— and $R_gR_jN$alkyl- wherein $R_g$ and $R_j$ are defined herein.

The term "cycloalkylalkyl," as used herein, refers to a cycloalkyl group as defined herein appended to the parent molecular moiety through an alkyl group as defined herein.

The term "cycloalkylalkoxy," as used herein, refers to a cycloalkyl group as defined herein appended to the parent molecular moiety through an alkoxy group as defined herein.

The term "cycloalkylalkoxycarbonyl," as used herein, refers to a cycloalkylalkoxy group as defined herein appended to the parent molecular moiety through an carbonyl group as defined herein.

The term "cycloalkoxy," as used herein, refers to a cycloalkyl group as defined herein appended to the parent molecular moiety through an oxy group as defined herein.

The term "cycloalkoxycarbonyl," as used herein, refers to a cycloalkoxy group as defined herein appended to the parent molecular moiety through a carbonyl group as defined herein.

The term "cycloalkenyl," as used herein, refers to a monocyclic, bicyclic, or tricyclic ring system which contains 1 or 2 double bonds by is not aromatic. Monocyclic ring systems are exemplified by an unsaturated cyclic hydrocarbon group containing from 3 to 8 carbon atoms. Examples of monocyclic ring systems include cyclopropenyl, cyclobutenyl, cyclopentenyl, cyclohexenyl, cycloheptenyl, and cyclooctenyl. Bicyclic ring systems are exemplified by a bridged monocyclic ring system in which two non-adjacent carbon atoms of the monocyclic ring are linked by an alkylene bridge of between one and three additional carbon atoms.

The cycloalkenyl groups of this invention can be substituted with 0, 1, 2, or 3 substituents independently a member selected from alkenyl, alkoxy, alkoxyalkyl, alkoxyalkylNHalkyl, alkoxycarbonyl, alkoxycarbonylalkyl, alkyl, alkylNHalkyl, alkylcarbonyl, alkylcarbonylalkyl, alkylcarbonyloxy, alkylsulfonyl, alkylthio, alkynyl, arylalkylNHalkyl, aryloxyalkylNHalkyl, carboxy, carboxyalkyl, cyano, cyanoalkyl, cycloalkoxyalkylNHalkyl, cycloalkylNHalkyl, cycloalkenylalkylNHalkyl, formyl, halogen, haloalkyl, heterocycle, heterocyclealkyl, heterocyclealkylNHcarbonyl, heterocyclecarbonyl, hydroxy, hydroxyalkyl, mercapto, nitro, phenyl and $R_gR_jN$— wherein $R_g$ and $R_j$ are defined herein.

The term "cycloalkenylalkyl," as used herein, refers to a cycloalkenyl group as defined herein appended to the parent molecular moiety through an alkyl group, as defined herein.

The term "formyl," as used herein, refers to a —C(O)H group.

The term "halo" or "halogen," as used herein, refers to —Cl, —Br, —I or —F.

The term "haloalkyl," as used herein, refers to at least one halogen, as defined herein, appended to the parent molecular moiety through an alkyl group, as defined herein. Representative examples of haloalkyl include, but are not limited to, chloromethyl, 2-fluoroethyl, trifluoromethyl, pentafluoroethyl, and 2-chloro-3-fluoropentyl.

The term "haloalkoxy," as used herein, refers to at least one halogen, as defined herein, appended to the parent molecular moiety through an alkoxy group, as defined herein.

The term "haloalkoxycarbonyl," as used herein, refers to a haloalkoxy, as defined herein, appended to the parent molecular moiety through a carbonyl group, as defined herein.

The term "heterocycle" or "heterocyclic," as used herein, refers to a monocyclic, bicyclic, or tricyclic ring system. Monocyclic ring systems are exemplified by any 3- or 4-membered ring containing a heteroatom independently a member selected from oxygen, nitrogen and sulfur; or a 5-, 6- or 7-membered ring containing one, two or three heteroatoms wherein the heteroatoms are independently a member selected from nitrogen, oxygen and sulfur. The 5-membered ring has from 0–2 double bonds and the 6- and 7-membered ring have from 0–3 double bonds. Representative examples of monocyclic ring systems include, but are not limited to, azetidinyl, azepanyl, aziridinyl, diazepinyl, 1,3-dioxolanyl, dioxanyl, dithianyl, furyl, imidazolyl, imidazolinyl, imidazolidinyl, isothiazolyl, isothiazolinyl, isothiazolidinyl, isoxazolyl, isoxazolinyl, isoxazolidinyl, morpholinyl, oxadiazolyl, oxadiazolinyl, oxadiazolidinyl, oxazolyl, oxazolinyl, oxazolidinyl, piperazinyl, piperidinonyl, piperidinyl, pyranyl, pyrazinyl, pyrazolyl, pyrazolinyl, pyrazolidinyl, pyridinyl, pyrimidinyl, pyridazinyl, pyrrolyl, pyrrolinyl, pyrrolidinyl, pyrrolidinonyl, tetrahydrofuranyl, tetrahydrothienyl, tetrazinyl, tetrazolyl, thiadiazolyl, thiadiazolinyl, thiadiazolidinyl, thiazolyl, thiazolinyl, thiazolidinyl, thienyl, thiomorpholinyl, 1,1-dioxidothiomorpholinyl (thiomorpholine sulfone), thiopyranyl, triazinyl, triazolyl, and trithianyl. Bicyclic ring systems are exemplified by any of the above monocyclic ring systems fused to an aryl group as defined herein, a cycloalkyl group as defined herein, or another monocyclic ring system. Representative examples of bicyclic ring systems include but are not limited to, for example, benzimidazolyl, benzodioxinyl, benzothiazolyl, benzothienyl, benzotriazolyl, benzoxazolyl, benzofuranyl, benzopyranyl, benzothiopyranyl, cinnolinyl, indazolyl, indolyl, 2,3-dihydroindolyl, indolizinyl, methylenebenzodioxyl, naphthyridinyl, isobenzofuranyl, isobenzothienyl, isoindolyl, isoquinolinyl, phthalazinyl, 4H-pyrido(1,2-a)pyrimidin-4-one, pyranopyridinyl, quinolinyl, quinolizinyl, quinoxalinyl, quinazolinyl, tetrahydroisoquinolinyl, tetrahydroquinolinyl, and thiopyranopyridinyl. Tricyclic rings systems are exemplified by any of the above bicyclic ring systems fused to an aryl group as defined herein, a cycloalkyl group as defined herein, or a monocyclic ring system. Representative examples of tricyclic ring systems include, but are not limited to, acridinyl, carbazolyl, carbolinyl, dibenzo(b,d)furanyl, dibenzo(b,d)thienyl, naphtho (2,3-b)furan, naphtho(2,3-b)thienyl, phenazinyl, phenothiazinyl, phenoxazinyl, thianthrenyl, thioxanthenyl and xanthenyl.

According to the present invention, heterocycles of this invention can be substituted with 0, 1, 2, or 3 substituents independently a member selected from alkenyl, alkoxy, alkoxyalkyl, alkoxyalkylNHalkyl, alkoxycarbonyl, alkoxycarbonylalkyl, alkyl, alkylNHalkyl, alkylcarbonyl, alkylcarbonylalkyl, alkylcarbonyloxy, alkylsulfonyl, alkylthio, alkynyl, arylalkoxyalkyl, arylalkylNHalkyl, aryloxyalkylNHalkyl, carboxy, carboxyalkyl, cyano, cyanoalkyl, cycloalkoxyalkylNHalkyl, cycloalkylNHalkyl, cycloalkenylalkylNHalkyl, formyl, halogen, haloalkyl, heterocycle, heterocyclealkyl, heterocyclealkylNHcarbonyl, heterocyclecarbonyl, hydroxy, hydroxyalkyl, mercapto, nitro, phenyl and $R_gR_jN$—, $R_gR_jN$carbonyl, $R_gR_jN$alkyl, wherein $R_g$ and $R_j$ are defined herein.

The term "heterocyclealkyl," as used herein, refers to a heterocycle, as defined herein, appended to the parent molecular moiety through an alkyl group, as defined herein. Representative examples of heterocyclealkyl include, but are not limited to, pyridin-3-ylmethyl and 2-pyrimidin-2-ylpropyl and the like.

The term "heterocyclealkoxy," as used herein, refers to a heterocycle, as defined herein, appended to the parent molecular moiety through an alkoxy group, as defined herein.

The term "heterocyclealkoxycarbonyl," as used herein, refers to a heterocyclealkoxy, as defined herein, appended to the parent molecular moiety through a carbonyl group, as defined herein.

The term "heterocyclecarbonyl," as used herein, refers to a heterocycle, as defined herein, appended to the parent molecular moiety through a carbonyl group, as defined herein.

The term "hydroxy," as used herein, refers to an —OH group.

The term "hydroxyalkyl," as used herein, refers to at least one hydroxy group, as defined herein, appended to the parent molecular moiety through an alkyl group, as defined herein. Representative examples of hydroxyalkyl include, but are not limited to, 2-hydroxyethyl, 2-hydroxypropyl, 1,2-dihydroxypropyl, 3-hydroxybutyl and the like.

The term "hydroxyalkoxy," as used herein, refers to at least one hydroxy group, as defined herein, appended to the parent molecular moiety through an alkoxy group, as defined herein.

The term "hydroxyalkoxycarbonyl," as used herein, refers to at least one hydroxyalkoxy group, as defined herein, appended to the parent molecular moiety through a carbonyl group, as defined herein.

The term "nitro," as used herein, refers to a —NO₂ group.

The term "oxy," as used herein, refers to a —O— group.

The term "sulfonyl," as used herein, refers to a —SO₂— group.

Accordingly, the principle embodiment of the present invention is directed to compounds of formula (I),

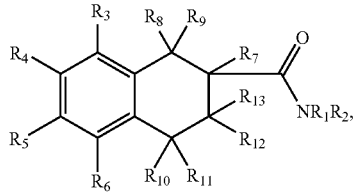
(I)

or a therapeutically suitable salt or prodrug thereof, wherein $R_1$ and $R_2$ are each independently a member selected from the group consisting of hydrogen, alkyl, aryl, arylalkyl, cycloalkyl, cycloalkylalkyl, cycloalkenyl, cycloalkenylalkyl, heterocycle, heterocyclealkyl; or $R_1$ and $R_2$ taken together with the nitrogen atom to which they are attached, together form a heterocycle; $R_3$, $R_4$, $R_5$, and $R_6$ are each independently a member selected from the group consisting of hydrogen, alkoxy, alkoxyalkyl, alkyl, alkenyl, alkenylalkoxy, aryl, cyano, cycloalkyl, halo, haloalkyl, heterocycle, hydroxy, hydroxyalkyl, nitro, sulfonyl, $R_aR_bN$—, $R_aR_b$-Nalkyl, $R_aR_b$Ncarboxyalkyl, $R_aR_b$Ncarboxyalkenyl and $R_aR_b$Nsulfonyl; $R_7$ is a member selected from the group consisting of hydrogen, alkenyl, alkyl, alkoxy, alkoxycarbonyl, aryl, hydroxy, haloalkyl, cycloalkyl, heterocycle, $R_cR_dN$—, $R_cR_d$Ncarboxy and $R_cR_d$Nsulfonyl; $R_8$, $R_9$, $R_{10}$, $R_{11}$, $R_{12}$ and $R_{13}$ are each independently a member selected from the group consisting of hydrogen, alkoxy, alkoxyalkyl, alkyl, alkenyl, alkenylalkoxy, aryl, cyano, halo, haloalkyl, heterocycle, hydroxy, hydroxyalkyl, $R_aR_bN$—, $R_aR_b$Nalkyl, $R_aR_b$Ncarboxyalkyl; $R_a$ and $R_b$ are each independently a member selected from the group consisting of hydrogen, alkenyloxycarbonyl, alkoxyalkyl, alkyl, alkylcarbonyl, alkoxycarbonyl, alkoxycarbonylalkylalkoxy-alkoxycarbonyl, alkylsulfonyl, alkynyloxycarbonyl, aryl, arylalkyl, arylalkoxycarbonyl, aryloxyalkyl, aryloxyalkylcarbonyl, cycloalkyl, cycloalkoxycarbonyl, cycloalkylalkyl, cycloalkylalkoxycarbonyl, heterocycle, heterocyclecarbonyl, heterocyclealkyl, heterocyclealkoxyl carbonyl, hydroxyalkoxycarbonyl, haloalkoxycarbonyl, $R_cR_d$Ncarbonyl, $R_cR_d$Ncarbonylalkyl, $R_cR_d$Nalkyl, $R_cR_d$Nalkoxycarbonyl; $R_c$ and $R_d$ are each independently a member selected from the group consisting of hydrogen, alkenyloxycarbonyl, alkoxyalkyl, alkyl, alkylcarbonyl, alkylNHalkylcarbonyl, alkoxycarbonyl, alkoxycarbonylalkyl, alkoxyalkoxycarbonyl, alkylsulfonyl, alkynyloxycarbonyl, aryl, arylalkyl, arylalkoxycarbonyl, aryloxyalkyl, aryloxyalkylcarbonyl, cycloalkyl, cycloalkoxycarbonyl, cycloalkylalkyl, cycloalkylalkoxycarbonyl, heterocycle, heterocyclecarbonyl, heterocyclealkyl, heterocyclealkoxyl carbonyl, hydroxyalkoxycarbonyl, haloalkoxycarbonyl, nitroalkoxycarbonyl, $R_eR_f$Ncarbonyl, $R_eR_f$Ncarbonylalkyl, $R_eR_f$Nalkyl, $R_eR_f$Nalkoxycarbonyl; and $R_e$ and $R_f$ are each independently a member selected from the group consisting of hydrogen and alkyl.

According to another embodiment, the present invention is directed to compounds of formula (Ia),

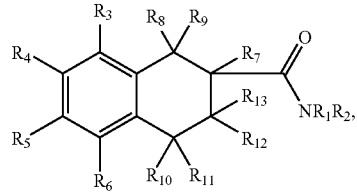
(Ia)

or a therapeutically suitable salt or prodrug thereof, wherein $R_1$ and $R_2$ are each independently a member selected from the group consisting of hydrogen, alkyl, aryl, arylalkyl, heterocycle, heterocyclealkyl; $R_3$, $R_4$, $R_5$, and $R_6$ are each independently a member selected from the group consisting of hydrogen, alkoxy, alkoxyalkyl, alkyl, alkenyl, alkenylalkoxy, aryl, cyano, cycloalkyl, halo, haloalkyl, heterocycle, hydroxy, hydroxyalkyl, nitro, sulfonyl, $R_aR_bN$—, $R_aR_b$Nalkyl, $R_aR_b$Ncarboxyalkyl, $R_aR_b$Ncarboxyalkenyl, $R_aR_b$Nsulfonyl; $R_7$ is hydrogen; $R_8$, $R_9$, $R_{10}$, $R_{11}$, $R_{12}$ and $R_{13}$ are each independently a member selected from the group consisting of hydrogen, alkoxy, alkoxyalkyl, alkyl, alkenyl, alkenylalkoxy, aryl, cyano, halo, haloalkyl, heterocycle, hydroxy, hydroxyalkyl, $R_aR_bN—$, $R_aR_bNalkyl$, $R_aR_bNcarboxyalkyl$; $R_a$ and $R_b$ are each independently a member selected from the group consisting of hydrogen, alkenyloxycarbonyl, alkoxyalkyl, alkyl, alkylcarbonyl, alkoxycarbonyl, alkoxycarbonylalkylalkoxyalkoxycarbonyl, alkylsulfonyl, alkynyloxycarbonyl, aryl, arylalkyl, arylalkoxycarbonyl, aryloxyalkyl, aryloxyalkylcarbonyl, cycloalkyl, cycloalkoxycarbonyl, cycloalkylalkyl, cycloalkylalkoxycarbonyl, heterocycle, heterocyclecarbonyl, heterocyclealkyl, heterocyclealkoxyl carbonyl, hydroxyalkoxycarbonyl, haloalkoxycarbonyl, $R_cR_dNcarbonyl$, $R_cR_dNcarbonylalkyl$, $R_cR_dNalkyl$, $R_cR_dNalkoxycarbonyl$; $R_c$ and $R_d$ are each independently a member selected from the group consisting of hydrogen, alkenyloxycarbonyl, alkoxyalkyl, alkyl, alkylcarbonyl, alkylNHalkylcarbonyl, alkoxycarbonyl, alkoxycarbonylalkyl, alkoxyalkoxycarbonyl, alkylsulfonyl, alkynyloxycarbonyl, aryl, arylalkyl, arylalkoxycarbonyl, aryloxyalkyl, aryloxyalkylcarbonyl, cycloalkyl, cycloalkoxycarbonyl, cycloalkylalkyl, cycloalkylalkoxycarbonyl, heterocycle, heterocyclecarbonyl, heterocyclealkyl, heterocyclealkoxyl carbonyl, hydroxyalkoxycarbonyl, haloalkoxycarbonyl, nitroalkoxycarbonyl, $R_eR_fNcarbonyl$, $R_eR_fNcarbonylalkyl$, $R_eR_fNalkyl$, $R_eR_fNalkoxycarbonyl$; and $R_e$ and $R_f$ are each independently a member selected from the group consisting of hydrogen and alkyl.

According to another embodiment, the present invention is directed to compounds of formula (Ia), or a therapeutically suitable salt or prodrug thereof, wherein $R_1$ and $R_2$ are each independently a member selected from the group consisting of hydrogen, alkyl, aryl, arylalkyl, heterocycle, heterocyclealkyl; $R_3$, $R_4$, $R_5$, and $R_6$ are each independently a member selected from the group consisting of hydrogen, alkoxy, alkoxyalkyl, alkyl, alkenyl, alkenylalkoxy, aryl, cyano, cycloalkyl, halo, haloalkyl, heterocycle, hydroxy, hydroxyalkyl, nitro, sulfonyl, $R_aR_bN—$, $R_aR_bNalkyl$, $R_aR_bNcarboxyalkyl$, $R_aR_bNcarboxyalkenyl$, $R_aR_bNsulfonyl$; $R_7$ is a member selected from the group consisting of alkenyl, alkyl; $R_8$, $R_9$, $R_{10}$, $R_{11}$, $R_{12}$ and $R_{13}$ are each independently a member selected from the group consisting of hydrogen, alkoxy, alkoxyalkyl, alkyl, alkenyl, alkenylalkoxy, aryl, cyano, halo, haloalkyl, heterocycle, hydroxy, hydroxyalkyl, $R_aR_bN—$, $R_aR_bNalkyl$, $R_aR_bNcarboxyalkyl$; $R_a$ and $R_b$ are each independently a member selected from the group consisting of hydrogen, alkenyloxycarbonyl, alkoxyalkyl, alkyl, alkylcarbonyl, alkoxycarbonyl, alkoxycarbonylalkylalkoxyalkoxycarbonyl, alkylsulfonyl, alkynyloxycarbonyl, aryl, arylalkyl, arylalkoxycarbonyl, aryloxyalkyl, aryloxyalkylcarbonyl, cycloalkyl, cycloalkoxycarbonyl, cycloalkylalkyl, cycloalkylalkoxycarbonyl, heterocycle, heterocyclecarbonyl, heterocyclealkyl, heterocyclealkoxyl carbonyl, hydroxyalkoxycarbonyl, haloalkoxycarbonyl, $R_cR_dNcarbonyl$, $R_cR_dNcarbonylalkyl$, $R_cR_dNalkyl$, $R_cR_dNalkoxycarbonyl$; $R_c$ and $R_d$ are each independently a member selected from the group consisting of hydrogen, alkenyloxycarbonyl, alkoxyalkyl, alkyl, alkylcarbonyl, alkylNHalkylcarbonyl, alkoxycarbonyl, alkoxycarbonylalkyl, alkoxyalkoxycarbonyl, alkylsulfonyl, alkynyloxycarbonyl, aryl, arylalkyl, arylalkoxycarbonyl, aryloxyalkyl, aryloxyalkylcarbonyl, cycloalkyl, cycloalkoxycarbonyl, cycloalkylalkyl, cycloalkylalkoxycarbonyl, heterocycle, heterocyclecarbonyl, heterocyclealkyl, heterocyclealkoxyl carbonyl, hydroxyalkoxycarbonyl, haloalkoxycarbonyl, nitroalkoxycarbonyl, $R_eR_fNcarbonyl$, $R_eR_fNcarbonylalkyl$, $R_eR_fNalkyl$, $R_eR_fNalkoxycarbonyl$; and $R_e$ and $R_f$ are each independently a member selected from the group consisting of hydrogen and alkyl.

According to another embodiment, the present invention is directed to compounds of formula (Ia), or a therapeutically suitable salt or prodrug thereof, wherein $R_1$ and $R_2$ are each independently a member selected from the group consisting of hydrogen, alkyl, aryl, arylalkyl, heterocycle, heterocyclealkyl; $R_3$, $R_4$, $R_5$, and $R_6$ are each independently a member selected from the group consisting of hydrogen, alkoxy, alkoxyalkyl, alkyl, alkenyl, alkenylalkoxy, aryl, cyano, cycloalkyl, halo, haloalkyl, heterocycle, hydroxy, hydroxyalkyl, nitro, sulfonyl, $R_aR_bN—$, $R_aR_bNalkyl$, $R_aR_bNcarboxyalkyl$, $R_aR_bNcarboxyalkenyl$, $R_aR_bNsulfonyl$; $R_7$ is a member selected from the group consisting $R_cR_dN—$, $R_cR_dNcarboxy$ and $R_cR_dNsulfonyl$; $R_8$, $R_9$, $R_{10}$, $R_{11}$, $R_{12}$ and $R_{13}$ are each independently a member selected from the group consisting of hydrogen, alkoxy, alkoxyalkyl, alkyl, alkenyl, alkenylalkoxy, aryl, cyano, halo, haloalkyl, heterocycle, hydroxy, hydroxyalkyl, $R_aR_bN—$, $R_aR_bNalkyl$, $R_aR_bNcarboxyalkyl$; $R_a$ and $R_b$ are each independently a member selected from the group consisting of hydrogen, alkenyloxycarbonyl, alkoxyalkyl, alkyl, alkylcarbonyl, alkoxycarbonyl, alkoxycarbonylalkylalkoxyalkoxycarbonyl, alkylsulfonyl, alkynyloxycarbonyl, aryl, arylalkyl, arylalkoxycarbonyl, aryloxyalkyl, aryloxyalkylcarbonyl, cycloalkyl, cycloalkoxycarbonyl, cycloalkylalkyl, cycloalkylalkoxycarbonyl, heterocycle, heterocyclecarbonyl, heterocyclealkyl, heterocyclealkoxyl carbonyl, hydroxyalkoxycarbonyl, haloalkoxycarbonyl, $R_cR_dN$carbonyl, $R_cR_dN$carbonylalkyl, $R_cR_dN$alkyl, $R_cR_dN$alkoxycarbonyl; $R_c$ and $R_d$ are each independently a member selected from the group consisting of hydrogen, alkenyloxycarbonyl, alkoxyalkyl, alkyl, alkylcarbonyl, alkylNHalkylcarbonyl, alkoxycarbonyl, alkoxycarbonylalkyl, alkoxyalkoxycarbonyl, alkylsulfonyl, alkynyloxycarbonyl, aryl, arylalkyl, arylalkoxycarbonyl, aryloxyalkyl, aryloxyalkylcarbonyl, cycloalkyl, cycloalkoxycarbonyl, cycloalkylalkyl, cycloalkylalkoxycarbonyl, heterocycle, heterocyclecarbonyl, heterocyclealkyl, heterocyclealkoxyl carbonyl, hydroxyalkoxycarbonyl, haloalkoxycarbonyl, nitroalkoxycarbonyl, $R_eR_fN$carbonyl, $R_eR_fN$carbonylalkyl, $R_eR_fN$alkyl, $R_eR_fN$alkoxycarbonyl; and $R_e$ and $R_f$ are each independently a member selected from the group consisting of hydrogen and alkyl.

According to another embodiment, the present invention is directed to compounds of formula (II),

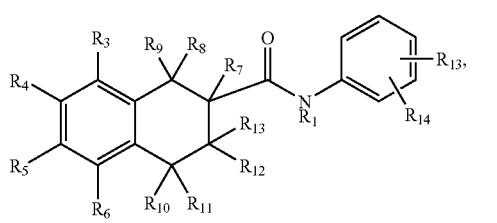

(II)

or a therapeutically suitable salt or prodrug thereof, wherein $R_3$, $R_4$, $R_5$, and $R_6$ are each independently a member selected from the group consisting of hydrogen, alkoxy, alkoxyalkyl, alkyl, alkenyl, alkenylalkoxy, aryl, cyano, cycloalkyl, halo, haloalkyl, heterocycle, hydroxy, hydroxyalkyl, nitro, sulfonyl, $R_aR_bN$—, $R_aR_bN$alkyl, $R_aR_bN$carboxyalkyl, $R_aR_bN$carboxyalkenyl, $R_aR_bN$sulfonyl; $R_7$ is a member selected from the group consisting of hydrogen, alkenyl, alkyl, alkoxy, alkoxycarbonyl, aryl, hydroxy, haloalkyl, cycloalkyl, heterocycle, $R_cR_dN$—, $R_cR_dN$carboxy and $R_cR_dN$sulfonyl; $R_8$, $R_9$, $R_{10}$, $R_{11}$, $R_{12}$ and $R_{13}$ are each independently a member selected from the group consisting of hydrogen, alkoxy, alkoxyalkyl, alkyl, alkenyl, alkenylalkoxy, aryl, cyano, halo, haloalkyl, heterocycle, hydroxy, hydroxyalkyl, $R_aR_bN$—, $R_aR_bN$alkyl, $R_aR_bN$carboxyalkyl; $R_a$ and $R_b$ are each independently a member selected from the group consisting of hydrogen, alkenyloxycarbonyl, alkoxyalkyl, alkyl, alkylcarbonyl, alkoxycarbonyl, alkoxycarbonylalkylalkoxyalkoxycarbonyl, alkylsulfonyl, alkynyloxycarbonyl, aryl, arylalkyl, arylalkoxycarbonyl, aryloxyalkyl, aryloxyalkylcarbonyl, cycloalkyl, cycloalkoxycarbonyl, cycloalkylalkyl, cycloalkylalkoxycarbonyl, heterocycle, heterocyclecarbonyl, heterocyclealkyl, heterocyclealkoxyl carbonyl, hydroxyalkoxycarbonyl, haloalkoxycarbonyl, $R_cR_dN$carbonyl, $R_cR_dN$carbonylalkyl, $R_cR_dN$alkyl, $R_cR_dN$alkoxycarbonyl; $R_c$ and $R_d$ are each independently a member selected from the group consisting of hydrogen, alkenyloxycarbonyl, alkoxyalkyl, alkyl, alkylcarbonyl, alkylNHalkylcarbonyl, alkoxycarbonyl, alkoxycarbonylalkyl, alkoxyalkoxycarbonyl, alkylsulfonyl, alkynyloxycarbonyl, aryl, arylalkyl, arylalkoxycarbonyl, aryloxyalkyl, aryloxyalkylcarbonyl, cycloalkyl, cycloalkoxycarbonyl, cycloalkylalkyl, cycloalkylalkoxycarbonyl, heterocycle, heterocyclecarbonyl, heterocyclealkyl, heterocyclealkoxyl carbonyl, hydroxyalkoxycarbonyl, haloalkoxycarbonyl, nitroalkoxycarbonyl, $R_eR_fN$carbonyl, $R_eR_fN$carbonylalkyl, $R_eR_fN$alkyl, $R_eR_fN$alkoxycarbonyl; and $R_e$ and $R_f$ are each independently a member selected from the group consisting of hydrogen and alkyl.

According to another embodiment, the present invention is directed to compounds of formula (IIa),

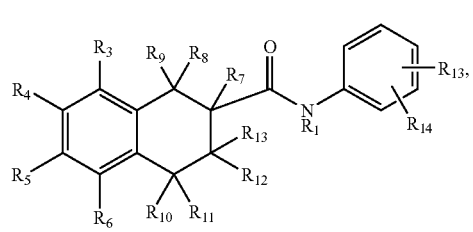

(IIa)

or a therapeutically suitable salt or prodrug thereof, wherein $R_3$, $R_4$, $R_5$, and $R_6$ are each independently a member selected from the group consisting of hydrogen, alkoxy, alkoxyalkyl, alkyl, alkenyl, alkenylalkoxy, cyano, halo, haloalkyl, hydroxy, hydroxyalkyl, nitro, sulfonyl; $R_7$ is hydrogen; $R_8$, $R_9$, $R_{10}$, $R_{11}$, $R_{12}$ and $R_{13}$ are each independently a member selected from the group consisting of hydrogen, alkoxy, alkoxyalkyl, alkyl, alkenyl, alkenylalkoxy, aryl, cyano, halo, haloalkyl, heterocycle, hydroxy, hydroxyalkyl, $R_aR_bN$—, $R_aR_bN$alkyl, $R_aR_bN$carboxyalkyl; and $R_a$ and $R_b$ are each independently a member selected from the group consisting of hydrogen, alkoxyalkyl, alkyl, alkylcarbonyl, alkoxycarbonyl, alkoxycarbonylalkyl, aryl, arylalkyl, aryloxyalkyl, cycloalkyl, cycloalkylalkyl, heterocycle, heterocyclecarbonyl, heterocyclealkyl and heterocyclealkoxyl carbonyl.

According to another embodiment, the present invention is directed to compounds of formula (IIb),

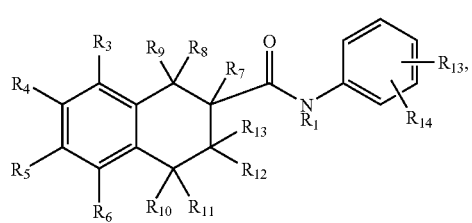

(IIb)

or a therapeutically suitable salt or prodrug thereof, wherein $R_3$, $R_4$, $R_5$, and $R_6$ are each independently a member selected from the group consisting of hydrogen, alkoxy, alkoxyalkyl, alkyl, alkenyl, alkenylalkoxy, aryl, cyano, halo, haloalkyl, heterocycle, hydroxy, hydroxyalkyl, nitro, sulfonyl, $R_aR_bN$—, $R_aR_bN$alkyl, $R_aR_bN$carboxyalkyl; $R_7$ is a member selected from the group consisting of alkenyl, alkyl, alkoxy, aryl, hydroxy, haloalkyl, cycloalkyl, heterocycle and $R_cR_dN$-; $R_8$, $R_9$, $R_{10}$, $R_{11}$, $R_{12}$ and $R_{13}$ are each independently a member selected from the group consisting of hydrogen, alkoxy, alkoxyalkyl, alkyl, alkenyl, alkenylalkoxy, aryl, cyano, halo, haloalkyl, heterocycle, hydroxy, hydroxyalkyl, $R_aR_bN$—, $R_aR_bN$alkyl, $R_aR_bN$carboxyalkyl; $R_a$ and $R_b$ are each independently a member selected from the group consisting of hydrogen, alkenyloxycarbonyl, alkoxyalkyl, alkyl, alkylcarbonyl, alkoxycarbonyl, alkoxycarbonylalkylalkoxyalkoxycarbonyl, alkylsulfonyl, alkynyloxycarbonyl, aryl, arylalkyl, arylalkoxycarbonyl, aryloxyalkyl, aryloxyalkylcarbonyl, cycloalkyl, cycloalkoxycarbonyl, cycloalkylalkyl, cycloalkylalkoxycarbonyl, heterocycle, heterocyclecarbonyl, heterocyclealkyl, heterocyclealkoxyl carbonyl, hydroxyalkoxycarbonyl, haloalkoxycarbonyl, R$_c$R$_d$Ncarbonyl, R$_c$R$_d$Ncarbonylalkyl, R$_c$R$_d$Nalkyl, R$_c$R$_d$Nalkoxycarbonyl; R$_c$ and R$_d$ are each independently a member selected from the group consisting of hydrogen, alkenyloxycarbonyl, alkoxyalkyl, alkyl, alkylcarbonyl, alkylNHalkylcarbonyl, alkoxycarbonyl, alkoxycarbonylalkyl, alkoxyalkoxycarbonyl, alkylsulfonyl, alkynyloxycarbonyl, aryl, arylalkyl, arylalkoxycarbonyl, aryloxyalkyl, aryloxyalkylcarbonyl, cycloalkyl, cycloalkoxycarbonyl, cycloalkylalkyl, cycloalkylalkoxycarbonyl, heterocycle, heterocyclecarbonyl, heterocyclealkyl, heterocyclealkoxyl carbonyl, hydroxyalkoxycarbonyl, haloalkoxycarbonyl, nitroalkoxycarbonyl, R$_e$R$_f$Ncarbonyl, R$_e$R$_f$Ncarbonylalkyl, R$_e$R$_f$Nalkyl, R$_e$R$_f$Nalkoxycarbonyl; and R$_e$ and R$_f$ are each independently a member selected from the group consisting of hydrogen and alkyl.

According to another embodiment, the present invention is directed to compounds of formula (IIb), or a therapeutically suitable salt or prodrug thereof, wherein R$_3$, R$_4$, R$_5$, and R$_6$ are each independently a member selected from the group consisting of hydrogen, alkoxy, alkoxyalkyl, alkyl, alkenyl, alkenylalkoxy, halo, haloalkyl, hydroxy and hydroxyalkyl; R$_7$ is a member selected from the group consisting of alkenyl, alkyl, alkoxy, aryl, hydroxy, haloalkyl, cycloalkyl, heterocycle and R$_e$R$_f$N-; R$_8$, R$_9$, R$_{10}$, R$_{11}$, R$_{12}$ and R$_{13}$ are each independently a member selected from the group consisting of hydrogen, alkoxy, alkoxyalkyl, alkyl, alkenyl, alkenylalkoxy, aryl, cyano, halo, haloalkyl, heterocycle, hydroxy, hydroxyalkyl, R$_a$R$_b$N—, R$_a$R$_b$Nalkyl, R$_a$R$_b$Ncarboxyalkyl; R$_a$ and R$_b$ are each independently a member of the group consisting of hydrogen, alkenyloxycarbonyl, alkoxyalkyl, alkyl, alkylcarbonyl, alkoxycarbonyl, alkoxycarbonylalkylalkoxyalkoxycarbonyl, alkylsulfonyl, alkynyloxycarbonyl, aryl, arylalkyl, arylalkoxycarbonyl, aryloxyalkyl, aryloxyalkylcarbonyl, cycloalkyl, cycloalkoxycarbonyl, cycloalkylalkyl, cycloalkylalkoxycarbonyl, heterocycle, heterocyclecarbonyl, heterocyclealkyl, heterocyclealkoxyl carbonyl, hydroxyalkoxycarbonyl, haloalkoxycarbonyl, R$_c$R$_d$Ncarbonyl, R$_c$R$_d$Ncarbonylalkyl, R$_c$R$_d$Nalkyl, R$_c$R$_d$Nalkoxycarbonyl; R$_c$ and R$_d$ are each independently a member selected from the group consisting of hydrogen, alkenyloxycarbonyl, alkoxyalkyl, alkyl, alkylcarbonyl, alkylNHalkylcarbonyl, alkoxycarbonyl, alkoxycarbonylalkyl, alkoxyalkoxycarbonyl, alkylsulfonyl, alkynyloxycarbonyl, aryl, arylalkyl, arylalkoxycarbonyl, aryloxyalkyl, aryloxyalkylcarbonyl, cycloalkyl, cycloalkoxycarbonyl, cycloalkylalkyl, cycloalkylalkoxycarbonyl, heterocycle, heterocyclecarbonyl, heterocyclealkyl, heterocyclealkoxyl carbonyl, hydroxyalkoxycarbonyl, haloalkoxycarbonyl, nitroalkoxycarbonyl, R$_e$R$_f$Ncarbonyl, R$_e$R$_f$Ncarbonylalkyl, R$_e$R$_f$Nalkyl, R$_e$R$_f$Nalkoxycarbonyl; and R$_e$ and R$_f$ are each independently a member selected from the group consisting of hydrogen and alkyl.

According to another embodiment, the present invention is directed to compounds of formula (IIc),

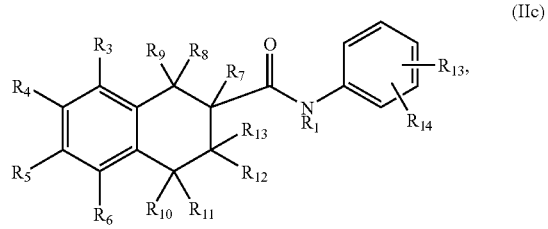

(IIc)

or a therapeutically suitable salt or prodrug thereof, wherein R$_3$, R$_4$, R$_5$, and R$_6$ are each independently a member selected from the group consisting of hydrogen, alkoxy, alkoxyalkyl, alkyl, alkenyl, alkenylalkoxy, aryl, cyano, halo, haloalkyl, heterocycle, hydroxy, hydroxyalkyl, nitro, sulfonyl, R$_a$R$_b$N—, R$_a$R$_b$Nalkyl, R$_a$R$_b$Ncarboxyalkyl; R$_7$ is a member selected from the group consisting of alkoxycarbonyl, R$_c$R$_d$Ncarboxy and R$_c$R$_d$Nsulfonyl; R$_8$, R$_9$, R$_{10}$, R$_{11}$, R$_{12}$ and R$_{13}$ are each independently a member selected from the group consisting of hydrogen, alkoxy, alkoxyalkyl, alkyl, alkenyl, alkenylalkoxy, aryl, cyano, halo, haloalkyl, heterocycle, hydroxy, hydroxyalkyl, R$_a$R$_b$N—, R$_a$R$_b$Nalkyl, R$_a$R$_b$Ncarboxyalkyl; R$_a$ and R$_b$ are each independently a member selected from the group consisting of hydrogen, alkenyloxycarbonyl, alkoxyalkyl, alkyl, alkylcarbonyl, alkoxycarbonyl, alkoxycarbonylalkylalkoxyalkoxycarbonyl, alkylsulfonyl, alkynyloxycarbonyl, aryl, arylalkyl, arylalkoxycarbonyl, aryloxyalkyl, aryloxyalkylcarbonyl, cycloalkyl, cycloalkoxycarbonyl, cycloalkylalkyl, cycloalkylalkoxycarbonyl, heterocycle, heterocyclecarbonyl, heterocyclealkyl, heterocyclealkoxyl carbonyl, hydroxyalkoxycarbonyl, haloalkoxycarbonyl, R$_c$R$_d$Ncarbonyl, R$_c$R$_d$Ncarbonylalkyl, R$_c$R$_d$Nalkyl, R$_c$R$_d$Nalkoxycarbonyl; $R_c$ and $R_d$ are each independently a member selected from the group consisting of hydrogen, alkenyloxycarbonyl, alkoxyalkyl, alkyl, alkylcarbonyl, alkylNHalkylcarbonyl, alkoxycarbonyl, alkoxycarbonylalkyl, alkoxyalkoxycarbonyl, alkylsulfonyl, alkynyloxycarbonyl, aryl, arylalkyl, arylalkoxycarbonyl, aryloxyalkyl, aryloxyalkylcarbonyl, cycloalkyl, cycloalkoxycarbonyl, cycloalkylalkyl, cycloalkylalkoxycarbonyl, heterocycle, heterocyclecarbonyl, heterocyclealkyl, heterocyclealkoxyl carbonyl, hydroxyalkoxycarbonyl, haloalkoxycarbonyl, nitroalkoxycarbonyl, $R_eR_fN$carbonyl, $R_eR_fN$carbonylalkyl, $R_eR_fN$alkyl, $R_eR_fN$alkoxycarbonyl; and $R_e$ and $R_f$ are each independently a member selected from the group consisting of hydrogen and alkyl.

According to one embodiment of the present invention there is provided a method of treating anorexia, comprising administration of a compound of formula (I). According to one embodiment of the present invention there is provided a method of treating anorexia, comprising administration of a compound of formula (Ia).

According to one embodiment of the present invention there is provided a method of treating anorexia, comprising administration of a compound of formula (II). According to one embodiment of the present invention there is provided a method of treating anorexia, comprising administration of a compound of formula (IIa). According to one embodiment of the present invention there is provided a method of treating anorexia, comprising administration of a compound of formula (IIb). According to one embodiment of the present invention there is provided a method of treating anorexia, comprising administration of a compound of formula (IIc).

According to one embodiment of the present invention there is provided a method of treating cancer cachexia, comprising administration of a compound of formula (I). According to one embodiment of the present invention there is provided a method of treating cancer cachexia, comprising administration of a compound of formula (Ia).

According to one embodiment of the present invention there is provided a method of treating cancer cachexia, comprising administration of a compound of formula (II). According to one embodiment of the present invention there is provided a method of treating cancer cachexia, comprising administration of a compound of formula (IIa). According to one embodiment of the present invention there is provided a method of treating cancer cachexia, comprising administration of a compound of formula (IIb). According to one embodiment of the present invention there is provided a method of treating cancer cachexia, comprising administration of a compound of formula (IIc).

According to one embodiment of the present invention there is provided a method of treating eating disorders, comprising administration of a compound of formula (I). According to one embodiment of the present invention there is provided a method of treating eating disorders, comprising administration of a compound of formula (Ia).

According to one embodiment of the present invention there is provided a method of treating eating disorders, comprising administration of a compound of formula (II). According to one embodiment of the present invention there is provided a method of treating eating disorders, comprising administration of a compound of formula (Ia). According to one embodiment of the present invention there is provided a method of treating eating disorders, comprising administration of a compound of formula (IIb). According to one embodiment of the present invention there is provided a method of treating eating disorders, comprising administration of a compound of formula (IIc).

According to one embodiment of the present invention there is provided a method of treating age-related decline in body composition, comprising administration of a compound of formula (I). According to one embodiment of the present invention there is provided a method of treating age-related decline in body composition, comprising administration of a compound of formula (Ia).

According to one embodiment of the present invention there is provided a method of treating age-related decline in body composition, comprising administration of a compound of formula (II). According to one embodiment of the present invention there is provided a method of treating age-related decline in body composition, comprising administration of a compound of formula (IIa). According to one embodiment of the present invention there is provided a method of treating age-related decline in body composition, comprising administration of a compound of formula (IIb). According to one embodiment of the present invention there is provided a method of treating age-related decline in body composition, comprising administration of a compound of formula (IIc).

According to one embodiment of the present invention there is provided a method of treating weight gain, comprising administration of a compound of formula (I). According to one embodiment of the present invention there is provided a method of treating weight gain, comprising administration of a compound of formula (Ia).

According to one embodiment of the present invention there is provided a method of treating weight gain, comprising administration of a compound of formula (II). According to one embodiment of the present invention there is provided a method of treating weight gain, comprising administration of a compound of formula (IIa). According to one embodiment of the present invention there is provided a method of treating weight gain, comprising administration of a compound of formula (IIb). According to one embodiment of the present invention there is provided a method of treating weight gain, comprising administration of a compound of formula (IIc).

According to one embodiment of the present invention there is provided a method of treating obesity, comprising administration of a compound of formula (I). According to one embodiment of the present invention there is provided a method of treating obesity, comprising administration of a compound of formula (Ia).

According to one embodiment of the present invention there is provided a method of treating obesity, comprising administration of a compound of formula (II). According to one embodiment of the present invention there is provided a method of treating obesity, comprising administration of a compound of formula (IIa). According to one embodiment of the present invention there is provided a method of treating obesity, comprising administration of a compound of formula (IIb). According to one embodiment of the present invention there is provided a method of treating obesity, comprising administration of a compound of formula (IIc).

According to one embodiment of the present invention there is provided a method of treating diabetes mellitus, comprising administration of a compound of formula (I). According to one embodiment of the present invention there is provided a method of treating diabetes mellitus, comprising administration of a compound of formula (Ia).

According to one embodiment of the present invention there is provided a method of treating diabetes mellitus, comprising administration of a compound of formula (II). According to one embodiment of the present invention there is provided a method of treating diabetes mellitus, comprising administration of a compound of formula (IIa). According to one embodiment of the present invention there is provided a method of treating diabetes mellitus, comprising administration of a compound of formula (IIb). According to one embodiment of the present invention there is provided a method of treating diabetes mellitus, comprising administration of a compound of formula (IIc).

According to one embodiment of the present invention there is provided a pharmaceutical composition comprising a therapeutically effective amount of a compound of formula (I) in combination with a pharmaceutically suitable carrier. According to one embodiment of the present invention there is provided a pharmaceutical composition comprising a therapeutically effective amount of a compound of formula (Ia) in combination with a pharmaceutically suitable carrier.

According to one embodiment of the present invention there is provided a pharmaceutical composition comprising a therapeutically effective amount of a compound of formula (II) in combination with a pharmaceutically suitable carrier. According to one embodiment of the present invention there is provided a pharmaceutical composition comprising a therapeutically effective amount of a compound of formula (IIa) in combination with a pharmaceutically suitable carrier. According to one embodiment of the present invention there is provided a pharmaceutical composition comprising a therapeutically effective amount of a compound of formula (IIb in combination with a pharmaceutically suitable carrier. According to one embodiment of the present invention there is provided a pharmaceutical composition comprising a therapeutically effective amount of a compound of formula (IIc) in combination with a pharmaceutically suitable carrier.

According to one embodiment of the present invention there is provided a method of treating disorders regulated by ghrelin including anorexia, cancer cachexia, eating disorders, age-related decline in body composition, weight gain, obesity, and diabetes mellitus.

According to still another embodiment, the present invention is directed to a pharmaceutical composition comprising a therapeutically effective amount of a compound of the present invention in combination with a pharmaceutically suitable carrier. Specific compounds of formula (I) include, but are not limited to:

N-(4-(diethylamino)phenyl)-8-methoxy-1,2,3,4-tetrahydronaphthalene-2-carboxamide;

N-(4-(diethylamino)phenyl)-8-methoxy-2-methyl-1,2,3,4-tetrahydronaphthalene-2-carboxamide;

tert-butyl 2-(((4-(diethylamino)phenyl)amino)carbonyl)-1,2,3,4-tetrahydronaphthalen-2-ylcarbamate;

N-(4-(diethylamino)phenyl)-1,1-dimethyl-1,2,3,4-tetrahydronaphthalene-2-carboxamide;

N-(4-(diethylamino)phenyl)-8-ethoxy-1,2,3,4-tetrahydronaphthalene-2-carboxamide;

8-(allyloxy)-N-(4-(diethylamino)phenyl)-1,2,3,4-tetrahydronaphthalene-2-carboxamide;

tert-butyl 2-(((4-(diethylamino)-2-methylphenyl)amino)carbonyl)-1,2,3,4-tetrahydronaphthalen-2-ylcarbamate;

ethyl 2-(((4-(diethylamino)phenyl)amino)carbonyl)-1,2,3,4-tetrahydronaphthalen-2-ylcarbamate;

isobutyl 2-(((4-(diethylamino)phenyl)amino)carbonyl)-1,2,3,4-tetrahydronaphthalen-2-ylcarbamate;

benzyl 2-(((4-(diethylamino)phenyl)amino)carbonyl)-1,2,3,4-tetrahydronaphthalen-2-ylcarbamate;

tert-butyl 2-(((4-(diethylamino)phenyl)amino)carbonyl)-1,2,3,4-tetrahydronaphthalen-2-yl(methyl)carbamate;

methyl 2-(((4-(diethylamino)-2-methylphenyl)amino)carbonyl)-8-methoxy-1,2,3,4-tetrahydronaphthalene-2-carboxylate;

N-(4-(diethylamino)phenyl)-2-((N-isopropylglycyl)amino)-1,2,3,4-tetrahydronaphthalene-2-carboxamide;

tert-butyl 8-bromo-2-(((4-(diethylamino)phenyl)amino)carbonyl)-1,2,3,4-tetrahydronaphthalen-2-ylcarbamate;

isobutyl 2-(((4-(diethylamino)phenyl)amino)carbonyl)-1,2,3,4-tetrahydronaphthalen-2-yl(methyl)carbamate;

isobutyl 2-(((4-(diethylamino)phenyl)amino)carbonyl)-1,2,3,4-tetrahydronaphthalene-2-carboxylate;

3-methylbutyl 2-(((4-(diethylamino)phenyl)amino)carbonyl)-1,2,3,4-tetrahydronaphthalene-2-carboxylate;

methyl N-((2-(((4-(diethylamino)phenyl)amino)carbonyl)-1,2,3,4-tetrahydronaphthalen-2-yl)carbonyl)valinate;

2-fluoroethyl 2-(((4-(diethylamino)phenyl)amino)carbonyl)-1,2,3,4-tetrahydronaphthalen-2-ylcarbamate;

neopentyl 2-(((4-(diethylamino)phenyl)amino)carbonyl)-1,2,3,4-tetrahydronaphthalen-2-ylcarbamate;

3-chloropropyl 2-(((4-(diethylamino)phenyl)amino)carbonyl)-1,2,3,4-tetrahydronaphthalen-2-ylcarbamate;

but-3-enyl 2-(((4-(diethylamino)phenyl)amino)carbonyl)-1,2,3,4-tetrahydronaphthalen-2-ylcarbamate;

hexyl 2-(((4-(diethylamino)phenyl)amino)carbonyl)-1,2,3,4-tetrahydronaphthalen-2-ylcarbamate;

but-3-ynyl 2-(((4-(diethylamino)phenyl)amino)carbonyl)-1,2,3,4-tetrahydronaphthalen-2-ylcarbamate;

allyl 2-(((4-(diethylamino)phenyl)amino)carbonyl)-1,2,3,4-tetrahydronaphthalen-2-ylcarbamate;

butyl 2-(((4-(diethylamino)phenyl)amino)carbonyl)-1,2,3,4-tetrahydronaphthalen-2-ylcarbamate;

propyl 2-(((4-(diethylamino)phenyl)amino)carbonyl)-1,2,3,4-tetrahydronaphthalen-2-ylcarbamate;

but-2-ynyl 2-(((4-(diethylamino)phenyl)amino)carbonyl)-1,2,3,4-tetrahydronaphthalen-2-ylcarbamate;

$N^2$-(4-(diethylamino)phenyl)-($N^1$,$N^1$-dimethylglycinamide)-3,4-dihydronaphthalene-2,2(1H)-dicarbox pentyl 2-(((4-(diethylamino)phenyl)amino)carbonyl)-1,2,3,4-tetrahydronaphthalen-2-ylcarbamate;

isobutyl 2-(((4-(diethylamino)phenyl)amino)carbonyl)-8-methoxy-1,2,3,4-tetrahydronaphthalen-2-ylcarbamate;

isobutyl 2-(((4-(diethylamino)-2-methylphenyl)amino)carbonyl)-8-methoxy-1,2,3,4-tetrahydronaphthalen-2-ylcarbamate;

isobutyl 2-(((4-(diethylamino)phenyl)amino)carbonyl)-8-methoxy-1,2,3,4-tetrahydronaphthalen-2-yl(methyl)carbamate;

isobutyl 2-(((4-(diethylamino)-2-methylphenyl)amino)carbonyl)-8-methoxy-1,2,3,4-tetrahydronaphthalen-2-yl(methyl)carbamate;

isobutyl 8-bromo-2-(((4-(diethylamino)phenyl)amino)carbonyl)-1,2,3,4-tetrahydronaphthalen-2-ylcarbamate;

isobutyl(2R)-8-chloro-2-(((4-(diethylamino)phenyl)amino)carbonyl)-1,2,3,4-tetrahydronaphthalen-2-ylcarbamate;

neopentyl(2R)-8-chloro-2-(((4-(diethylamino)phenyl)amino)carbonyl)-1,2,3,4-tetrahydronaphthalen-2-ylcarbamate;

neopentyl(2R)-8-chloro-2-(((4-(diethylamino)-2-methylphenyl)amino)carbonyl)-1,2,3,4-tetrahydronaphthalen-2-ylcarbamate;

isobutyl(2R)-8-chloro-2-(((4-(diethylamino)phenyl)amino)carbonyl)-1,2,3,4-tetrahydronaphthalen-2-yl(methyl)carbamate;

isobutyl(2S)-2-(((4-(dibutylamino)phenyl)amino)carbonyl)-1,2,3,4-tetrahydronaphthalen-2-ylcarbamate;

isobutyl(2S)-2-(((4-(2,4-diamino-6-ethylpyrimidin-5-yl)phenyl)amino)carbonyl)-1,2,3,4-tetrahydronaphthalen-2-ylcarbamate;

isobutyl(2S)-6-bromo-2-(((4-(diethylamino)phenyl)amino)carbonyl)-1,2,3,4-tetrahydronaphthalen-2-ylcarbamate;

2-methyl-2-nitropropyl(2R)-2-(((4-(diethylamino)phenyl)amino)carbonyl)-1,2,3,4-tetrahydronaphthalen-2-ylcarbamate;

isobutyl(2S)-6-((1E)-3-amino-3-oxoprop-1-enyl)-2-(((4-(diethylamino)phenyl)amino)carbonyl)-1,2,3,4-tetrahydronaphthalen-2-ylcarbamate;

isobutyl(2S)-2-(((4-(diethylamino)phenyl)amino)carbonyl)-6-methoxy-1,2,3,4-tetrahydronaphthalen-2-ylcarbamate;

2-(dimethylamino)-2-methylpropyl(2R)-2-(((4-(diethylamino)phenyl)amino)carbonyl)-1,2,3,4-tetrahydronaphthalen-2-ylcarbamate;

(2S)-tetrahydrofuran-2-ylmethyl(2S)-2-(((4-(diethylamino)phenyl)amino)carbonyl)-1,2,3,4-tetrahydronaphthalen-2-ylcarbamate;

pyridin-3-ylmethyl(2S)-2-(((4-(diethylamino)phenyl)amino)carbonyl)-1,2,3,4-tetrahydronaphthalen-2-ylcarbamate;

isopropyl(2S)-2-(((4-(diethylamino)phenyl)amino)carbonyl)-1,2,3,4-tetrahydronaphthalen-2-ylcarbamate;

2-chloroethyl(2S)-2-(((4-(diethylamino)phenyl)amino)carbonyl)-1,2,3,4-tetrahydronaphthalen-2-ylcarbamate;

2-bromoethyl(2S)-2-(((4-(diethylamino)phenyl)amino)carbonyl)-1,2,3,4-tetrahydronaphthalen-2-ylcarbamate;

2-methoxyethyl(2S)-2-(((4-(diethylamino)phenyl)amino)carbonyl)-1,2,3,4-tetrahydronaphthalen-2-ylcarbamate;

isobutyl(2R)-2-(((4-(diethylamino)phenyl)amino)carbonyl)-1,2,3,4-tetrahydronaphthalen-2-yl(ethyl)carbamate;

The present compounds can exist as therapeutically suitable salts. The term "therapeutically suitable salt," refers to salts or zwitterions of the compounds which are water or oil-soluble or dispersible, suitable for treatment of disorders without undue toxicity, irritation, and allergic response, commensurate with a reasonable benefit/risk ratio, and effective for their intended use. The salts can be prepared during the final isolation and purification of the compounds or separately by reacting an amino group of the compounds with a suitable acid. Representative salts include acetate, adipate, alginate, citrate, aspartate, benzoate, benzenesulfonate, bisulfate, butyrate, camphorate, camphorsulfonate, digluconate, glycerophosphate, hemisulfate, heptanoate, hexanoate, formate, isethionate, fumarate, lactate, maleate, methanesulfonate, naphthylenesulfonate, nicotinate, oxalate, pamoate, pectinate, persulfate, 3-phenylpropionate, picrate, oxalate, maleate, pivalate, propionate, succinate, tartrate, trichloroacetic, trifluoroacetic, glutamate, para-toluenesulfonate, undecanoate, hydrochloric, hydrobromic, sulfuric, phosphoric, and the like. The amino groups of the compounds can also be quaternized with alkyl chlorides, bromides, and iodides such as methyl, ethyl, propyl, isopropyl, butyl, lauryl, myristyl, stearyl, and the like.

Basic addition salts can be prepared during the final isolation and purification of the present compounds by reaction of a carboxyl group with a suitable base such as the hydroxide, carbonate, or bicarbonate of a metal cation such as lithium, sodium, potassium, calcium, magnesium, or aluminum, or an organic primary, secondary, or tertiary amine. Quaternary amine salts derived from methylamine, dimethylamine, trimethylamine, triethylamine, diethylamine, ethylamine, tributlyamine, pyridine, N,N-dimethylaniline, N-methylpiperidine, N-methylmorpholine, dicyclohexylamine, procaine, dibenzylamine, N,N-dibenzylphenethylamine, 1-ephenamine, and N,N'-dibenzylethylenediamine, ethylenediamine, ethanolamine, diethanolamine, piperidine, piperazine, and the like, are contemplated as being within the scope of the present invention.

The present compounds can also exist as therapeutically suitable prodrugs. The term "therapeutically suitable prodrug," refers to those prodrugs or zwitterions which are suitable for use in contact with the tissues of patients without undue toxicity, irritation, and allergic response, are commensurate with a reasonable benefit/risk ratio, and are effective for their intended use. The term "prodrug," refers to compounds which are rapidly transformed in vivo to the parent compounds of the present invention for example, by hydrolysis in blood.

Asymmetric centers can exist in the present compounds. Individual stereoisomers of the compounds are prepared by synthesis from chiral starting materials or by preparation of racemic mixtures and separation by conversion to a mixture of diastereomers followed by separation or recrystallization, chromatographic techniques, or direct separation of the enantiomers on chiral chromatographic columns. Starting materials of particular stereochemistry are either commercially available or are made by the methods described hereinbelow and resolved by techniques well-known in the art.

Geometric isomers can exist in the present compounds. The invention contemplates the various geometric isomers and mixtures thereof resulting from the disposal of substituents around a carbon-carbon double bond, a cycloalkyl group, or a heterocycloalkyl group. Substituents around a carbon-carbon double bond are designated as being of Z or E configuration and substituents around a cycloalkyl or heterocycloalkyl are designated as being of cis or trans configuration.

Therapeutic compositions of the present compounds comprise an effective amount of the same formulated with one or more therapeutically suitable excipients. The term "therapeutically suitable excipient," as used herein, represents a non-toxic, solid, semi-solid or liquid filler, diluent, encapsulating material, or formulation auxiliary of any type. Examples of therapeutically suitable excipients include sugars; cellulose and derivatives thereof, oils; glycols; solutions; buffering, coloring, releasing, coating, sweetening, flavoring, and perfuming agents; and the like. These therapeutic compositions can be administered parenterally, intracistemally, orally, rectally, or intraperitoneally.

Liquid dosage forms for oral administration of the present compounds comprise formulations of the same as emulsions, microemulsions, solutions, suspensions, syrups, and elixirs. In addition to the compounds, the liquid dosage forms can contain diluents and/or solubilizing or emulsifying agents. Besides inert diluents, the oral compositions can include wetting, emulsifying, sweetening, flavoring, and perfuming agents. Injectable preparations of the present compounds comprise sterile, injectable, aqueous and oleaginous solutions, suspensions or emulsions, any of which can be optionally formulated with parenterally suitable diluents, dispersing, wetting, or suspending agents. These injectable preparations can be sterilized by filtration through a bacterial-retaining filter or formulated with sterilizing agents which dissolve or disperse in the injectable media.

Regulation of the effects of ghrelin by the compounds of the present invention can be delayed by using a liquid suspension of crystalline or amorphous material with poor water solubility. The rate of absorption of the compounds depends upon their rate of dissolution which, in turn, depends on their crystalline form. Delayed absorption of a parenterally administered compound can be accomplished by dissolving or suspending the compound in oil. Injectable depot forms of the compounds can also be prepared by microencapsulating the same in biodegradable polymers. Depending upon the ratio of compound to polymer and the nature of the polymer employed, the rate of release can be controlled. Depot injectable formulations are also prepared by entrapping the compounds in liposomes or microemulsions which are compatible with body tissues.

Solid dosage forms for oral administration of the present compounds include capsules, tablets, pills, powders, and granules. In such forms, the compound is mixed with at least one inert, therapeutically suitable excipient such as a carrier, filler, extender, disintegrating agent, solution retarding agent, wetting agent, absorbent, or lubricant. With capsules, tablets, and pills, the excipient can also contain buffering agents. Suppositories for rectal administration can be prepared by mixing the compounds with a suitable non-irritating excipient which is solid at ordinary temperature but fluid in the rectum.

The present compounds can be micro-encapsulated with one or more of the excipients discussed previously. The solid dosage forms of tablets, dragees, capsules, pills, and granules can be prepared with coatings and shells such as enteric and release-controlling. In these forms, the compounds can be mixed with at least one inert diluent and can optionally comprise tableting lubricants and aids. Capsules can also optionally contain opacifying agents which delay release of the compounds in a desired part of the intestinal tract.

Transdermal patches have the added advantage of providing controlled delivery of the present compounds to the body. Such dosage forms are prepared by dissolving or dispensing the compounds in the proper medium. Absorption enhancers can also be used to increase the flux of the compounds across the skin, and the rate of absorption can be controlled by providing a rate controlling membrane or by dispersing the compounds in a polymer matrix or gel.

Disorders that may be regulated by ghrelin are treated or prevented in a patient by administering to the patient, a therapeutically effective amount of compound of the present invention in such an amount and for such time as is necessary to achieve the desired result. The term "therapeutically effective amount," refers to a sufficient amount of a compound to effectively emeliorate disorders reglulated by ghrelin at a reasonable benefit/risk ratio applicable to any medical treatment. The specific therapeutically effective dose level for any particular patient will depend upon a variety of factors including the disorder being treated and the severity of the disorder; the activity of the compound employed; the specific composition employed; the age, body weight, general health, sex, and diet of the patient; the time of administration, route of administration, rate of excretion; the duration of the treatment; and drugs used in combination or coincidental therapy.

The total daily dose of the present compounds in single or divided doses can be in amounts, for example, from 0.01 to 50 mg/kg body weight or more usually from 0.1 to 25 mg/kg body weight. In general, treatment regimens comprise administration to a patient in need of such treatment from about 10 mg to about 1000 mg of the compounds per day in single or multiple doses.

Determination of Biological Activity

The activities of the ghrelin receptor modulators, including both agonists and antagonists, have been determined using a primary binding assay and a secondary functional assay.

Primary Radiolabelled Ligand Competition Binding Assay

Ghrelin binding assays were performed with membrane preparations. CHO-K cells expressing human ghrelin receptor (Euroscreen) were suspended in sucrose buffer (0.25 M sucrose, 10 mM hepes pH 7.4, 1 mM PMSF, 5 ug/ml pepstain-A, 3 mM EDTA and 0.025% bacitracin) and disrupted by sonication using a vibra cell (Sonics and Materials Inc.) on 70% duty cycle in 15-second pulses on ice for 2.5 min. The homogenate was centrifuged at 60,000×g for 60 minutes and pellets were suspended in tris buffer (20 mM tris pH 7.4, 5 ug/ml pepstatin-A, 0.1 mM PMSF and 3 mM EDTA). Binding reactions contained 1 ug membrane as determined by BCA protein assay (Pierce), 0.1 nM ($^{125}$I)-ghrelin (PerkinElmer) with or without compound addition in 100 ul of binding buffer (25 mM Hepes pH 7.4, 1 mM $CaCl_2$, 5 mM $MgSO_4$ and 0.5% protease free BSA). Incubations were carried out at room temperature for 2 hr and were terminated by filtration using Filtermate Harvester (PerkinElmer) onto GF/C filter plates (Millipore) previously soaked in 0.5% polyethylenimine for 2 hours. Bound ($^{125}$I)-ghrelin was determined by scintillation counting using Top Count NXT (PerkinElmer). The effects of compound were expressed as % inhibiton of ($^{125}$I)-ghrelin binding. Sigmoidal curves were fitted by Assay Explorer (MDL) software and $IC_{50}$ values determined.

Secondary Fluorescent Calcium Indicator Assay (FLIPR)

CHO-K cells expressing human GHS receptor (Euroscreen) were plated in black 96-well plates with clear bottom (Costar) and cultured to confluency overnight in growth media (Ultra-CHO from BioWhittaker supplemented with 1% dialyzed FCS, 1% penicillin/streptomycin/fungizone, and 400 ug/ml G418 all from Life Technologies) at 37° C. in a humidified cell incubator containing 5% $CO_2$. Growth media was aspirated and replaced with 100 ul of Dulbecco's phosphate-buffered saline (DPBS) containing 1,000 mg/l D-glucose, 36 mg/l sodium pyruvate, without phenol red (Life Technologies) with 1.14 mM Fluo-4 AM (Molecular Probes) and 0.25 M probenecid (Sigma) for 1 to 3 hours in the dark at room temperature. The dye solution was aspirated and the cells were washed twice with DPBS using the EL-450X cell washer (BioTech). After the last wash, 100 ul of DPBS was added to each well. Cell plates were then transferred to the FLIPR unit (Molecular Probes). Compound additions were 50 ul in duplicate of 4× final concentration in DPBS containing 0.1% BSA and 4% DMSO. Fluorescence emissions from 96 wells were measured simultaneously at excitation and emission wavelength of 488 and 520 nm, respectively for 3 minutes in 1-second intervals for the first minute and 5-second intervals thereafter. During this time agonist responses, if any, were recorded in the absence of ghrelin. Next, 50 ul in duplicate of 4× concentrated ghrelin (Bachem) solution in DPBS containing 0.1% BSA and 4% DMSO were delivered within 1 second by an integrated 96-well pipettor to a final concentration of 1 nM. Fluorescence emissions were measured for another 3 minutes as above. During this time the antagonist effects of compounds on ghrelin-stimulated calcium flux were recorded and expressed as % inhibition of the maximal ghrelin response (10 nM). Sigmoidal curves were fitted by Assay Explorer (MDL) software and $IC_{50}$ values determined. In addition, the agonist effects of the compounds could also be obtained and expressed as % maximal ghrelin response (10 nM). Sigmoidal curves were fitted by Assay Explorer (MDL) software and $EC_{50}$ values determined.

The instant compounds were found to modulate the activity of the ghrelin receptor with $IC_{50}/EC_{50}$ in a range of about 0.001 μM to about 10 μM in both the binding and FLIPR assays. In a preferred range, the compounds modulated the ghrelin receptor with $IC_{50}/EC_{50}$ in a range of about 0.001 μM to about 1.0 μM in both the binding and FLIPR assays; and in a more preferred range, the compounds modulated the ghrelin receptor with $IC_{50}/EC_{50}$ in a range of about 0.001 μM to about 0.2 μM in both the binding and FLIPR assays.

Schemes

The compounds and processes of the present invention will be better understood in connection with the following synthetic schemes which illustrate the methods by which the compounds of the invention may be prepared. The schemes are intended to illustrate the methods by which compounds of formula (I)

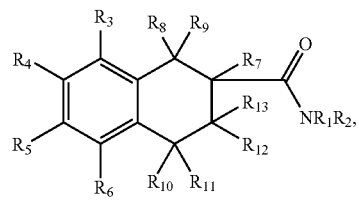

may be prepared. Groups $R_7$, $R_8$, $R_9$, $R_{10}$, $R_{11}$, $R_{12}$ and $R_{13}$ are not shown in the general formulas described in the schemes, but are intended to be incorporated in the scope of the general formulas and thus incorporated in the methods describing the synthesis of the compounds of the present invention. The groups $R_1$, $R_2$, $R_3$ and $R_4$ are as defined above unless otherwise noted below.

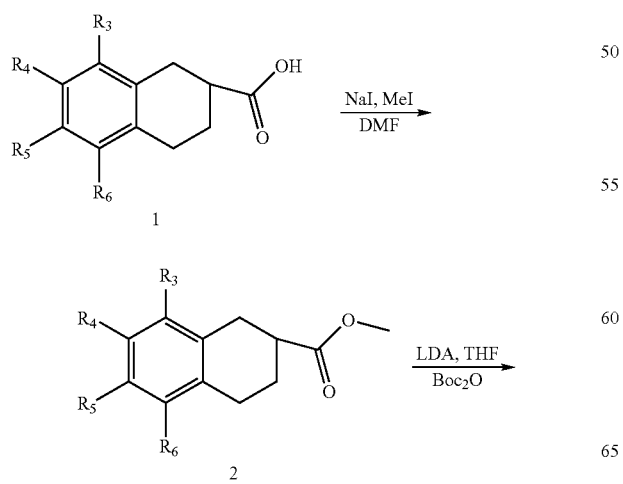

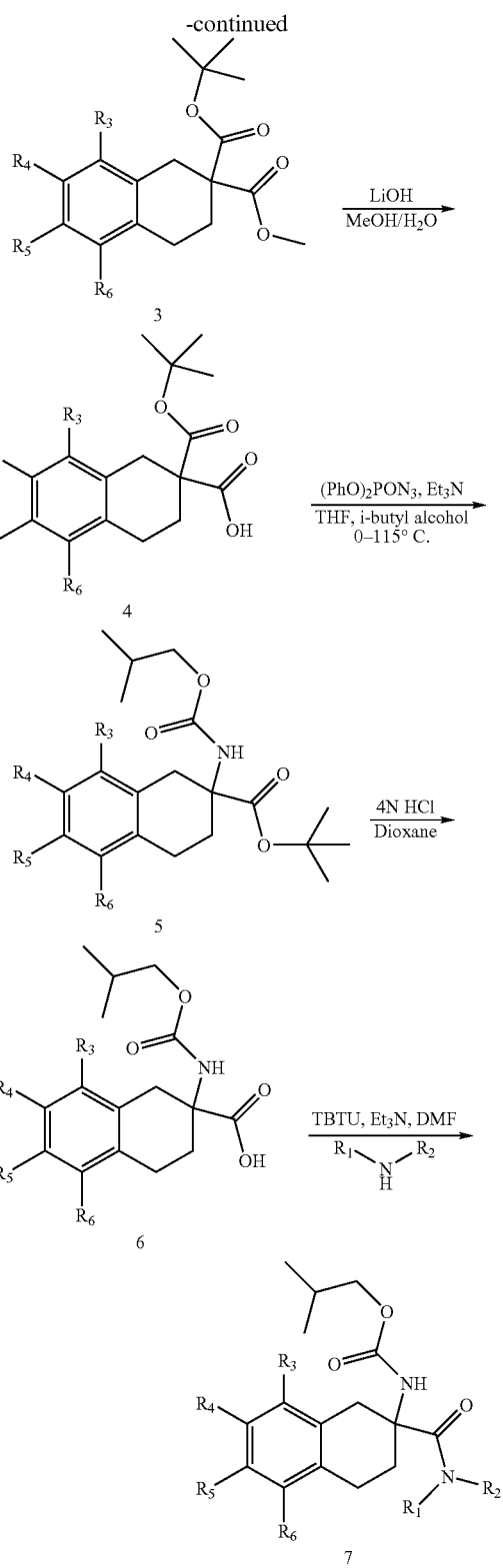

As shown in Scheme 1, compounds of general formula 1 when treated with reagents such as sodium iodide and methyl iodide in solvents such as but not limited to DMF will provide compounds of general formula 2. Compounds of general formula 2 when treated with lithium diisopropylamine in solvents such as but not limited to THF and the like followed by treatment with di-tert-butyl dicarbonate will provide compounds of general formula 3. Compounds of general formula 3 are treated with reagents known to those skilled in the art to hydrolyze methyl esters such as but not limited to lithium hydroxide, sodium hydroxide and the like in solvents such as but not limited to aqueous methanol will provide compounds of general formula 4. Compounds of general formula 4 when treated with diphenoxyphosphonium azide and triethyl amine is a mixture of THF and iso-butyl alcohol under heated conditions will provide compounds of general formula 5. Compounds of general formula 5 when treated with strong acids such as but not limited to 4 N hydrochloric acid in dioxane or trifluoroacetic acid in dichloromethane will provide compounds of general formula 6. The reaction between compounds of general formula 6 and amines of general formula $R_1R_2NH$ can be affected through many reagents including TBTU and triethylamine in solvents such as but not limited to DMF to provide compounds of general formula 7. Compounds of general formula 7 are representative of compounds of the present invention when $R_7$ is $R_cR_dN$— and $R_c$ is alkoxycarbonyl. Other useful reagents known to couple acids of general formula 6 to amines of general formula $R_1R_2NH$ include but are not limited to dicyclohexylcarbodiimide, 1-(3-dimethylaminopropyl)-3-ethylcarbodiimide hydrochloride and the like.

Scheme 2

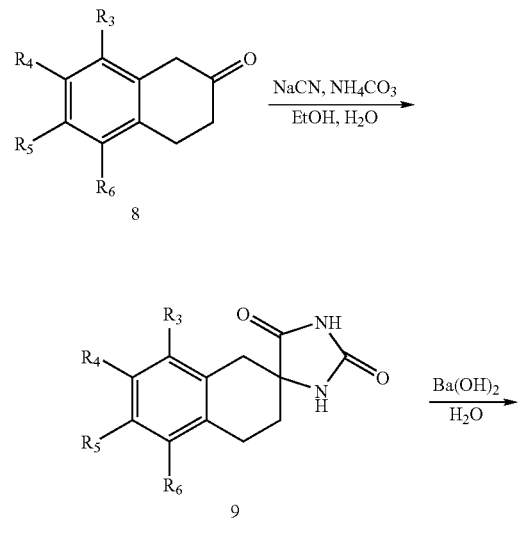

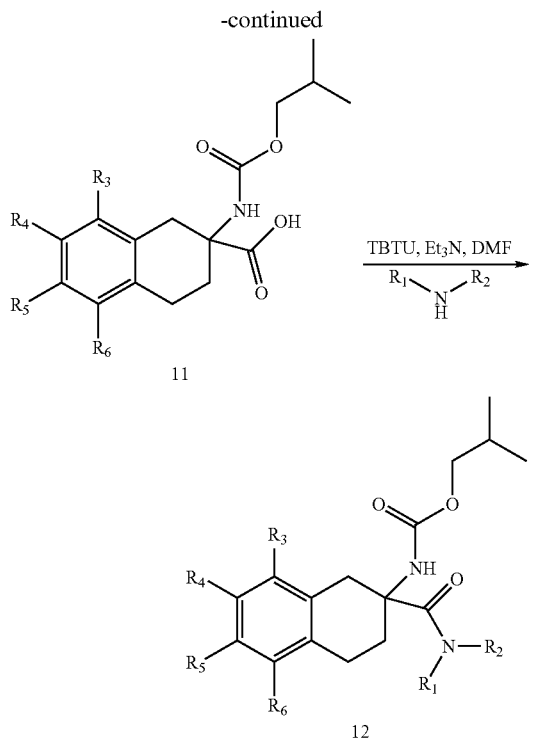

As shown in Scheme 2, compounds of formula 8 when treated with sodium cyanide, ammonium carbonate heated in a pressure tube in a mixture of ethanol and water will probide compounds of general formula 9. Compounds of general formula 9 when treated with barium hydroxide in water will provide compounds of general formula 10. Compounds of general formula 10 when treated with the portionwise addition of reagents such as but not limited to iso-butyl chloroformate along with the slow addition of aqueous sodium hydroxide in dioxane will produce compounds of formula 11. Compound of formula 11 can be treated with amines of general formula $R_1R_2NH$ along with TBTU and triethylamine in solvents such as but not limited to DMF to provide compounds of general formula 12 which are representative of the compounds of the present invention when $R_7$ is $R_cR_dN$— and $R_c$ is alkoxycarbonyl. The reaction of the acid functionality of compounds of general formula 11 with compounds of general formula $R_1R_2NH$ can also be effected through the methods outlined in Scheme 1 or through methods known to those skilled in the art to couple amines to carboxylic acid.

Scheme 3

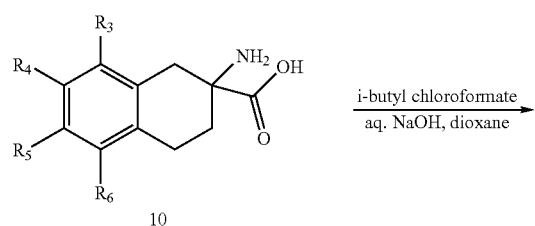

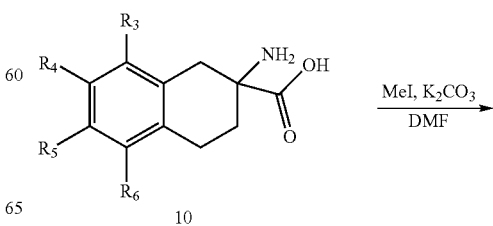

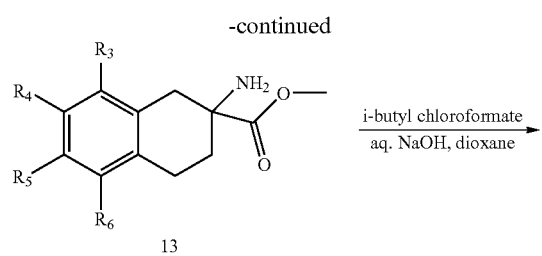

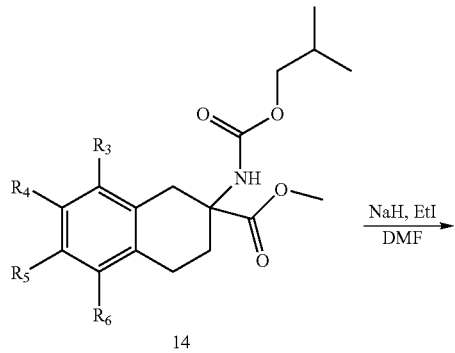

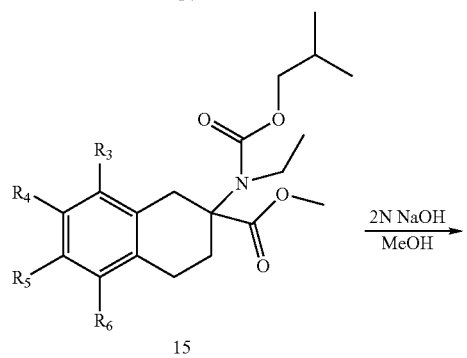

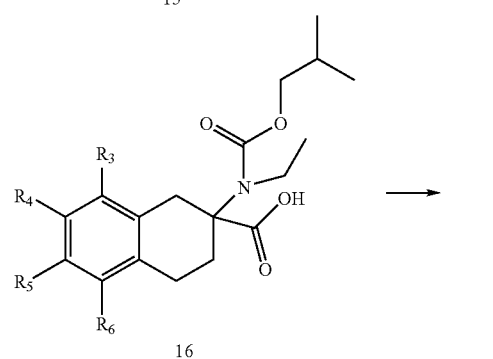

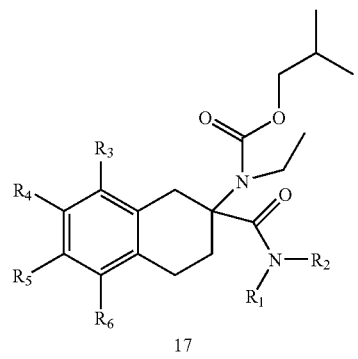

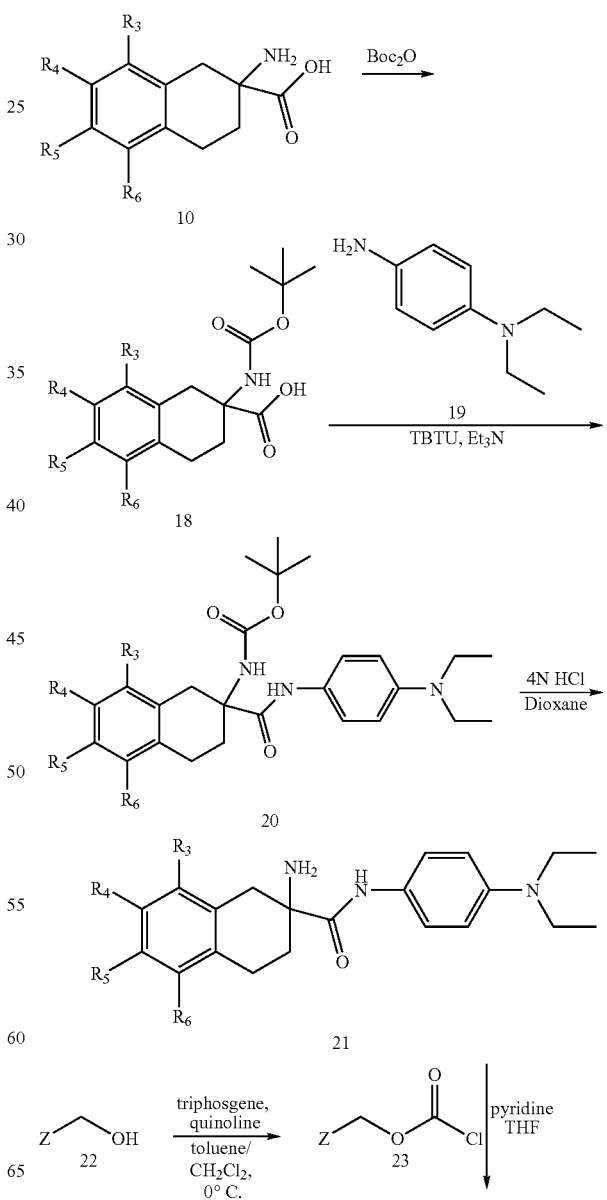

As shown in Scheme 3, compounds of general formula 10 when treated with methyl iodide and potassium carbonate in DMF to provide compounds of general formula 13. Compounds of general formula 13 when treated with portionwise addition of reagents such as but not limited to iso-butyl chloroformate along with the slow addition of aqueous sodium hydroxide in dioxane will provide compounds of general formula 14. Compounds of general formula 14 when treated first with sodium hydride in DMF followed by the addition of ethyl iodide will provide compounds of general formula 15. Compounds of general formula 15 when treated with sodium hydroxide, potassium hydroxide or lithium hydroxide in solvents such as but not limited to methanol will provide compounds of general formula 16. Compounds of general formula 16 can be treated according to conditions described in Schemes 1 or 2 to couple the acid functionality to an amine of general formula $R_1R_2NH$ to provide compounds of general formula 17 which are representative of compounds of the present invention.

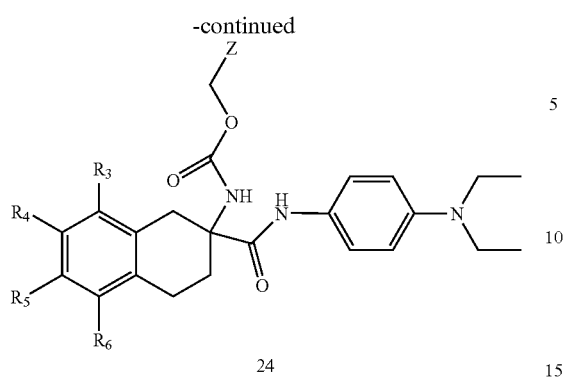

As shown in Scheme 4, compounds of general formula 10 can be treated with di-tert-butyl dicarbonate in solvents such as but not limited to THF to provide compounds of general formula 18. Compounds of general formula 18 can be treated with compounds of general formula 19 and coupling reagents such as TBTU, triethylamine or others previously mentioned to provide compounds of general formula 20. Compounds of general formula 20 can be treated with reagents known to deprotect tert-butyloxy carbonyl(Boc) groups such as 4 N hydrochloric acid in dioxane to provide compounds of general formula 21. The amine functionality of compounds of general formula 21 can be treated with compounds of general formula 23 in the presence of pyridine in solvents such as but not limited to THF to provide compounds of general formula 24 which are representative of compounds of the present invention. Compounds of general formula 23 can be made from compounds of general formula 22 when reacted with triphosgene and quinoline in a mixture of toluene and dichloromethane.

The present invention will now be described in connection with certain embodiments which are not intended to limit its scope. On the contrary, the present invention covers all alternatives, modifications, and equivalents as can be included within the scope of the claims. Thus, the following examples, which include preferred embodiments, will illustrate the preferred practice of the present invention, it being understood that the examples are for the purposes of illustration of certain preferred embodiments.

Compounds of the invention were named by ACD/ChemSketch version 5.01 (developed by Advanced Chemistry Development, Inc., Toronto, ON, Canada) or were given names which appeared to be consistent with ACD nomenclature.

Synthetic Methods

Abbreviations which have been used in the descriptions of the scheme and the examples that follow are: BBr$_3$ for boron tribromide; m-CPBA for meta-chloroperoxy-benzoic acid; DMF for N,N-dimethylformamide; DMSO for dimethylsulfoxide; DEAD for diethyl azodicarboxylate; EDAC for 1-(3-dimethylaminopropyl)-3-ethylcarbodiimide hydrochloride; HATU for O-(7-azabenzotriazol-1-yl)-N,N,N'N'-tetramethyluronium hexafluorophosphate; HOBT for 1-hydroxybenzotriazole hydrate; NMP for N-methylpyrrolidinone; NCS for N-chlorosuccinimide; MeONa for sodium methoxide; MeOH for methanol; MTBE for methyl tert butyl ether; THF for tetrahydrofuran; TFA for trifluoroacetic acid; TBAF for tetra butylammonium fluoride; Pd(dppf)Cl$_2$ for (diphenylphospino)ferrocenyl palladium chloride; Ph$_3$P for triphenylphosphine; Pr$_2$Net for diisopropyl ethylamine; and TBTU for (benzotriazol-1-yloxy)-dimethylamino-methylene)-dimethyl-ammonium tetrafluoroborate.

EXPERIMENTALS

Example 1

N-(4-(Diethylamino)phenyl)-8-methoxy-1,2,3,4-tetrahydronaphthalene-2-carboxamide To 8-methoxy-1,2,3,4-tetrahydro-naphthalene-2-carboxylic acid (206 mg, 1.0 mmol) in DMF (1.5 mL) was added N,N-diethylphenylene diamine sulfate (262 mg, 1.0 mmol), Et$_3$N (606 mg, 6.0 mmol), and TBTU (321 mg, 1.0 mmol) at 0° C. After stirred overnight, ice chips and 20 mL ethyl acetate were added. Organic layer was washed with water (3×10 mL), dried over MgSO$_4$, and then concentrated. Purification by column chromatography provided the titled compound (170 m g, 48%). $^1$H NMR (300 MHz, DMSO-D$_6$) δ 9.59 (s, 1H), 7.39 (d, J=9.3 Hz, 2H), 7.08 (t, J=7.8 Hz, 1H), 6.75 (d, J=7.8 Hz, 1H), 6.70 (d, J=7.8 Hz, 1H), 6.61 (d, J=9.0 Hz, 2H), 3.76 (s, 3H), 3.29 (q, J=6.9 Hz, 4H), 2.91–2.56 (m, 5H), 2.00 (m, 1H), 1.69 (m, 1H), and 1.06 (t, J=6.9 Hz, 6H). MS (ESI) positive ion 353 (M+H)$^+$; negative ion 351 (M−H)$^−$.

Example 2

N-(4-(Diethylamino)phenyl)-8-methoxy-2-methyl-1,2,3,4-tetrahydronaphthalene-2-carboxamide Example 2A 8-Methoxy-2-methyl-1,2,3,4-tetrahydro-naphthalene-2-carboxylic acid methyl ester To iPr$_2$NH (202 mg, 2.0 mmol) in THF (1.0 mL) was added BuLi (2.5 M, 0.8 mL, 2.0 mmol) at −78° C. After 10 minutes, 8-methoxy-1,2,3,4-tetrahydro-naphthalene-2-carboxylic acid methyl ester in THF (1.0 mL) was added and the reaction mixture turned yellow. Methyl iodide (568 mg, 4.0 mmol) and HMPA (1.0 mL) were added after 30 minutes. The reaction mixture was allowed to stir at −78° C. for 3 hours at ambient temperature before aqueous NH$_4$Cl was added. The mixture was extracted with ethyl acetate (3×20 mL) and the combined extracts were dried over MgSO$_4$ and purified by column chromatography to give 8-methoxy-2-methyl-1,2,3,4-tetrahydro-naphthalene-2-carboxylic acid methyl ester (170 mg, 84%).

Example 2B

N-(4-(Diethylamino)phenyl)-8-methoxy-2-methyl-1,2,3,4-tetrahydronaphthalene-2-carboxamide The ester from Example 2A (170 mg, 0.73 mmol) was dissolved in THF (2.0 mL) and a solution (3.0 mL) of N,N-Diethyl-benzene-1,4-diamine (332 mg, 2 mmol) and EtMgBr (2.0 mmol) in THF was added at 0° C. The reaction mixture was quenched with aqueous $NH_4Cl$ after 3 hours. The mixture was extracted with ethyl acetate (3×15 mL) and the combined extracts were dried over $MgSO_4$ and purified by column chromatography to provide the titled compound (30 mg, 8%). $^1$H NMR (400 MHz, DMSO-$D_6$) δ 9.03 (s, 1H), 7.33 (d, J=9.2 Hz, 2H), 7.03 (t, J=8.0 Hz, 1H), 6.72 (d, J=7.6 Hz, 1H), 6.73 (d, J=8.0 Hz, 1H), 6.58 (d, J=9.2 Hz, 2H), 3.77 (s, 3H), 3.27 (q, J=7.2 Hz, 4H), 3.11 (d, J=17.2 Hz, 1H), 2.74 (t, J=6.4 Hz, 2H), 2.43 (d, J=17.2 Hz, 2H), 2.15 (ddd, J=6.4, 6.4, 13.2 Hz, 1H), 1.73 (ddd, J=7.2, 7.2, 13.6 Hz, 1H), 1.26 (s, 3H), and 1.04 (t, J=7.2 Hz, 6H). MS (ESI) positive ion 367 (M+H)$^+$; negative ion 365 (M−H)$^-$.

Example 3 tert-Butyl 2-(((4-(diethylamino)phenyl)amino)carbonyl)-1,2,3,4-tetrahydronaphthalen-2-ylcarbamate The titled compound was prepared according to the procedure described in Example 1, substituting 2-tert-butoxycarbonylamino-1,2,3,4-tetrahydro-naphthalene-2-carboxylic acid for 8-methoxy-1,2,3,4-tetrahydro-naphthalene-2-carboxylic acid used in Example 1. $^1$H NMR (300 MHz, DMSO-$D_6$) δ 9.13 (s, 1H), 7.32 (d, J=8.7 Hz, 2H), 7.08 (m, 4H), 6.74 (s, 1H), 6.61 (d, J=9.0 Hz, 2H), 3.28 (q, J=7.2 Hz, 4H), 3.00 (d, J=18.0 Hz, 1H), 2.73 (m, 2H), 2.36 (m, 1H), 2.05 (m, 1H), 1.35 (s, 9H), and 1.05 (t, J=7.2 Hz, 6H). (one proton (ArCH$_a$H$_b$C(=O)) overlapped with water)). MS (ESI) positive ion 438 (M+H)$^+$; negative ion 436 (M−H)$^-$.

Example 4

N-(4-(Diethylamino)phenyl)-1,1-dimethyl-1,2,3,4-tetrahydronaphthalene-2-carboxamide The titled compound was prepared according to the procedure described in Example 1, substituting 1,1-dimethyl-1,2,3,4-tetrahydro-naphthalene-2-carboxylic acid for 8-methoxy-1,2,3,4-tetrahydro-naphthalene-2-carboxylic acid used in Example 1. MS (ESI(+)) m/e 351 (M+H)$^+$; $^1$H NMR (300 MHz, DMSO-$d_6$) δ 9.49 (s, 1H), 7.37 (d, J=9.2 Hz, 2H), 7.16–7.02 (m, 3H), 6.60 (d, J=9.2 Hz, 2H), 3.28 (q, J=7.1 Hz, 4H), 2.97–2.71 (m, 2H), 2.55 (dd, J1=3.4 Hz, J2=10.5 Hz, 1H), 2.09–1.83 (m, 2H), 1.37 (s, 3H), 1.26 (s, 3H), 1.05 (t, J=6.8 Hz, 6H).

Example 5

N-(4-(Diethylamino)phenyl)-8-ethoxy-1,2,3,4-tetrahydronaphthalene-2-carboxamide

The titled compound was prepared according to the procedure described in Example 1, substituting 8-ethoxy-1,2,3,4-tetrahydro-naphthalene-2-carboxylic acid for 8-methoxy-1,2,3,4-tetrahydro-naphthalene-2-carboxylic acid used in Example 1. $^1$H NMR (300 MHz, DMSO-$D_6$) δ 9.61 (s, 1H), 7.40 (d, J=9.3 Hz, 2H), 7.05 (t, J=7.8 Hz, 1H), 6.73 (d, J=7.8 Hz, 1H), 6.70 (d, J=7.8 Hz, 1H), 6.62 (d, J=9.0 Hz, 2H), 4.00 (m, 2H), 3.28 (q, J=6.9 Hz, 4H), 2.91–2.56 (m, 5H), 1.99 (m, 1H), 1.67 (m, 1H), 1.33 (t, J=7.2 Hz, 3H), and 1.06 (t, J=6.6 Hz, 6H). MS (ESI) positive ion 367 (M+H)$^+$; negative ion 365 (M−H)$^-$.

Example 6

8-(Allyloxy)-N-(4-(diethylamino)phenyl)-1,2,3,4-tetrahydronaphthalene-2-carboxamide Example 6A 8-Hydroxy-1,2,3,4-tetrahydro-naphthalene-2-carboxylic acid To 8-Methoxy-1,2,3,4-tetrahydro-naphthalene-2-carboxylic acid methyl ester (660 mg, 3.0 mmol) in dichloromethane (3.0 mL) was added $BBr_3$ (1 M, 3.0 mL, 3.0 mmol) at −78° C. The mixture was stirred for 3 hour and then worked up to give 8-hydroxy-1,2,3,4-tetrahydro-naphthalene-2-carboxylic acid (470 mg, 2.3 mmol, 77%).

Example 6B

8-Hydroxy-1,2,3,4-tetrahydro-naphthalene-2-carboxylic acid (4-diethylamino-phenyl)-amide This phenol from Example 6A was dissolved in DMF (4.0 mL) and N,N-Diethyl-benzene-1,4-diamine sulfate (602 mg, 2.3 mmol), $Et_3N$ (707 mg, 7.0 mmol), and TBTU (738 mg, 2.3 mmol) were added at ambient temperature. The mixture was stirred overnight and purified by silica gel column chromatography to provide 8-hydroxy-1,2,3,4-tetrahydro-naphthalene-2-carboxylic acid (4-diethylamino-phenyl)-amide (480 mg, 62%).

Example 6C 8-(Allyloxy)-N-(4-(diethylamino)phenyl)-1,2,3,4-tetrahydronaphthalene-2-carboxamide The phenol from Example 6B (68 mg, 0.2 mmol) was dissolved in DMF (0.4 mL) and $K_2CO_3$ (41 mg, 0.2 mmol) and allyl bromide (36 mg, 0.3 mmol) were added at ambient temperature. The reaction mixture was worked up and purified by column chromatography to provide the titled compound (15 mg, 20%). $^1$H NMR (400 MHz, DMSO-$D_6$) δ 9.59 (s, 1H), 7.39 (d, J=9.2 Hz, 2H), 7.05 (t, J=8.0 Hz, 1H), 6.75 (d, J=8.0 Hz, 1H), 6.70 (d, J=8.0 Hz, 1H), 6.61 (d, J=9.2 Hz, 2H), 6.05 (ddddd, 5.2, 5.2, 10.8, 16.0 Hz, 1H), 5.39 (dddd, J=1.2, 1.2, 1.2, 15.2 Hz, 1H), 5.24 (dddd, J=1.2, 1.2, 1.2, 10.4 Hz, 1H), 4.55 (m, 2H), 3.28 (q, J=6.8 Hz, 4H), 2.3 (m, 1H), 2.79 (m, 2H), 2.61 (m, 2H), 1.99 (m, 1H), 1.69 (m, 1H), and 1.06 (t, J=6.8 Hz, 6H). MS (ESI) positive ion 379 (M+H)$^+$; negative ion 377 (M−H)$^-$.

Example 7 tert-Butyl 2-(((4-(diethylamino)-2-methylphenyl)amino)carbonyl)-1,2,3,4-tetrahydronaphthalen-2-ylcarbamate The titled compound was prepared according to the procedure described in Example 1, substituting 2-tert-butoxycarbonylamino-1,2,3,4-tetrahydro-naphthalene-2-carboxylic acid for 8-methoxy-1,2,3,4-tetrahydro-naphthalene-2-carboxylic acid, and N,N-diethyl-2-methyl-1,4-phenylenediamine for N,N-diethyl-1,4-phenylenediamine sulfate used in Example 1. $^1$H NMR (300 MHz, DMSO-$D_6$) δ 8.71 (s, 1H), 7.08 (m, 4H), 7.01 (d, J=8.4 Hz, 1H), 6.86 (s, 1H), 6.47 (m, 3H), 3.26 (q, J=7.5 Hz, 4H), 3.24 (d, J=15.6 Hz, 1H), 3.00 (d, J=16.5 Hz, 1H), 2.74 (m, 2H), 2.36 (m, 1H), 2.06 (m, 1H), 2.10 (s, 3H), 1.38 (s, 9H), and 1.06 (t, J=6.9 Hz, 6H). MS (ESI) positive ion 452 (M+H)$^+$; negative ion 450 (M−H)$^-$.

Example 8

Ethyl 2-(((4-(diethylamino)phenyl)amino)carbonyl)-1,2,3,4-tetrahydronaphthalen-2-ylcarbamate

Example 8A

2-Amino-1,2,3,4-tetrahydro-naphthalene-2-carboxylic acid (4-diethylamino-phenyl)-amide (2-(4-Diethylamino-phenylcarbamoyl)-1,2,3,4-tetrahydro-naphthalen-2-yl)-carbamic acid tert-butyl ester from Example 3 (320 mg) was dissolved in dichloromethane (10 mL) and TFA (5.0 mL). The volatiles were removed after 2 h. The amine-TFA salt was then dissolved in ethyl acetate (30 mL) and washed with 1 N NaOH. The organic phase was dried over $MgSO_4$ and purified by column chromatography to provide the titled compound (240 mg, 97%).

Example 8B

Ethyl 2-(((4-(diethylamino)phenyl)amino)carbonyl)-1,2,3,4-tetrahydronaphthalen-2-ylcarbamate The amine from Example 8A (34 mg, 0.1 mmol) was dissolved in THF (0.5 mL) and $Et_3N$ (15 mg, 0.1 mmol) and ethyl chloroformate (13 mg, 0.12 mmol) were added at 0° C. after which the mixture was allowed to stir overnight. HPLC purification gave the titled compound (10 mg, 24%). $^1$H NMR (300 MHz, DMSO-$D_6$) δ 9.14 (s, 1H), 7.32 (d, J=8.7 Hz, 2H), 7.08 (m, 4H), 7.08 (s, 1H), 6.61 (d, J=9.0 Hz, 2H), 3.96 (m, 2H), 3.28 (q, J=6.6 Hz, 4H), 3.02 (d, J=16.5 Hz, 1H), 2.73 (m, 2H), 2.36 (m, 1H), 2.05 (m, 1H), 1.13 (t, J=6.9 Hz, 3H), and 1.05 (t, J=7.2 Hz, 6H). (one proton ($ArCH_aH_bC(C=O)$) overlapped with water)). MS (ESI) positive ion 410 (M+H)$^+$; negative ion 408 (M−H)$^−$.

Example 9

Isobutyl 2-(((4-(diethylamino)phenyl)amino)carbonyl)-1,2,3,4-tetrahydronaphthalen-2-ylcarbamate The titled compound was prepared according to the procedure described in Example 8B, substituting i-butyl chloroformate for ethyl chloroformate used in Example 8B. $^1$H NMR (300 MHz, DMSO-$D_6$) δ 9.14 (s, 1H), 7.32 (d, J=8.7 Hz, 2H), 7.08 (m, 4H), 7.08 (s, 1H), 6.61 (d, J=9.3 Hz, 2H), 3.73 (m, 2H), 3.28 (q, J=6.6 Hz, 4H), 3.03 (d, J=16.5 Hz, 1H), 2.73 (m, 2H), 2.36 (m, 1H), 2.09 (m, 1H), 1.79 (septet, J=6.6 Hz, 1H), 1.05 (t, J=6.9 Hz, 6H), and 0.85 (d, J=6.6 Hz, 6H). (one proton ($ArCH_aH_bC(C=O)$) overlapped with water)). MS (ESI) positive ion 438 (M+H)$^+$; negative ion 436 (M−H)$^−$.

Example 10

Benzyl 2-(((4-(diethylamino)phenyl)amino)carbonyl)-1,2,3,4-tetrahydronaphthalen-2-ylcarbamate The titled compound was prepared according to the procedure described in Example 8B, substituting benzyl chloroformate for ethyl chloroformate used in Example 8B. $^1$H NMR (300 MHz, DMSO-$D_6$) δ 9.17 (s, 1H), 7.32 (d, J=8.7 Hz, 2H), 7.31 (m, 6H), 7.08 (s, 4H), 6.61 (d, J=9.3 Hz, 2H), 5.04 (d, J=12.9 Hz, 1H), 4.81 (d, J=12.9 Hz, 1H), 3.28 (q, J=6.6 Hz, 4H), 3.07 (d, J=16.2 Hz, 1H), 2.73 (m, 2H), 2.36 (m, 1H), 2.05 (m, 1H), and 1.06 (t, J=7.2 Hz, 6H). (one proton ($ArCH_aH_bC(C=O)$) overlapped with water)). MS (ESI) positive ion 472 (M+H)$^+$.

Example 11 tert-Butyl 2-(((4-(diethylamino)phenyl)amino)carbonyl)-1,2,3,4-tetrahydronaphthalen-2-yl(methyl)carbamate

Example 11A 2-(tert-Butoxycarbonyl-methyl-amino)-1,2,3,4-tetrahydro-naphthalene-2-carboxylic acid To 2-tert-butoxycarbonylamino-1,2,3,4-tetrahydro-naphthalene-2-carboxylic acid (291 mg, 1.0 mmol) in DMF (2.0 mL) was added MeI (710 mg, 5.0 mmol) and NaH (50%, 250 mg, 5.0 mmol) at 0° C. Ethyl acetate (50 mL) was added after 3 days and the mixture was washed with water (3×15 mL). The material (380 mg) was taken up in methanol (5.0 mL) and water (3.0 mL) and NaOH (10 M, 3.0 mL) was added. After 2 days, 10% HCl was added to adjust the pH~2 and the mixture was extracted with ethyl acetate (3×20 mL). The organic layers were concentrated in vacuo to provide the titled acid.

Example 11B tert-Butyl 2-(((4-(diethylamino)phenyl)amino)carbonyl)-1,2,3,4-tetrahydronaphthalen-2-yl(methyl)carbamate Example 11A was dissolved in DMF (2.0 mL) followed by addition of N,N-diethyl-benzene-1,4-diamine sulfate (262 mg, 1.0 mmol), $Et_3N$ (505 mg, 5.0 mmol), and TBTU (321 mg, 1.0 mmol) at ambient temperature. After 16 hours the mixture was concentrated under reduced pressure and purified by column chromatography to provide the titled compound (180 mg, 40% over 3 steps). $^1$H NMR (300 MHz, DMSO-$D_6$) δ 9.05 (s, 1H), 7.34 (d, J=8.7 Hz, 2H), 7.08 (m, 4H), 6.60 (d, J=9.0 Hz, 2H), 3.34 (d, J=16.8 Hz, 1H), 3.27 (d, J=6.6 Hz, 1H), 2.96 (d, J=16.8 Hz, 1H), 2.83 (s, 3H), 2.67 (t, J=6.6 Hz, 2H), 2.27 (m, 2H), 1.32 (s, 9H), and 1.05 (t, J=7.2 Hz, 6H). MS (ESI) positive ion 452 (M+H)$^+$.

Example 12

Methyl 2-(((4-(diethylamino)-2-methylphenyl)amino)carbonyl)-8-methoxy-1,2,3,4-tetrahydronaphthalene-2-carboxylate

Example 12A

8-Methoxy-3,4-dihydro-1H-naphthalene-2,2-dicarboxylic acid methyl ester

A THF (1.0 mL) solution of 8-methoxy-1,2,3,4-tetrahydro-naphthalene-2-carboxylic acid methyl ester (660 mg, 3.0 mmol) was added to freshly made LDA (made by addition of 2.0 mL of 2.3 M BuLi to 1.5 mL THF solution of 0.7 mL $iPr_2NH$ at −78° C. and the mixture was allowed to stir for 1.5 hour. A $CO_2$ balloon was then applied. The reaction mixture was quenched with aqueous $NH_4Cl$ and the resulting mixture was extracted with ethyl acetate (3×15 mL). The combined organic extracts were dried over $MgSO_4$ and concentrated under reduced pressure to provide the crude-8-methoxy-3,4-dihydro-1H-naphthalene-2,2-dicarboxylic acid methyl ester (470 mg).

Example 12B

Methyl 2-(((4-(diethylamino)-2-methylphenyl)
amino)carbonyl)-8-methoxy-1,2,3,4-tetrahydronaph-
thalene-2-carboxylate The crude acid from Example 12A (180 mg) was dissolved in DMF (1.5 mL) and N',N'-diethyl-2-methyl-1,4-phenylenediamine monohydrogenchloride (150 mg, 0.7 mmol), Et$_3$N (202 mg, 2.0 mmol), and TBTU (225 mg, 0.7 mmol) were added at ambient temperature. The mixture was stirred overnight and purified by column chromatography to provide the titled compound (120 mg, 25% over 2 steps). $^1$H NMR (300 MHz, DMSO-D$_6$) δ 8.94 (s, 1H), 7.06 (t, J=7.8 Hz, 2H), 6.83 (d, J=9.0 Hz, 1H), 6.75 (d, J=8.1 Hz, 1H), 6.67 (d, J=7.8 Hz, 1H), 6.43 (m, 2H), 3.78 (s, 3H), 3.67 (s, 3H), 3.29 (q, J=6.9 Hz, 4H), 3.09 (s, 2H), 2.73 (m, 2H), 2.30 (m, 2H), 1.99 (s, 3H), and 1.05 (t, J=6.6 Hz, 6H). MS (ESI) positive ion 425 (M+H)$^+$; negative ion 423 (M–H)$^-$.

Example 13

N-(4-(Diethylamino)phenyl)-2-((N-isopropylglycyl)
amino)-1,2,3,4-tetrahydronaphthalene-2-carboxam-
ide

Example 13A 2-(2-Amino-acetylamino)-1,2,3,4-tetrahydro-naph-
thalene-2-carboxylic acid (4-diethylamino-phenyl)-
amide To a mixture of 2-amino-1,2,3,4-tetrahydro-naphthalene-2-carboxylic acid (4-diethylamino-phenyl)-amide (100 mg, 0.3 mmol) from Example 8 and N-Boc-glycine (52 mg, 0.3 mmol) in DMF (1.0 mL) was added Et$_3$N (61 mg, 0.6 mmol) and TBTU (96 mg, 0.3 mmol). The mixture was stirred overnight and the precipitates were collected by filtration (130 mg) and dissolved in dichloromethane (10 mL) and TFA (5.0 mL). The mixture was concentrated under reduced pressure and ethyl acetate (20 mL) were added and the resulting solution was washed with 1N NaOH. The organic phase was dried over MgSO$_4$ and then concentrated under reduced pressure to give 2-(2-amino-acetylamino)-1,2,3,4-tetrahydro-naphthalene-2-carboxylic acid (4-diethylamino-phenyl)-amide (70 mg).

Example 13B

N-(4-(Diethylamino)phenyl)-2-((N-isopropylglycyl)
amino)-1,2,3,4-tetrahydronaphthalene-2-carboxam-
ide The amine from Example 13A was dissolved in 1 M pH4 MeOH buffer (82 g NaOAc/L MeOH, add HOAc to pH 4.5) and acetone (12 mg, 0.2 mmol) and NaBH$_3$CN (13 mg, 0.2 mmol) were added. Following stirring for 2 hours ethyl acetate (30 mL) was added and the resulting solution was washed with aqueous NaOH (1N, 2×10 mL). The organic phase was dried over MgSO$_4$, concentrated, and purified by HPLC to provide the titled compound (30 mg, 23% over 3 steps). $^1$H NMR (300 MHz, DMSO-D$_6$) δ 9.21 (s, 1H), 7.83 (s, 1H), 7.32 (d, J=9.3 Hz, 2H), 7.10 (m, 4H), 6.61 (d, J=9.0 Hz, 2H), 3.28 (q, J=6.9 Hz, 4H), 3.22 (d, J=18.9 Hz, 1H), 3.11 (d, J=18.9 Hz, 1H), 3.07 (s, 2H), 2.77 (m, 2H), 2.45 (m, 2H), 2.09 (m, 1H), 1.05 (t, J=7.2 Hz, 6H), 0.81 (d, J=6.3 Hz, 3H), 0.73 (d, J=6.3 Hz, 3H). MS (ESI) positive ion 437 (M+H)$^+$; negative ion 435 (M–H)$^-$.

Example 14 tert-Butyl 8-bromo-2-(((4-(diethylamino)phenyl)
amino)carbonyl)-1,2,3,4-tetrahydronaphthalen-2-
ylcarbamate

Example 14A

8-Bromo-2-tert-butoxycarbonylamino-1,2,3,4-tet-
rahydro-naphthalene-2-carboxylic acid 2-Amino-8-bromo-1,2,3,4-tetrahydro-naphthalene-2-carboxylic acid hydrochloride (180 mg, 0.5 mmol), prepared according to the procedure described in literature (*J. Med. Chem;* 1995, 38, 4056–4069), was suspended in dioxane (3 mL). 1N NaOH (1.5 mL) was added to make a clear solution. Di-tert-butyl dicarbonate (120 mg, 0.55 mmol) was added and the reaction mixture was stirred at room temperature for 48 hours. The mixture was diluted with ethyl acetate and 1N HCL, the organic phase was washed with brine, dried (MgSO$_4$), filtered, concentrated to provide the titled compound as a brown solid. MS (ESI(–)) m/e 368, 370 (M–H)$^+$; $^1$H NMR (300 MHz, DMSO-d$_6$) δ 12.5 (bs, 1H), 7.43–7.37 (m, 1H), 7.24 (s, 1H), 7.13–7.02 (m, 2H), 3.12–2.62 (m, 4H), 1.95–1.78 (m, 2H), 1.36 (s, 9).

Example 14B (8-Bromo-2-(4-diethylamino-phenylcarbamoyl)-1,2,
3,4-tetrahydro-naphthalen-2-yl)-carbamic acid tert-
butyl ester The titled compound was prepared according to the procedure described in Example 1, substituting the acid from Example 14A for 8-methoxy-1,2,3,4-tetrahydro-naphthalene-2-carboxylic acid used in Example 1. MS (ESI(+)) m/e 516, 518 (M+H)$^+$; $^1$H NMR (300 MHz, DMSO-d$_6$) δ 9.20 (s, 1H), 7.42 (d, J=7.5 Hz, 1H), 7.32 (d, J=8.7 Hz, 2H), 7.12 (d, J=7.5 Hz, 1H), 7.06 (t, J=7.5 Hz, 1H), 6.92 (s, 1H), 6.61 (d, J=9.0 Hz, 2H), 3.28 (q, J=6.9 Hz, 4H), 3.02–2.66 (m, 4H), 2.38–1.98 (m, 2H), 1.36 (s, 9H), 1.05 (t, J=6.9 Hz, 6H).

Example 15

Isobutyl 2-(((4-(diethylamino)phenyl)amino)carbo-
nyl)-1,2,3,4-tetrahydronaphthalen-2-yl(methyl)car-
bamate The titled compound was prepared according to the procedure described in Example 33A–G, substituting 1,2,3,4-tetrahydro-naphthalene-2-carboxylic acid for 8-methoxy-1,2,3,4-tetrahydro-naphthalene-2-carboxylic acid used in Example 33A. $^1$H NMR (300 MHz, DMSO-D$_6$) δ 9.07 (s, 1H), 7.29 (d, J=9.0 Hz, 2H), 7.08 (m, 4H), 6.59 (d, J=9.0 Hz, 2H), 3.75 (d, J=5.7 Hz, 2H), 3.28 (q, J=7.5 Hz, 4H), 3.03 (d, J=17.1 Hz, 1H), 2.87 (s, 3H), 2.68 (t, J=6.3 Hz, 2H), 2.38 (m, 1H), 2.22 (m, 1H), 1.80 (septet, J=6.3 Hz, 1H), 1.05 (t, J=7.2 Hz, 6H), and 0.85 (d, J=6.6 Hz, 6H). (one proton (Ar-CH$_a$H$_b$C(=O)) overlapped with water)). MS (ESI) positive ion 452 (M+H)$^+$.

Example 16

Isobutyl 2-(((4-(diethylamino)phenyl)amino)carbonyl)-1,2,3,4-tetrahydronaphthalene-2-carboxylate

Example 16A 2-(4-Diethylamino-phenylcarbamoyl)-1,2,3,4-tetrahydro-naphthalene-2-carboxylic acid tert-butyl ester The titled compound was prepared according to the procedure described in Example 1, substituting 3,4-dihydro-1H-naphthalene-2,2-dicarboxylic acid tert-butyl ester from Example 43A for 8-methoxy-1,2,3,4-tetrahydro-naphthalene-2-carboxylic acid used in Example 1.

Example 16B 2-(4-Diethylamino-phenylcarbamoyl)-1,2,3,4-tetrahydro-naphthalene-2-carboxylic acid The t-butyl ester from Example 16A was dissolved in 4 N HCl in dioxane (1.0 mL) and the resulting mixture was stirred at ambient temperature for 4 hours. The mixture was concentrated under reduced pressure to provide the titled compound.

Example 16C

Isobutyl 2-(((4-(diethylamino)phenyl)amino)carbonyl)-1,2,3,4-tetrahydronaphthalene-2-carboxylate The titled compound was prepared according to the procedure described in Example 1, substituting 2-(4-diethylamino-phenylcarbamoyl)-1,2,3,4-tetrahydro-naphthalene-2-carboxylic acid for 8-methoxy-1,2,3,4-tetrahydro-naphthalene-2-carboxylic acid, and isobutyl alcohol for N,N-diethylphenylene diamine sulfate used in Example 1. $^1$H NMR (400 MHz, DMSO-D$_6$) δ 9.20 (s, 1H), 7.28 (d, J=8.8 Hz, 2H), 7.09 (m, 4H), 6.58 (d, J=8.8 Hz, 2H), 3.85 (m, 2H), 3.27 (overlapped with H$_2$O, 6H), 2.76 (m, 2H), 2.35 (m, 2H), 1.83 (m, 1H), 1.04 (t, J=7.2 Hz, 6H), 0.81 (d, J=6.4 Hz, 3H), and 0.80 (t, J=6.4 Hz, 3H). MS (ESI) positive ion 423 (M+H)$^+$; negative ion 421 (M−H)$^−$.

Example 17

3-Methylbutyl 2-(((4-(diethylamino)phenyl)amino)carbonyl)-1,2,3,4-tetrahydronaphthalene-2-carboxylate The titled compound was prepared according to the procedure described in Example 1, substituting 2-(4-diethylamino-phenylcarbamoyl)-1,2,3,4-tetrahydro-naphthalene-2-carboxylic acid from Example 16B for 8-methoxy-1,2,3,4-tetrahydro-naphthalene-2-carboxylic acid, and neopentyl alcohol for N,N-diethylphenylene diamine sulfate used in Example 1. $^1$H NMR (400 MHz, DMSO-D$_6$) δ 9.18 (s, 1H), 7.28 (d, J=9.2 Hz, 2H), 7.07 (m, 4H), 6.58 (d, J=9.2 Hz, 2H), 4.08 (t, J=6.4 Hz, 2H), 3.27 (q, J=7.2 Hz, 4H), 3.26 (s, 2H), 2.76 (m, 2H), 2.32 (m, 2H), 1.54 (m, 1H), 1.41 (q, J=6.0 Hz, 2H), 1.04 (t, J=6.8 Hz, 6H), 0.81 (d, J=6.8 Hz, 3H), and 0.79 (t, J=6.8 Hz, 3H). MS (ESI) positive ion 437 (M+H)$^+$; negative ion 435 (M−H)$^−$.

Example 18

Methyl N-((2-(((4-(diethylamino)phenyl)amino)carbonyl)-1,2,3,4-tetrahydronaphthalen-2-yl)carbonyl)valinate The titled compound was prepared according to the procedure described in Example 1, substituting 2-(4-diethylamino-phenylcarbamoyl)-1,2,3,4-tetrahydro-naphthalene-2-carboxylic acid from Example 16B for 8-methoxy-1,2,3,4-tetrahydro-naphthalene-2-carboxylic acid, and valine methyl ester hydrochloride for N,N-diethylphenylene diamine sulfate used in Example 1. MS (ESI) (M+H)$^+$ 480.

Example 19

2-Fluoroethyl 2-(((4-(diethylamino)phenyl)amino)carbonyl)-1,2,3,4-tetrahydronaphthalen-2-ylcarbamate The titled compound was prepared according to the procedure described in Example 8B, substituting 2-fluoroethyl chloroformate for ethyl chloroformate used in Example 8B. $^1$H NMR (300 MHz, DMSO-D$_6$) δ 9.15 (s, 1H), 7.32 (d, J=9.3 Hz, 2H), 7.32 (s, 1H), 7.08 (m, 4H), 6.61 (d, J=9.3 Hz, 2H), 4.54 (dt, J=47.7, 4.2 Hz, 2H), 4.17 (m, 2H), 3.28 (q, J=6.9 Hz, 4H), 3.05 (d, J=17.4 Hz, 1H), 2.73 (m, 2H), 2.36 (m, 1H), 2.09 (m, 1H), and 1.05 (t, J=6.9 Hz, 6H). (one proton (ArCH$_a$H$_b$C(C=O)) overlapped with water)). MS (ESI) positive ion 428 (M+H)$^+$.

Example 20

Neopentyl 2-(((4-(diethylamino)phenyl)amino)carbonyl)-1,2,3,4-tetrahydronaphthalen-2-ylcarbamate The titled compound was prepared according to the procedure described in Example 8B, substituting 2-neopentyl chloroformate for ethyl chloroformate used in Example 8B. $^1$H NMR (300 MHz, DMSO-D$_6$) δ 9.13 (s, 1H), 7.32 (d, J=9.0 Hz, 2H), 7.09 (m, 4H), 7.08 (s, 1H), 6.60 (d, J=9.0 Hz, 2H), 3.79 (d, J=10.5 Hz, 1H), 3.61 (d, J=10.5 Hz, 1H), 3.31 (d, J=18.0 Hz, 1H), 3.28 (q, J=6.9 Hz, 4H), 3.05 (d, J=18.0 Hz, 1H), 2.74 (m, 2H), 2.36 (m, 1H), 2.09 (m, 1H), 1.05 (t, J=7.2 Hz, 6H), and 0.86 (s, 9H). (one proton (ArCH$_a$H$_b$C(C=O)) overlapped with water)). MS (ESI) positive ion 452 (M+H)$^+$; negative ion 450 (M−H)$^−$.

Example 21

3-Chloropropyl 2-(((4-(diethylamino)phenyl)amino)carbonyl)-1,2,3,4-tetrahydronaphthalen-2-ylcarbamate The titled compound was prepared according to the procedure described in Example 8B, substituting 3-chloropropyl chloroformate for ethyl chloroformate used in Example 8B. $^1$H NMR (300 MHz, DMSO-D$_6$) δ 9.17 (s, 1H), 7.32 (d, J=9.0 Hz, 2H), 7.16 (s, 1H), 7.09 (m, 4H), 6.60 (d, J=9.3 Hz, 2H), 4.04 (m, 2H), 3.67 (t, J=6.3 Hz, 2H), 3.31 (d, J=18.0 Hz, 1H), 3.28 (q, J=6.9 Hz, 4H), 3.05 (d, J=15.9 Hz, 1H), 2.74 (m, 2H), 2.36 (m, 1H), 2.11 (m, 1H), 1.96 (quintet, J=6.6 Hz, 2H), and 1.05 (t, J=6.9 Hz, 6H). MS (ESI) positive ion 458 (M+H)$^+$, 460 (M+H)$^+$; negative ion 456 (M−H)—, 458 (M−H)$^−$.

Example 22

But-3-enyl 2-(((4-(diethylamino)phenyl)amino)carbonyl)-1,2,3,4-tetrahydronaphthalen-2-ylcarbamate The titled compound was prepared according to the procedure described in Example 8B, substituting 3-butenyl chloroformate for ethyl chloroformate used in Example 8B. $^1$H NMR (300 MHz, DMSO-$D_6$) δ 9.12 (s, 1H), 7.32 (d, J=9.3 Hz, 2H), 7.08 (m, 4H), 7.08 (s, 1H), 6.60 (d, J=9.0 Hz, 2H), 5.76 (dddd, J=6.9, 6.9, 10.2, 17.1 Hz, 1H), 5.05 (dm, J=17.1 Hz, 1H), 5.00 (dm, J=9.6 Hz, 1H), 3.97 (m, 2H), 3.28 (q, J=6.9 Hz, 4H), 3.05 (d, J=16.8 Hz, 1H), 2.73 (m, 2H), 2.36 (m, 1H), 2.27 (q, J=6.6 Hz, 2H), 2.09 (m, 1H), and 1.05 (t, J=6.9 Hz, 6H). (one proton (ArCH$_a$H$_b$C(C=O)) overlapped with water)). MS (ESI) positive ion 436 (M+H)$^+$; negative ion 434 (M−H)$^−$.

Example 23

Hexyl 2-(((4-(diethylamino)phenyl)amino)carbonyl)-1,2,3,4-tetrahydronaphthalen-2-ylcarbamate The titled compound was prepared according to the procedure described in Example 8B, substituting n-hexyl chloroformate for ethyl chloroformate used in Example 8B. $^1$H NMR (300 MHz, DMSO-$D_6$) δ 9.13 (s, 1H), 7.32 (d, J=8.7 Hz, 2H), 7.08 (m, 4H), 7.08 (s, 1H), 6.60 (d, J=9.0 Hz, 2H), 3.92 (m, 2H), 3.28 (q, J=6.9 Hz, 4H), 3.04 (d, J=18.0 Hz, 1H), 2.74 (m, 2H), 2.36 (m, 1H), 2.07 (m, 1H), 1.45 (m, 2H), 1.22 (m, 6H), 1.05 (t, J=7.2 Hz, 6H), and 0.83 (t, J=6.9 Hz, 3H). (one proton (ArCH$_a$H$_b$C(C=O)) overlapped with water)). MS (ESI) positive ion 466 (M+H)$^+$; negative ion 464 (M−H)$^−$.

Example 24

But-3-ynyl 2-(((4-(diethylamino)phenyl)amino)carbonyl)-1,2,3,4-tetrahydronaphthalen-2-ylcarbamate The titled compound was prepared according to the procedure described in Example 8B, substituting 3-butynyl chloroformate for ethyl chloroformate used in Example 8B. $^1$H NMR (300 MHz, DMSO-$D_6$) δ 9.13 (s, 1H), 7.32 (d, J=9.0 Hz, 2H), 7.25 (s, 1H), 7.08 (m, 4H), 6.61 (d, J=9.0 Hz, 2H), 3.79 (d, J=10.5 Hz, 1H), 4.00 (m, 2H), 3.28 (q, J=6.9 Hz, 4H), 3.04 (d, J=17.4 Hz, 1H), 2.82 (t, J=2.4 Hz, 1H), 2.74 (m, 2H), 2.43 (dt, J=2.4, 6.6 Hz, 2H), 2.36 (m, 1H), 2.09 (m, 1H), and 1.05 (t, J=6.6 Hz, 6H). (one proton (ArCH$_a$H$_b$C(C=O)) overlapped with water)). MS (ESI) positive ion 434 (M+H)$^+$; negative ion 432 (M−H)$^−$.

Example 25

Allyl 2-(((4-(diethylamino)phenyl)amino)carbonyl)-1,2,3,4-tetrahydronaphthalen-2-ylcarbamate The titled compound was prepared according to the procedure described in Example 8B, substituting allyl chloroformate for ethyl chloroformate used in Example 8B. $^1$H NMR (300 MHz, DMSO-$D_6$) δ 9.15 (s, 1H), 7.32 (d, J=9.3 Hz, 2H), 7.22 (s, 1H), 7.08 (m, 4H), 6.61 (d, J=9.3 Hz, 2H), 5.76 (dddd, J=5.1, 5.1, 10.5, 17.1 Hz, 1H), 5.27 (dm, J=17.1 Hz, 1H), 5.14 (dm, J=10.2 Hz, 1H), 4.44 (m, 2H), 3.28 (q, J=6.6 Hz, 4H), 3.05 (d, J=16.5 Hz, 1H), 2.73 (m, 1H), 2.36 (m, 1H), 2.09 (m, 1H), and 1.05 (t, J=6.6 Hz, 6H). (one proton (ArCH$_a$H$_b$C(C=O)) overlapped with water)). MS (ESI) positive ion 422 (M+H)$^+$; negative ion 420 (M−H)$^−$.

Example 26

Butyl 2-(((4-(diethylamino)phenyl)amino)carbonyl)-1,2,3,4-tetrahydronaphthalen-2-ylcarbamate The titled compound was prepared according to the procedure described in Example 8B, substituting n-butyl chloroformate for ethyl chloroformate used in Example 8B. $^1$H NMR (300 MHz, DMSO-$D_6$) δ 9.14 (s, 1H), 7.32 (d, J=9.0 Hz, 2H), 7.08 (m, 4H), 7.08 (s, 1H), 6.60 (d, J=9.3 Hz, 2H), 3.93 (m, 2H), 3.28 (q, J=6.6 Hz, 4H), 3.04 (d, J=16.8 Hz, 1H), 2.73 (m, 2H), 2.34 (m, 1H), 2.08 (m, 1H), 1.48 (m, 2H), 1.30 (m, 2H), 1.05 (t, J=6.9 Hz, 6H), and 0.84 (t, J=6.6 Hz, 3H). (one proton (ArCH$_a$H$_b$C(C=O)) overlapped with water)). MS (ESI) positive ion 438 (M+H)$^+$; negative ion 436 (M−H)$^−$.

Example 27

Propyl 2-(((4-(diethylamino)phenyl)amino)carbonyl)-1,2,3,4-tetrahydronaphthalen-2-ylcarbamate The titled compound was prepared according to the procedure described in Example 8B, substituting n-propyl chloroformate for ethyl chloroformate used in Example 8B. $^1$H NMR (500 MHz, DMSO-$D_6$) δ 9.12 (s, 1H), 7.32 (d, J=9.5 Hz, 2H), 7.08 (m, 4H), 7.06 (s, 1H), 6.61 (d, J=9.0 Hz, 2H), 3.89 (m, 2H), 3.28 (q, J=7.0 Hz, 4H), 3.04 (d, J=17.0 Hz, 1H), 2.73 (m, 2H), 2.36 (m, 1H), 2.08 (m, 1H), 1.51 (sextet, J=7.0 Hz, 2H), 1.05 (t, J=6.5 Hz, 6H), and 0.85 (t, J=7.5 Hz, 3H). (one proton (ArCH$_a$H$_b$C(C=O)) overlapped with water)). MS (ESI) positive ion 424 (M+H)$^+$; negative ion 422 (M−H)$^−$.

Example 28

But-2-ynyl 2-(((4-(diethylamino)phenyl)amino)carbonyl)-1,2,3,4-tetrahydronaphthalen-2-ylcarbamate The titled compound was prepared according to the procedure described in Example 8B, substituting 2-butynyl chloroformate for ethyl chloroformate used in Example 8B. $^1$H NMR (300 MHz, DMSO-$D_6$) δ 9.14 (s, 1H), 7.32 (d, J=9.0 Hz, 2H), 7.08 (m, 4H), 7.08 (s, 1H), 6.61 (d, J=9.3 Hz, 2H), 4.55 (m, 2H), 3.28 (q, J=6.6 Hz, 4H), 3.04 (d, J=17.7 Hz, 1H), 2.73 (m, 2H), 2.34 (m, 1H), 2.08 (m, 1H), 1.77 (s, 3H), and 1.05 (t, J=7.2 Hz, 6H). (one proton (ArCH$_a$H$_b$C(C=O)) overlapped with water)). MS (ESI) positive ion 434 (M+H)$^+$.

Example 29

N$^2$-(4-(Diethylamino)phenyl)-(N$^1$,N$^1$-dimethylglycinamide)-3,4-dihydronaphthalene-2,2(1H)-dicarboxamide The titled compound was prepared according to the procedure described in Example 1, substituting 2-(4-diethylamino-phenylcarbamoyl)-1,2,3,4-tetrahydro-naphthalene-2-carboxylic acid from Example 16B for 8-methoxy-1,2,3,4-tetrahydro-naphthalene-2-carboxylic acid, and 2-amino-N,N-dimethyl-acetamide for N,N-diethylphenylene diamine sulfate used in Example 1. $^1$H NMR (300 MHz, DMSO-$D_6$) δ 9.70 (s, 1H), 8.21 (t, J=5.4 Hz, 1H), 7.46 (t, J=9.0 Hz, 2H), 7.01–7.09 (m, 4H), 6.60 (d, J=9.0 Hz, 1H), 3.92 (d, J=5.7 Hz, 2H), 3.28 (q, J=6.9 Hz, 4H), 3.20 (d, J=17.4 Hz, 1H), 2.95 (s, 3H), 2.87 (s, 3H), 2.78 (m, 2H), 2.30 (m, 2H), and 1.05 (t, J=6.9 Hz, 6H). (one proton (ArCH$_a$H$_b$C(C=O)) overlapped with water)). MS (ESI) positive ion 451 (M+H)$^+$; negative ion 449 (M–H)$^-$.

Example 30

Pentyl 2-(((4-(diethylamino)phenyl)amino)carbonyl)-1,2,3,4-tetrahydronaphthalen-2-ylcarbamate The titled compound was prepared according to the procedure described in Example 8B, substituting n-pentyl chloroformate for ethyl chloroformate used in Example 8B. $^1$H NMR (300 MHz, DMSO-D$_6$) δ 9.14 (s, 1H), 7.32 (d, J=9.0 Hz, 2H), 7.08 (m, 4H), 7.08 (s, 1H), 6.60 (d, J=9.3 Hz, 2H), 3.92 (m, 2H), 3.28 (q, J=7.2 Hz, 4H), 3.04 (d, J=17.4 Hz, 1H), 2.73 (m, 2H), 2.36 (m, 1H), 2.07 (m, 1H), 1.50 (m, 2H), 1.24 (m, 4H), 1.05 (t, J=6.6 Hz, 6H), and 0.82 (t, J=6.0 Hz, 3H). (one proton (ArCH$_a$H$_b$C(C=O)) overlapped with water)). MS (ESI) positive ion 452 (M+H)$^+$; negative ion 450 (M–H)$^-$.

Example 31

Isobutyl 2-(((4-(diethylamino)phenyl)amino)carbonyl)-8-methoxy-1,2,3,4-tetrahydronaphthalen-2-ylcarbamate Example 31A 2-Isobutoxycarbonylamino-8-methoxy-1,2,3,4-tetrahydro-naphthalene-2-carboxylic acid The titled compound was prepared according to the procedure described in Example 33A–D and F, substituting 2-isobutoxycarbonylamino-1,2,3,4-tetrahydro-naphthalene-2-carboxylic acid tert-butyl ester from Example 33D for 2-(isobutoxycarbonyl-methyl-amino)-1,2,3,4-tetrahydro-naphthalene-2-carboxylic acid tert-butyl ester used in Example 33F.

Example 31B

Isobutyl 2-(((4-(diethylamino)phenyl)amino)carbonyl)-8-methoxy-1,2,3,4-tetrahydronaphthalen-2-ylcarbamate The titled compound was prepared according to the procedure described in Example 1, substituting 2-isobutoxycarbonylamino-8-methoxy-1,2,3,4-tetrahydro-naphthalene-2-carboxylic acid from Example 31A for 8-methoxy-1,2,3, 4-tetrahydro-naphthalene-2-carboxylic acid used in Example 1. $^1$H NMR (400 MHz, DMSO-D$_6$) δ 9.14 (s, 1H), 7.33 (d, J=9.2 Hz, 2H), 7.07 (t, J=8.0 Hz, 1H), 7.01 (s, 1H), 6.75 (d, J=8.0 Hz, 1H), 6.69 (d, J=7.6 Hz, 1H), 6.61 (d, J=8.8 Hz, 2H), 3.76 (s, 3H), 3.71 (m, 2H), 3.27 (q, J=7.2 Hz, 4H), 3.03 (d, J=17.6 Hz, 1H), 2.96 (d, J=17.2 Hz, 1H), 2.68 (m, 2H), 2.35 (m, 1H), 2.00 (m, 1H), 1.80 (septet, J=6.8 Hz, 1H), 1.05 (t, J=6.8 Hz, 6H), and 0.86 (d, J=6.8 Hz, 6H). MS (ESI) positive ion 468 (M+H)$^+$; negative ion 466 (M–H)$^-$.

Example 32

Isobutyl 2-(((4-(diethylamino)-2-methylphenyl)amino)carbonyl)-8-methoxy-1,2,3,4-tetrahydronaphthalen-2-ylcarbamate The titled compound was prepared according to the procedure described in Example 1, substituting 2-isobutoxycarbonylamino-8-methoxy-1,2,3,4-tetrahydro-naphthalene-2-carboxylic acid from Example 31A for 8-methoxy-1,2,3, 4-tetrahydro-naphthalene-2-carboxylic acid, and N',N'-diethyl-2-methyl-1,4-phenylenediamine monohydrogenchloride for N,N-diethylphenylene diamine sulfate used in Example 1. $^1$H NMR (400 MHz, DMSO-D$_6$) δ 8.70 (s, 1H), 7.15 (s, 1H), 7.07 (t, J=8.0 Hz, 1H), 7.01 (d, J=8.0 Hz, 1H), 6.75 (d, J=8.0 Hz, 1H), 6.69 (d, J=8.0 Hz, 1H), 6.48 (s, 1H), 6.46 (d, J=8.8 Hz, 1H), 3.76 (s, 3H), 3.71 (m, 2H), 3.29 (q, J=6.8 Hz, 4H), 3.05 (d, J=20.0 Hz, 1H), 2.99 (d, J=18.8 Hz, 1H), 2.71 (m, 2H), 2.50 (s, 3H), 2.37 (m, 1H), 2.00 (m, 1H), 1.82 (septet, J=6.8 Hz, 1H), 1.06 (t, J=7.2 Hz, 6H), and 0.87 (d, J=6.8 Hz, 6H). MS (ESI) positive ion 482 (M+H)$^+$; negative ion 480 (M–H)$^-$.

Example 33

Isobutyl 2-(((4-(diethylamino)phenyl)amino)carbonyl)-8-methoxy-1,2,3,4-tetrahydronaphthalen-2-yl(methyl)carbamate Example 33A 8-Methoxy-1,2,3,4-tetrahydro-naphthalene-2-carboxylic acid methyl ester To a DMF solution (30 mL) of 8-methoxy-1,2,3,4-tetrahydro-naphthalene-2-carboxylic acid (5.0 g, 24 mmol) was added MeI (7.1 g, 50 mmol) and K$_2$CO$_3$ (6.9 g, 50 mmol). The mixture was allowed to stir overnight and ethyl acetate (200 mL) was added. The resulting solution was washed with water (3×50 mL) and brine (50 mL) to provide 8-methoxy-1,2,3,4-tetrahydro-naphthalene-2-carboxylic acid methyl ester (6.6 g).

Example 33B 8-methoxy-3,4-dihydro-1H-naphthalene-2,2-dicarboxylic acid tert-butyl ester methyl ester A THF solution of Example 33A was added to freshly made LDA (made by addition of 16 mL 2.2 M BuLi to a 35 µL THF solution of 3.6 g iPr$_2$NH at –78° C.) at –78° C. BoC$_2$O (7.8 g, 36 mmol) in THF (10 mL). The mixture was stirred for 2 hour followed by the addition of aqueous NH$_4$Cl. The solution was extracted with ethyl acetate (3×75 mL). The combined organic layers were dried with MgSO$_4$, filtered, concentrated under reduced pressure and purified by column chromatography purification to provide 8-methoxy-3,4-dihydro-1H-naphthalene-2,2-dicarboxylic acid tert-butyl ester methyl ester (4.7 g, 61% over two steps).

Example 33C

8-Methoxy-3,4-dihydro-1H-naphthalene-2,2-dicarboxylic acid tert-butyl ester

The methyl ester from Example 33B was dissolved in a mixture of MeOH (10 mL) and water (2.0 mL) followed by addition of LiOH monohydrate (1.9 g, 45 mmol). The mixture was stirred for 18 hours after which 10% HCl was added until pH=4 was achieved. This mixture was extracted with ethyl acetate (2×50 mL). The combined organic layers were dried with $MgSO_4$, filtered, concentrated under reduced pressure to provide the titled compound (4.3 g).

Example 33D

2-Isobutoxycarbonylamino-1,2,3,4-tetrahydro-naphthalene-2-carboxylic acid tert-butyl ester This crude material was dissolved in THF (40 mL) followed by addition of $Et_3N$ (2.02 g, 20 mmol) and $(PhO)_2PON_3$ (3.8 g, 14 mmol) at 0° C. The volatiles were removed under reduced pressure after 2 hours. A portion (6.0 g out of 8.3 g) was dissolved in isobutyl alcohol and heated to 115° C. for 1.5 hours. The volatiles were removed under reduced pressure and the residue was purified by column chromatography to give 2-isobutoxycarbonylamino-1,2,3,4-tetrahydro-naphthalene-2-carboxylic acid tert-butyl ester (2.9 g, 79% over two steps).

Example 33E 2-(Isobutoxycarbonyl-methyl-amino)-1,2,3,4-tetrahydro-naphthalene-2-carboxylic acid tert-butyl ester The carbamate from Example 33D (1.5 g, 4.3 mmol) was dissolved in DMF (4.0 mL) followed by addition of MeI (1.1 g, 8.0 mmol) and NaH (50%, 384 mg, 8.0 mmol) at 0° C. The mixture was stirred for 6 hours, diluted with aqueous $NH_4Cl$ and extracted with ethyl acetate(3×75 mL). The combined organic layers were dried with $MgSO_4$, filtered, concentrated under reduced pressure to provide the titled compound (1.3 g, 83%).

Example 33F 2-(Isobutoxycarbonyl-methyl-amino)-8-methoxy-1,2,3,4-tetrahydro-naphthalene-2-carboxylic acid The t-butyl ester from Example 33E was dissolved in 4 N HCl in dioxane (10 mL) and the resulting mixture was stirred at r.t for 16 h and at 60° C. for 1.5 h. The volatiles were removed to give the titled acid.

Example 33G isobutyl 2-(((4-(diethylamino)-2-methylphenyl)amino)carbonyl)-8-methoxy-1,2,3,4-tetrahydronaphthalen-2-ylcarbamate The acid from Example 33F was dissolved in DMF (6.0 mL). N,N-diethyl-benzene-1,4-diamine sulfate (786 mg, 3.0 mmol), $Et_3N$ (1.0 g, 10 mmol), and TBTU (963 mg, 3.0 mmol) were added and the resulting mixture was stirred overnight and purified by column chromatography to provide the titled compound (680 mg, 40% over two steps). $^1H$ NMR (400 MHz, DMSO-$D_6$) δ 9.07 (s, 1H), 7.30 (d, J=8.4 Hz, 2H), 7.07 (t, J=7.6 Hz, 1H), 6.77 (d, J=8.0 Hz, 1H), 6.68 (d, J=7.2 Hz, 1H), 6.60 (d, J=8.8 Hz, 2H), 3.78 (s, 3H), 3.76 (m, 2H), 3.27 (q, J=6.8 Hz, 4H), 3.12 (d, J=17.6 Hz, 1H), 2.87 (d, J=16.0 Hz, 1H), 2.85 (s, 3H), 2.64 (m, 2H), 2.32 (d, 1H), 2.19 (m, 1H), 1.80 (m, 1H), 1.05 (t, J=6.8 Hz, 6H), and 0.85 (d, J=6.4 Hz, 6H). MS (ESI) positive ion 482 $(M+H)^+$.

Example 34

Isobutyl 2-(((4-(diethylamino)-2-methylphenyl)amino)carbonyl)-8-methoxy-1,2,3,4-tetrahydronaphthalen-2-yl(methyl)carbamate The titled compound was prepared according to the procedure described in Example 33G, substituting N',N'-diethyl-2-methyl-1,4-phenylenediamine monohydrogenchloride for N,N-diethyl-benzene-1,4-diamine sulfate used in Example 33G. $^1H$ NMR (300 MHz, DMSO-$D_6$) δ 8.71 (s, 1H), 7.07 (t, J=7.8 Hz, 1H), 6.90 (d, J=8.4 Hz, 1H), 6.76 (d, J=8.4 Hz, 1H), 6.70 (d, J=7.5 Hz, 1H), 6.47 (s, 1H), 6.46 (d, J=8.1 Hz, 1H), 3.79 (m, 2H), 3.78 (s, 3H), 3.28 (q, J=6.9 Hz, 4H), 3.16 (d, J=17.4 Hz, 1H), 2.90 (d, J=18.9 Hz, 1H), 2.85 (s, 3H), 2.70 (m, 2H), 2.40 (m, 1H), 2.20 (m, 1H), 2.08 (s, 3H), 1.85 (septet, J=6.3 Hz, 1H), 1.06 (t, J=6.9 Hz, 6H), and 0.88 (d, J=6.9 Hz, 6H). MS (ESI) positive ion 496 $(M+H)^+$.

Example 35

Isobutyl 8-bromo-2-(((4-(diethylamino)phenyl)amino)carbonyl)-1,2,3,4-tetrahydronaphthalen-2-ylcarbamate

Example 35A

8-Bromo-2-isobutoxycarbonylamino-1,2,3,4-tetrahydro-naphthalene-2-carboxylic acid The titled compound was prepared according to the procedure described in Example 53A–C, substituting 8-bromo-β-tetralone for β-tetralone used in Example 53A.

Example 35

Isobutyl 8-bromo-2-(((4-(diethylamino)phenyl)amino)carbonyl)-1,2,3,4-tetrahydronaphthalen-2-ylcarbamate The titled compound was prepared according to the procedure described in Example 1, substituting 8-bromo-2-isobutoxycarbonylamino-1,2,3,4-tetrahydro-naphthalene-2-carboxylic acid for 8-methoxy-1,2,3,4-tetrahydro-naphthalene-2-carboxylic acid used in Example 1. MS (ESI(+)) m/e 516, 518 $(M+H)^+$; $^1H$ NMR (300 MHz, DMSO-$d_6$) δ 9.22 (s, 1H), 7.42 (d, J=7.7 Hz, 1H), 7.33 (d, J=9.2 Hz, 2H), 7.23 (s, 1H), 7.12 (d, J=7.7 Hz, 1H), 7.06 (t, J=7.5 Hz, 1H), 6.61 (d, J=9.0 Hz, 2H), 3.80–3.69 (m, 2H), 3.28 (q, J=6.9 Hz, 4H), 3.08–2.66 (m, 4H), 2.38–2.02 (m, 2H), 1.87–1.75 (m, 1H), 1.05 (t, J=6.8 Hz, 6H), 0.87 (d, J=6.8 Hz, 6H).

Example 36

Isobutyl-8-chloro-2-(((4-(diethylamino)phenyl)amino)carbonyl)-1,2,3,4-tetrahydronaphthalen-2-ylcarbamate

Example 36A

8-Chloro-2-isobutoxycarbonylamino-1,2,3,4-tetrahydro-naphthalene-2-carboxylic acid The titled compound was prepared according to the procedure described in Example 53A–C, substituting 8-chloro-β-tetralone for β-tetralone used in Example 53A.

Example 36B

Isobutyl-8-chloro-2-(((4-(diethylamino)phenyl)amino)carbonyl)-1,2,3,4-tetrahydronaphthalen-2-ylcarbamate The titled compound was prepared according to the procedure described in Example 1, substituting 8-chloro-2-isobutoxycarbonylamino-1,2,3,4-tetrahydro-naphthalene-2-carboxylic acid for 8-methoxy-1,2,3,4-tetrahydro-naphthalene-2-carboxylic acid used in Example 1. MS (ESI(+)) m/e 472 (M+H)$^+$; $^1$H NMR (300 MHz, DMSO-d$_6$) δ 9.23 (s, 1H), 7.33 (d, J=9.2 Hz, 2H), 7.28–7.08 (m, 4H), 6.61 (d, J=9.2 Hz, 2H), 3.80–3.69 (m, 2H), 3.28 (q, J=6.9 Hz, 4H), 3.08–2.66 (m, 4H), 2.41–2.02 (m, 2H), 1.87–1.75 (m, 1H), 1.05 (t, J=6.8 Hz, 6H), 0.87 (d, J=6.8 Hz, 6H).

Example 37

Neopentyl-8-chloro-2-(((4-(diethylamino)phenyl)amino)carbonyl)-1,2,3,4-tetrahydronaphthalen-2-ylcarbamate

Example 37A

8-Chloro-2-(2,2-dimethyl-propoxycarbonylamino)-1,2,3,4-tetrahydro-naphthalene-2-carboxylic acid The titled compound was prepared according to the procedure described in Example 53A–C, substituting 8-chloro-β-tetralone for β-tetralone used in Example 53A, and neopentyl chloroformate for the isobutyl chloroformate used in Example 53C.

Example 37B

Neopentyl-8-chloro-2-(((4-(diethylamino)phenyl)amino)carbonyl)-1,2,3,4-tetrahydronaphthalen-2-ylcarbamate The titled compound was prepared according to the procedure described in Example 1, substituting 8-chloro-2-(2,2-dimethyl-propoxycarbonylamino)-1,2,3,4-tetrahydro-naphthalene-2-carboxylic acid for 8-methoxy-1,2,3,4-tetrahydro-naphthalene-2-carboxylic acid used in Example 1. MS (ESI(+)) m/e 486 (M+H)$^+$; $^1$H NMR (300 MHz, DMSO-d$_6$) δ 9.23 (s, 1H), 7.33 (d, J=8.8 Hz, 2H), 7.28–7.08 (m, 4H), 6.60 (d, J=9.1 Hz, 2H), 3.73–3.61 (m, 2H), 3.28 (q, J=6.9 Hz, 4H), 3.08–2.66 (m, 4H), 2.41–2.02 (m, 2H), 1.05 (t, J=6.8 Hz, 6H), 0.87 (s, 9H).

Example 38

Neopentyl-8-chloro-2-(((4-(diethylamino)-2-methylphenyl)amino)carbonyl)-1,2,3,4-tetrahydronaphthalen-2-ylcarbamate The titled compound was prepared according to the procedure described in Example 1, substituting 8-chloro-2-(2,2-dimethyl-propoxycarbonylamino)-1,2,3,4-tetrahydro-naphthalene-2-carboxylic acid from Example 37A for 8-methoxy-1,2,3,4-tetrahydro-naphthalene-2-carboxylic acid, and N,N-Diethy-2-methyl-1,4-phenylenediamine for N,N-Diethy-1,4-phenylenediamine used in Example 1. MS (ESI(+)) m/e 500 (M+H)$^+$; $^1$H NMR (300 MHz, DMSO-d$_6$) δ 8.81 (s, 1H), 7.40–6.96 (m, 5H), 6.50–6.43 (m, 2H), 3.74–3.63 (m, 2H), 3.28 (q, J=6.9 Hz, 4H), 3.08–2.66 (m, 4H), 2.41–2.02 (m, 2H), 2.09 (s, 3H), 106 (t, J=6.8 Hz, 6H), 0.89 (s, 9H).

Example 39

Isobutyl-8-chloro-2-(((4-(diethylamino)phenyl)amino)carbonyl) 1,2,3,4-tetrahydronaphthalen-2-yl(methyl)carbamate The titled compound was prepared according to the procedure described in Example 53A–G, substituting 8-chloro-β-tetralone for β-tetralone used in Example 53A, and methyl iodide for iodoethane used in Example 53E. MS (ESI(+)) m/e 486 (M+H); $^1$H NMR (300 MHz, DMSO-d$_6$) δ 9.19 (s, 1H), 7.28 (d, J=9.2 Hz, 2H), 7.29–7.04 (m, 3H), 6.59 (d, J=9.2 Hz, 2H), 3.85–3.69 (m, 2H), 3.53, 3.47 (s, s, 1H), 3.28 (q, J=6.9 Hz, 4H), 2.83–2.52 (m, 3H), 2.94 (s, 3H), 2.31–2.03 (m, 2H), 1.87–1.75 (m, 1H), 1.04 (t, J=6.8 Hz, 6H), 0.86 (d, J=6.8 Hz, 6H).

Example 40

Isobutyl-2-(((4-(dibutylamino)phenyl)amino)carbonyl)-1,2,3,4-tetrahydronaphthalen-2-ylcarbamate

Example 40A

Dibutyl-(4-nitro-phenyl)-amine

To a solution of 4-nitroaniline (1.4 g, 10 mmol) in 1,2-dichloroethane (10 ml) at 0° C. was added butyraldehyde (1.8 g, 25 mmol). The reaction mixture was stirred for 0.5 hour, then sodium triacetoxyborohydride (5.3 g, 25 mmol) and acetic acid (1 ml) was added. The reaction mixture was stirred at room temperature for 2 hours. Solvent were removed under reduced pressure and the residue purified on column of silica gel to provide the titled 4-nitro-N,N-dibutylaniline (1.1 g, 44%) as a yellow solid. $^1$HNNMR (CDCl$_3$, 300 MHz), δ ppm 8.10 and 6.58 (d, J=9 Hz, 4H, Ar—H), 3.36 (t, J=9.0 Hz, 4H, 2 NCH$_2$), 1.6 (m, 4H, 2CH$_2$), 1.48 (m, 4H, 2CH$_2$), 0.98 (t, 6H, 2CH$_3$), MS (ESI) (M+1)$^+$ 251.

Example 40B

N,N-Dibutyl-benzene-1,4-diamine

To a solution of 4-nitro-N,N-dibutylaniline from Example 40A (1.0 g, 4.0 mmol) in methanol (10 ml) was added palladium 10 wt % on activated carbon (85 mg, 0.08 mmol) under an atmosphere of hydrogen. The reaction mixture was stirred at room temperature for 4 hours and filtered through celite. After solvent were removed under reduced pressure, the titled material was obtained as a white solid, which was used in next step without purification.

Example 40C

Isobutyl-2-(((4-(dibutylamino)phenyl)amino)carbonyl)-1,2,3,4-tetrahydronaphthalen-2-ylcarbamate The titled compound was prepared according to the procedure described in Example 1, substituting 2-isobutoxycarbonylamino-1,2,3,4-tetrahydro-naphthalene-2-carboxylic acid from Example 53C for 8-methoxy-1,2,3,4-tetrahydro-naphthalene-2-carboxylic acid, and N,N-dibutylbenzene-1,4-diamine from Example 40B for N,N-diethylphenylene diamine sulfate used in Example 1. $^1$HNNMR (CDCl$_3$, 300 MHz), δ 8.30 (b, 1H, NH), 7.14 and 6.60 (d, J=3 Hz, 4H, Ar—H), 7.15–7.11 (m, 4H, Ar—H), 5.05 (b, 1H, NH), 3.85 (d, J=3 Hz, 2H, CH$_2$),3.45 and 3.01 (d, J=9 Hz, 2H, CH$_2$), 3.24 (t, J=4.5 Hz, 4H, 2CH$_2$), 2.91–2.81 (m, 2H, CH$_2$), 2.57, 2.25 (m, 2H, CH$_2$), 1.86 (m, 1H, CH), 1.53 (m, 4H, 2CH$_2$), 1.33 (m, 4H, 2CH$_2$), 0.94 (t, J=4.5 Hz, 6H, 2CH$_3$), 0.88 (d, J=3 Hz, 6H, 2 CH$_3$). MS (ESI) (M+1)$^+$ 494, (M−1)$^+$ 492.

Example 41

Isobutyl-2-(((4-(2,4-diamino-6-ethylpyrimidin-5-yl) phenyl)amino) carbonyl)-1,2,3,4-tetrahydronaphtha-len-2-ylcarbamate The titled compound was prepared according to the procedure described in Example 1, substituting 2-isobutoxy-carbonylamino-1,2,3,4-tetrahydro-naphthalene-2-carboxy-lic acid from Example 53C for 8-methoxy-1,2,3,4-tetrahy-dro-naphthalene-2-carboxylic acid, and 6-ethyl-5-(4-amino-phenyl)-pyrimidine-2,4-diamine (De Graw et al: J. Org. Chem. 1961, 26, 1933–1937) for N,N-diethylphenylene diamine sulfate used in Example 1. $^1$HNNMR (DMSO-d$_6$, 300 MHz), δ 9.58 (b, 1H, NH), 7.16 (b, 1H, NH), 7.79 and 7.09 (d, J=6 Hz, 4H, Ar—H), 7.10 (m, 4H, Ar—H), 5.80 (b, 2H, NH$_2$), 5.41 (b, 2H, NH$_2$), 3.74 (m, 2H, OCH$_2$), 3.37, 3.33, 3.09 and 3.04 (AB, J=12 Hz, CH$_2$), 2.76 (m, 2H, CH$_2$), 2.37 and 2.15 (m, 2H, CH$_2$), 2.12 (q, J=6.0 Hz, 2H, CH$_2$), 1.80 (m, 1H, CH), 0.96 (t, J=6.0 Hz, 3H, CH$_3$), 0.86 (d, J=3 Hz, 6H, 2CH$_3$). MS (ESI) (M+1)$^+$ 503.2, (M−1)$^+$ 501.2.

Example 42

Isobutyl-6-bromo-2-(((4-(diethylamino)phenyl) amino)carbonyl)-1,2,3,4-tetrahydronaphthalen-2-ylcarbamate Example 42A 6-Bromo-2-isobutoxycarbonylamino-1,2,3,4-tetrahy-dro-naphthalene-2-carboxylic acid The titled compound was prepared according to the procedure described in Example 53A–C, substituting 6-bromo-β-tetralone for β-tetralone used in Example 53A.

Example 42B

Isobutyl-6-bromo-2-(((4-(diethylamino)phenyl) amino)carbonyl)-1,2,3,4-tetrahydronaphthalen-2-ylcarbamate The titled compound was prepared according to the procedure described in Example 1, substituting 6-bromo-2-isobutoxycarbonylamino-1,2,3,4-tetrahydro-naphthalene-2-carboxylic acid from Example 42A for 8-methoxy-1,2,3,4-tetrahydro-naphthalene-2-carboxylic acid used in Example 1. $^1$HNNMR (DMSO-d6, 300 MHz), δ 9.13 (b, 1H, NH), 7.11 (b, 1H, NH), 7.31 and 6.60 (AB, J=6 Hz, 4H, Ar—H), 7.30 (s, 1H, Ar—H), 7.27 and 7.03 (AB, J=6 Hz, 2H, Ar—H), 3.74 (m, 2H, OCH$_2$), 3.28 (q, J=3.0 Hz, 4H, 2NCH$_2$), 3.25 and 3.01 (AB, J=12 Hz, 2H, CH$_2$), 2.75 (m, 2H, CH$_2$), 2.33 and 2.08 (m, 2H, CH$_2$), 1.79 (m, 1H, CH), 1.05 (t, J=3.0 Hz, 6H, 2CH$_3$), 0.85 (d, J=3 Hz, 6H, 2 CH$_3$). MS (ESI) (M+1)$^+$ 518, (M−1)$^+$ 516.

Example 43

2-Methyl-2-nitropropyl-2-(((4-(diethylamino)phe-nyl)amino)carbonyl)-1,2,3,4-tetrahydronaphthalen-2-ylcarbamate Example 43A 3,4-Dihydro-1H-naphthalene-2,2-dicarboxylic acid tert-butyl ester To a THF solution (40 mL) of iPr$_2$NH (7.6 g, 75 mmol) was added n-BuLi (2.2 M, 34 mL, 75 mmol) at −78° C. A THF solution (15 mL) of 1,2,3,4-tetrahydro-naphthalene-2-carboxylic acid methyl ester was added to the freshly made LDA solution at −78° C. BOC$_2$O (16.5 g, 75 mmol) in THF (10 mL) was added after 45 minutes and the mixture was stirred for 3 hours after which aqueous NH$_4$Cl was added and extracted with ethyl acetate (3×75 mL) The combined organic layers were dried with MgSO$_4$, filtered, concentrated under reduced pressure to provide the titled compound. The material was dissolved in methanol (30 mL) and water (5 mL) followed by addition of LiOH monohydrate (6.1 g, 150 mmol). The mixture was stirred for 18 hours followed by the addition of 10% HCl until pH=3 was achieved. This mixture was extracted with ethyl acetate (3×50 mL). The combined organic layers were dried with MgSO$_4$, filtered, concentrated under reduced pressure to provide the titled compound to provide the titled compound (16 g).

Example 43B

2-Azidocarbonyl-1,2,3,4-tetrahydro-naphthalene-2-carboxylic acid tert-butyl ester 3,4-Dihydro-1H-naphthalene-2,2-dicarboxylic acid tert-butyl ester from Example 43A was dissolved in THF (50 mL) followed by addition of Et$_3$N (5.05 g, 50 mmol) and (PhO)$_2$PON$_3$ (11 g, 40 mmol) at 0° C. After 3 hours the volatiles were removed under reduced pressure and the residue purified by column chromatography to provide the titled compound (13.1 g, 58% over three steps).

Example 43C 2-(2-Methyl-2-nitro-propoxycarbonylamino)-1,2,3,4-tetrahydro-naphthalene-2-carboxylic acid The azide from Example 43B (230 mg, 0.76 mmol) was dissolved in toluene (0.5 mL) and 2-methyl-2-nitro-propan-1-ol (182 mg, 1.52 mmol) was added. The mixture was heated to 115° C. for 16 hours. The volatiles were removed under reduced pressure, the residue dissolved in 4 N HCl in dioxane (1.0 mL) and the resulting mixture was stirred at ambient temperature for 4 hours. The volatiles were removed under reduced pressure to provide the titled compound.

Example 43D

2-Methyl-2-nitropropyl-2-(((4-(diethylamino)phe-nyl)amino)carbonyl)-1,2,3,4-tetrahydronaphthalen-2-ylcarbamate The acid from Example 43C was dissolved in DMF (1.0 mL). N,N-Diethyl-benzene-1,4-diamine sulfate (131 mg, 0.5 mmol), Et₃N (202 mg, 2.0 mmol), and TBTU (160 mg, 0.5 mmol) were added and the resulting mixture was stirred overnight and purified by column chromatography to provide the titled compound (110 mg, 30% over 3 steps). $^1$H NMR (300 MHz, DMSO-D$_6$) δ 9.12 (s, 1H), 7.36 (s, 1H), 7.32 (d, J=9.3 Hz, 2H), 7.08 (m, 4H), 6.61 (d, J=9.3 Hz, 2H), 4.38 (d, J=12.0 Hz, 1H), 4.28 (d, J=12.3 Hz, 1H), 3.28 (q, J=6.9 Hz, 4H), 3.02 (d, J=15.0 Hz, 1H), 2.73 (m, 2H), 2.36 (m, 1H), 2.09 (m, 1H), 1.52 (s, 6H), and 1.05 (t, J=7.2 Hz, 6H). (one proton (ArCH$_a$H$_b$C(C=O)) overlapped with water)). MS (ESI) positive ion 483 (M+H)⁺.

Example 44

Isobutyl-6-((1E)-3-amino-3-oxoprop-1-enyl)-2-(((4-(diethylamino) phenyl)amino)carbonyl)-1,2,3,4-tetrahydronaphthalen-2-ylcarbamate To a 10 ml pressure tube, the bromide from Example 42B (125 mg, 0.24 mmol), palladium(II)acetate (2.7 mg, 0.012 mmol), tri-o-tolylphosphine (110 mg, 0.36 mmol), acrylamide (34 mg, 048 mmol), triethylamine (0.12 ml, 0.8 mmol) and DMF (2 ml) were added. After purging with nitrogen, the reaction mixture was heated at 110° C. for overnight. The reaction mixture was partitioned between methylene chloride and water. The organic layer was washed with brine and concentrated under reduced pressure. The residue was purified on column of silica gel to provide the titled compound (115 mg, 95%) as a white solid. $^1$HNNMR (DMSO-d6, 300 MHz), δ 9.13 (b, 1H, NH), 7.45 and 7.30 (b, 2H, NH$_2$), 7.01 (b, 1H, NH), 7.36, 7.32, 6.56 and 6.52 (AB, J=12 Hz, 2H, CH=CH), 7.32, 7.30, 6.61 and 6.58 (AB, 4H, J=9 Hz, Ar—H), 3.76–3.66 (m, 2H, OCH$_2$), 3.27 (q, J=3.0 Hz, 4H, 2NCH$_2$), 3.33, 3.29, 3.07 and 3.03 (AB, J=12 Hz, 2H, CH$_2$), 2.80–2.71 (m, 2H, CH$_2$), 2.35 and 2.09 (m, 2H, CH$_2$), 1.79 (m, H, CH), 1.04 (t, J=3.0 Hz, 6H, 2CH$_3$), 0.84 (d, J=6.0 Hz, 6H, 2 CH$_3$). MS (ESI) (M+1)⁺ 507, (M−1)⁺ 505.

Example 45

Isobutyl-2-(((4-(diethylamino)phenyl)amino)carbonyl)-6-methoxy-1,2,3,4-tetrahydronaphthalen-2-ylcarbamate

Example 45A

2-Isobutoxycarbonylamino-6-methoxy-1,2,3,4-tetrahydro-naphthalene-2-carboxylic acid The titled compound was prepared according to the procedure described in Example 53A–C, substituting 6-methoxy-β-tetralone for β-tetralone used in Example 53A.

Example 45B

Isobutyl-2-(((4-(diethylamino)phenyl)amino)carbonyl)-6-methoxy-1,2,3,4-tetrahydronaphthalen-2-ylcarbamate The titled compound was prepared according to the procedure described in Example 1, substituting 2-isobutoxycarbonylamino-6-methoxy-1,2,3,4-tetrahydro-naphthalene-2-carboxylic acid from Example 45A for 8-methoxy-1,2,3,4-tetrahydro-naphthalene-2-carboxylic acid. White solid. 1HNNMR (DMSO-d$_6$, 300 MHz), δ 9.09 (b, 1H, NH), 7.32, 7.30, 6.61 and 6.59 (AB, J=6 Hz, 4H, Ar—H), 6.95 (d, J=6.0 Hz, 2H, Ar—H), 6.68 (d, J=6.0 Hz, 1H, Ar—H), 6.65 (b, 1H, NH), 3.74 (m, 2H, OCH$_2$), 3.69 (s, OCH$_3$), 3.27 (q, J=6.0 Hz, 4H, 2NCH$_2$), 3.18, 3.14, 3.00 and 2.96 (AB, J=12 Hz, 2H, CH$_2$), 2.71 (m, 2H, CH$_2$), 2.35 and 2.06 (m, 2H, CH$_2$), 1.78 (m, H, CH), 1.04 (t, J=6.0 Hz, 6H, 2CH$_3$), 0.84 (d, J=3.0 Hz, 6H, 2 CH$_3$). MS (ESI) (M+1)⁺ 468, (M−1)⁺ 466.

Example 46

2-(Dimethylamino)-2-methylpropyl-2-(((4-(diethylamino)phenyl)amino)carbonyl)-1,2,3,4-tetrahydronaphthalen-2-ylcarbamate To 2-methyl-2-nitropropyl-2-(((4-(diethylamino)phenyl) amino)carbonyl)-1,2,3,4-tetrahydronaphthalen-2-ylcarbamate from Example 43 (100 mg) in MeOH (40 mL) was added 10% Pd/C (20 mg). A hydrogen balloon was then applied and the reaction mixture was stirred at ambient temperature for 3 days. Pd/c was filtered off and the filtrate was concentrated under reduced pressure and purified by reverse phase HPLC to give the titled compound (25 mg, 25%). $^1$H NMR (500 MHz, DMSO-D$_6$) δ 9.09 (s, 1H), 7.32 (d, J=9.0 Hz, 2H), 7.09 (m, 4H), 7.05 (s, 1H), 6.61 (d, J=9.5 Hz, 2H), 3.99 (d, J=11.0 Hz, 1H), 3.81 (d, J=12.5 Hz, 1H), 3.28 (q, J=7.0 Hz, 4H), 3.07 (d, J=17.0 Hz, 1H), 2.74 (m, 2H), 2.40 (m, 1H), 2.14 (s, 6H), 2.09 (m, 1H), 1.05 (t, J=7.0 Hz, 6H), and 0.94 (s, 6H). (one proton (ArCH$_a$H$_b$C(C=O)) overlapped with water)). MS (ESI) positive ion 481 (M+H)⁺.

Example 47

Tetrahydrofuran-2-ylmethyl-2-(((4-(diethylamino) phenyl)amino)carbonyl)-1,2,3,4-tetrahydronaphthalen-2-ylcarbamate To a cold solution (0° C.) of tetrahydro-2-furanmethanol (0.013 mL, 0.13 mmol) in toluene:methylene chloride (1:1, 0.03 mL) was added triphosgene (30 mg, 0.1 mmol) and quinoline (0.018 mL, 0.15 mmole) at 0° C. The reaction mixture was allowed to warm to room temperature and stirred overnight. The reaction was cooled at 0° C., diluted with 3 N HCl and extracted with ethyl acetate twice. The combined organic layer was washed with brine, dried over sodium sulfate, filtered and concentrated under reduced pressure. The cold (−40° C.) solution of crude chloroformate (0.075 mmol) in anhydrous tetrahydrofuran (0.5 mL) was added to amine from Example 8A (17 mg, 0.05 mmol) and pyridine (0.009 mL, 0.105 mmole) in anhydrous tetrahydrofuran (0.1 mL) at −40° C. The reaction mixture was allowed to warm at room temperature, stirred overnight and concentrated under reduced pressure. The residue was purified by reverse-phase HPLC to provide the titled compound.

Yield: 12.7 mg (44%). $^1$H NMR (500 MHz, DMSO-d$_6$) δ 1.05 (m, 6H), 1.51 (m, 1H), 1.76 (m, 3H), 2.07 (m, 1H), 2.36 (s, 1H), 2.49 (m, 1H), 2.72 (m, 2H), 3.05 (d, J=16.53 Hz, 1H), 3.25 (m, 4H), 3.58 (m, 1H), 3.69 (m, 1H), 3.93 (m, 3H), 6.60 (d, J=9.04 Hz, 2H), 7.06 (m, 4H), 7.18 (s, 1H), 7.32 (d, J=9.04 Hz, 2H), 9.09 (s, 1H); MS (ESI): 466 (M+H)⁺, 464 (M−H)⁻.

Example 48

Pyridin-3-ylmethyl-2-(((4-(diethylamino)phenyl) amino)carbonyl)-1,2,3,4-tetrahydronaphthalen-2-ylcarbamate The titled compound was prepared according to the same procedure as in Example 47, substituting the tetrahydro-2- furanmethanol used in Example 47 with pyridine-3-methanol (14.2 mg, 0.13 mmol). Yield: 3.9 mg (8%). $^1$H NMR (500 MHz, DMSO-$d_6$) δ 1.05 (t, J=7.02 Hz, 6H), 2.07 (m, 1H), 2.35 (s, 1H), 2.49 (m, 1H), 2.75 (m, 2H), 3.06 (m, J=17.15 Hz, 1H), 3.28 (m, 4H), 5.06 (m, 2H), 6.61 (m, 2H), 7.08 (m, 4H), 7.29 (d, J=8.42 Hz, 2H), 7.42 (d, J=9.04 Hz, 1H), 7.71 (s, 1H), 8.52 (d, J=30.88 Hz, 1H), 9.16 (s, 1H); MS (ESI): 473 (M+H)$^+$.

Example 49

Isopropyl-2-(((4-(diethylamino)phenyl)amino)carbonyl)-1,2,3,4-tetrahydronaphthalen-2-ylcarbamate The isopropyl chloroformate (18.4 mg, 0.15 mmol) was dissolved in anhydrous tetrahydrofuran (0.05 mL) and cooled at −40° C. A solution of amine from Example 8A (33.7 mg, 0.1 mmol) and triethylamine (0.021 mL, 0.15 mmol) in anhydrous tetrahydrofuran (0.5 mL) was added at −40° C. and reaction allowed to warm at room temperature, shaken overnight, then concentrated under reduced pressure. The residue was purified by reverse-phase HPLC to provide the title compound. Yield: 10.7 mg (25%). $^1$H NMR (500 MHz, DMSO-$d_6$) δ 1.05 (m, 12H), 2.11 (m, 1H), 2.33 (d, J=17.15 Hz, 1H), 2.50 (m, 1H), 2.73 (m, 2H), 2.99 (d, J=16.53 Hz, 1H), 3.44 (m, 4H), 4.70 (m, 1H), 7.07 (m, 4H), 7.67 (d, J=15.0 Hz, 4H), 9.88 (s, 1H), 10.95 (s, 1H); MS (ESI): 424 (M+H)$^+$, 422 (M−H)$^-$.

Example 50

2-Chloroethyl-2-(((4-(diethylamino)phenyl)amino)carbonyl)-1,2,3,4-tetrahydronaphthalen-2-ylcarbamate The titled compound was prepared according to the same procedure as in Example 49, substituting the isopropyl chloroformate used in Example 49 with 2-chloroethyl chloroformate (19 mg, 0.15 mmol). Yield: 35.1 mg (79%). $^1$H NMR (500 MHz, DMSO-$d_6$) δ 1.04 (m, 6H), 2.12 (s, 1H), 2.47 (m, 2H), 2.74 (m, 2H), 3.03 (d, J=16.84 Hz, 1H), 3.44 (m, 4H), 3.74 (s, 2H), 4.19 (m, 2H), 7.06 (m, 4H), 7.67 (m, 4H), 9.88 (s, 1H), 10.95 (s, 1H); MS (ESI): 444 (M+H)$^+$, 442 (M−H)$^-$.

Example 51

2-Bromoethyl-2-(((4-(diethylamino)phenyl)amino)carbonyl)-1,2,3,4-tetrahydronaphthalen-2-ylcarbamate The titled compound was prepared according to the same procedure as in Example 49, substituting the isopropyl chloroformate used in Example 49 with 2-bromoethyl chloroformate (28.1 mg, 0.15 mmol). Yield: 31.6 mg (65%). $^1$H NMR (500 MHz, DMSO-$d_6$) δ 1.04 (m, 6H), 2.12 (s, 1H), 2.35 (d, J=3.74 Hz, 1H), 2.49 (m, 1H), 2.74 (m, 2H), 3.03 (d, J=16.53 Hz, 1H), 3.45 (m, 6H), 4.26 (m, 2H), 7.09 (m, 4H), 7.50 (s, 3H), 7.82 (s, 2H), 9.87 (s, 1H), 10.93 (s, 1H); MS (ESI): 488 (M+H)$^+$, 486 (M−H)$^-$.

Example 52

2-Methoxyethyl-2-(((4-(diethylamino)phenyl)amino)carbonyl)-1,2,3,4-tetrahydronaphthalen-2-ylcarbamate The titled compound was prepared according to the same procedure as in Example 49, substituting the isopropyl chloroformate used in Example 49 with 2-methoxyethyl chloroformate (20.8 mg, 0.15 mmol). Yield: 7.9 mg (18%). $^1$H NMR (500 MHz, DMSO-$d_6$) δ 1.05 (m, 6H), 2.10 (s, 1H), 2.35 (s, 1H), 2.50 (m, 1H), 2.74 (m, 2H), 3.02 (d, J=16.84 Hz, 1H), 3.43 (m, 7H), 4.04 (m, 2H), 4.18 (m, 2H), 7.08 (m, 4H), 7.59 (m, 4H), 9.88 (s, 1H), 10.93 (s, 1H); MS (ESI): 440 (M+H)$^+$, 438 (M−H)$^-$.

Example 53

Isobutyl-2-(((4-(diethylamino)phenyl)amino)carbonyl)-1,2,3,4-tetrahydronaphthalen-2-yl(ethyl)carbamate

Example 53A

Dihydrospiro(imidazolidine-4,2'(1'H)-naphthalene)-2,5-dione

A stirred slurry of β-tetralone (3.3 mL, 25 mmol), sodium cyanide (1.84 g, 37.5 mmol), ammonium carbonate (14.26 g), absolute ethanol (50 mL) and water (50 mL) was heated to 80° C. for 48 hours. After cooling to room temperature, the reaction mixture was poured onto ice and stirred for 2 hours. The resulting precipitate was filtered and rinsed with water and dried under vacuum to provide the titled compound (5.28 g, 98%). $^1$H NMR (δ, DMSO-$d^6$): 10.68 (s, 1H), 8.29 (s, 1H), 7.06–7.13 (m, 4H), 3.14 (d, 1H), 2.88–3.08 (m, 2H), 2.74 (d, 1H), 1.89–1.99 (m, 1H), 1.78–1.84 (m, 1H). MS (DCI/NH$_3$): 234.1 (M+1).

Example 53B

2-Amino-1,2,3,4-tetrahydro-naphthalene-2-carboxylic acid

A stirred slurry of hydantoin (2.16 g, 10 mmol), barium hydroxide (8.57 g, 50 mmol) and water (200 mL) was heated to 125° C. for 24 hours, cooled to room temperature over 2 hours and the pH adjusted to 1 with 4 N H$_2$SO$_4$. The resulting slurry was heated to 100° C. for 1 hour, cooled to room temperature, filtered, and washed with water to collect BaSO$_4$. The remaining liquid was concentrated to half volume under reduced pressure and the pH adjusted to 8 with ammonium hydroxide. The titled compound, which crystallized from solution, was collected and washed with water to provide a white solid (1.86 g, 97%). $^1$H (δ, DMSO-$d^6$): 7.04–7.12 (m, 4H), 3.33 (br. s, 4H), 2.74–2.80 (m, 2H), 2.68 (s, 1H), 2.02–2.12 (m, 1H), 1.79–1.85 (m, 1H). MS (DCI/NH$_3$): 192.1 (M+1).

Example 53C

2-Isobutoxycarbonylamino-1,2,3,4-tetrahydro-naphthalene-2-carboxylic acid

To an ice cooled solution of amino acid from Example 53B (248 mg, 1.3 mmol) and anhydrousl, 4-dioxane (6 mL) was added isobutyl chloroformate (0.23 mL, 1.69 mmol). The solution's pH was maintained at 11 using 2M NaOH. The reaction was allowed to warm to room temperature. After 1 hour the reaction was complete. The pH was adjusted to 2 with 2 M HCl and extracted with ethyl acetate. The combined organic layers were washed with brine, dried over Na$_2$SO$_4$, filtered and concentrated in vacuo to provide the titled compound as a sticky white solid (341 mg, 90%). $^1$H (δ, DMSO-$d^6$): 12.45 (br s, 1H), 7.39 (s, 1H), 7.03–7.15 (m, 4H), 3.6–3.8 (m, 2H), 3.1–3.2 (m, 2H), 3.07 (d, 1H), 2.71 (br s, 1H), 2.25 (br s, 1H), 1.9–2.0 (m, 1H), 1.77–1.9 (m, 1H). MS (DCI/NH$_3$): 292.1 (M+1), 309.2 (M+H+NH$_4^+$).

Example 53D

2-Isobutoxycarbonylamino-1,2,3,4-tetrahydro-naphthalene-2-carboxylic acid methyl ester To a stirred solution of acid from Example 53D (341 mg, 1.17 mmol) and anhydrous N,N-dimethylforamide (3 mL) under N$_2$ was added potassium carbonate (245 mg, 1.76 mmol), then iodomethane (0.15 mL, 2.34 mmol). After 1.5 hour at room temperature, the reaction was complete by TLC. The reaction was poured into 10% aq. K$_2$CO$_3$ and extracted with diethyl ether. The combined organic phases were washed with brine and dried over Na$_2$SO$_4$, filtered and concentrated in vacuo to yield an off-white sticky solid (317 mg, 88%).

$^1$H NMR (d, DMSO-d6): 7.95 (s, 1H), 7.01–7.11 (m, 4H), 3.67–3.77 (m, 2H), 3.62 (s, 3H), 3.21 (d, 1H), 3.06 (d, 1H), 2.76–2.86 (m, 1H), 2.69–2.71 (m, 1H), 2.25 (br s, 1H), 1.91–2.01 (m, 1H), 1.75–1.84 (m, 1H), 0.86 (d, 6H). MS (DCI/NH$_3$): 306.1 (M+1).

Example 53E 2-(Ethyl-isobutoxycarbonyl-amino)-1,2,3,4-tetrahydro-naphthalene-2-carboxylic acid methyl ester To an ice cooled solution of ester from Example 53D (101 mg, 0.33 mmol) and anhydrous N,N-dimethylforamide (1.5 mL) under N$_2$ was added 60% dispersion sodium hydride (35 mg, 0.825 mmol) and then stirred for 15 minutes. Iodoethane (40 µL, 0.495 mmol) was added. The reaction was stirred at room temperature for 18 hours, diluted with water and extracted with ethyl acetate. The combined organic layers were washed with brine, dried over Na$_2$SO$_4$, filtered and concentrated under reduced pressure. The crude product was purified by silica gel column (20% ethyl acetate/hexane) to provide the titled compound as a clear, colorless syrup (51 mg, 46%). $^1$H NMR (δ, CDCl$_3$): 7.07–7.15 (m, 4H), 3.90 (dd, 2H), 3.71 (s, 3H), 3.35–3.5 (m, 2H), 3.00–3.08 (m, 2H), 7.75–2.8 (m, 2H), 2.55–2.6 (m, 1H), 2.19–2.3 (m 1H), 1.88–2.0 (m, 1H), 1.14 (t, 3H), 0.95 (d, 6H). MS (DCI/NH$_3$): 334.2 (M+1).

Example 53F 2-(Ethyl-isobutoxycarbonyl-amino)-1,2,3,4-tetrahydro-naphthalene-2-carboxylic acid To a stirred solution of ester from Example 53E (51 mg, 0.15 mmol) and methanol (3 mL) was added 2M NaOH (0.23 mL, 0.46 mmol). The reaction was heated to 70° C. for 48 hours. The reaction cooled to ambient temperature and concentrated under reduced pressure and diluted with water. The pH was adjusted to 3 with 2M HCl and extracted with ethyl acetate. The combined organic layers were dried over Na$_2$SO$_4$, filtered and concentrated to provide the titled compound as a sticky colorless solid (45 mg, 92%). $^1$H NMR (6, DMSO-d$^6$): 12.34 (br s, 1H), 7.08–7.11 (m, 4H), 3.80 (d, 2H), 3.33–3.4 (m, 1H), 2.97–3.1 (m, 2H), 2.69 (t, 2H), 2.41–2.44 (m, 1H), 2.08–2.11 (m, 1H), 1.82–1.87 (m, 1H), 1.02 (t, 3H), 0.90 (d, 6H). MS (DCI/NH$_3$): 320.1 (M+1).

Example 53G (2-(4-Diethylamino-phenylcarbamoyl)-1,2,3,4-tetrahydro-naphthalen-2-yl)-ethyl-carbamic acid isobutyl ester To a stirred solution of acid from Example 53E (45 mg, 0.14 mmol), N,N-diethyl-1,4-phenylenediamine sulfate salt (37 mg, 0.14 mmol), TBTU (55 mg, 0.17 mmol) and N,N-dimethylforamide (1 mL) under N$_2$ was added triethylamine (0.06 mL, 0.42 mmol). The reaction stirred at room temperature for 18 hours. The mixture was poured into aqueous NaHCO$_3$ and extracted with ethyl acetate. The combined organic layers were washed with water and brine, dried over Na$_2$SO$_4$, filtered and concentrated under reduced pressure. The residue was purified by silica gel column (25% ethyl acetate/hexane) to provide the titled compound as a sticky light purple solid (35 mg, 53%). $^1$H NMR (δ, DMSO-d$^6$): 9.26 (s, 1H), 7.47 (d, 2H), 7.19–7.24 (m, 4H), 6.73 (d, 2H), 3.91 (d, 2H), 3.60–3.76 (m, 2H), 3.43 (s, 3 H), 3.41 (d, 2H), 3.03 (d, 1H), 2.77–2.92 (m, 2H), 2.63 (t, 1H), 1.92–2.00 (m, 1H), 1.41 (s, 1H), 1.18 (t, 6H), 1.12 (t, 3H), 1.01 (d, 6H). MS (ESI): 466.2 (M+1).

Example 54

(8-Chloro-2-(4-diethylamino-piperidine-1-carbonyl)-1,2,3,4-tetrahydro-naphthalen-2-yl)-carbamic acid isobutyl ester The titled compound was prepared according to the procedure described in Example 53G, substituting the acid from Example 36A for the acid from Example 53F, and diethyl-piperidin-4-yl-amine for N,N-diethyl-1,4-phenylenediamine sulfate salt used in Example 53G. $^1$H NMR (300 MHz, DMSO-d$^6$): 7.80 (s, 1H), 7.22 (d, J=7.46 Hz, 1H), 7.10 (t, J=7.46 Hz, 1H), 7.04 (d, J=7.46 Hz, 1H), 4.47 (d, J=10.52 Hz, 2H), 3.74–3.63 (m, 2H), 3.00–2.57 (m, 6H), 2.73 (m, 1H), 2.19 (m, 1H), 2.00 (m, 1H), 2.44 (q, J=7.12 Hz, 4H), 1.81 (septet, J=6.79 Hz, 1H), 1.63 (d, J=12.2 Hz, 2H), 1.30–1.10 (m, 2H), 0.95 (t, J=7.12 Hz, 6H), 0.87 (d, J=6.79 Hz, 6H), MS (ESI): 464, 466 (M+H)$^+$.

What is claimed is:
1. A compound according to formula (I),

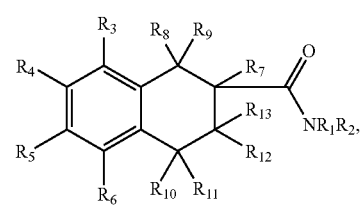

or a therapeutically suitable salt or prodrug thereof, wherein

R$_1$ is selected from the group consisting of hydrogen, alkyl, aryl, arylalkyl, cycloalkyl, cycloalkylalkyl, cycloalkenyl, cycloalkenylalkyl, heterocycle, heterocyclealkyl;

R$_2$ is selected from the group consisting of alkyl, aryl, arylalkyl, cycloalkyl, cycloalkylalkyl, cycloalkenyl, cycloalkenylalkyl, heterocycle, heterocyclealkyl; or R$_1$ and R$_2$ taken together with the nitrogen atom to which they are attached, together form a heterocycle;

$R_3$, $R_4$, $R_5$, and $R_6$ are each independently a member selected from the group consisting of hydrogen, alkoxyalkyl, alkyl, alkenyl, alkenylalkoxy, aryl, cyano, cycloalkyl, halo, haloalkyl, heterocycle, hydroxy, hydroxyalkyl, nitro, sulfonyl, $R_aR_bN$—, $R_aR_b$Nalkyl, $R_aR_b$Ncarboxyalkyl, $R_aR_b$Ncarboxyalkenyl and $R_aR_b$Nsulfonyl;

$R_7$ is a member selected from the group consisting of alkenyl, alkoxy, alkoxycarbonyl, aryl, haloalkyl, cycloalkyl, heterocycle, $R_cR_dN$—, $R_cR_d$Ncarboxy and $R_cR_d$Nsulfonyl;

$R_8$, $R_9$, $R_{10}$, and $R_{11}$ are each independently a member selected from the group consisting of hydrogen, alkoxy, alkoxyalkyl, alkyl, alkenyl, alkenylalkoxy, aryl, cyano, halo, haloalkyl, heterocycle, hydroxy, hydroxyalkyl, $R_aR_bN$—, $R_aR_b$Nalkyl, $R_aR_b$Ncarboxyalkyl;

$R_{12}$ and $R_{13}$ are each independently a member selected from the group consisting of hydrogen, alkoxy, alkoxyalkyl, alkyl, alkenyl, alkenylalkoxy, aryl halo, haloalkyl, heterocycle, hydroxy, hydroxyalkyl, $R_aR_bN$—, $R_aR_b$Nalkyl, $R_aR_b$Ncarboxyalkyl;

$R_a$ and $R_b$ are each independently a member selected from the group consisting of hydrogen, alkenyloxycarbonyl, alkoxyalkyl, alkyl, alkylcarbonyl, alkoxycarbonyl, alkoxycarbonylalkylalkoxyalkoxycarbonyl, alkylsulfonyl, alkynyloxycarbonyl, aryl, arylalkyl, arylalkoxycarbonyl, aryloxyalkyl, aryloxyalkylcarbonyl, cycloalkyl, cycloalkoxycarbonyl, cycloalkylalkyl, cycloalkylalkoxycarbonyl, heterocycle, heterocyclecarbonyl, heterocyclealkyl, heterocyclealkoxylcarbonyl, hydroxyalkoxycarbonyl, haloalkoxycarbonyl, $R_cR_d$Ncarbonyl, $R_cR_d$Ncarbonylalkyl, $R_cR_d$Nalkyl, $R_cR_d$Nalkoxycarbonyl;

$R_c$ and $R_d$ are each independently a member selected from the group consisting of hydrogen, alkenyloxycarbonyl, alkoxyalkyl, alkyl, alkylcarbonyl, alkylNHalkylcarbonyl, alkoxycarbonyl, alkoxycarbonylalkyl,alkoxyalkoxycarbonyl, alkylsulfonyl, alkynyloxycarbonyl, aryl, arylalkyl, arylalkoxycarbonyl, aryloxyalkyl, aryloxyalkylcarbonyl, cycloalkyl, cycloalkoxycarbonyl, cycloalkylalkyl, cycloalkylalkoxycarbonyl, heterocycle, heterocyclecarbonyl, heterocyclealkyl, heterocyclealkoxylcarbonyl, hydroxyalkoxycarbonyl, haloalkoxycarbonyl, nitroalkoxycarbonyl, $R_eR_f$Ncarbonyl, $R_eR_f$Ncarbonylalkyl, $R_eR_f$Nalkyl, $R_eR_f$Nalkoxycarbonyl;

$R_e$ and $R_f$ are each independently a member selected from the group consisting of hydrogen, alkyl.

2. A compound according to formula (Ia),

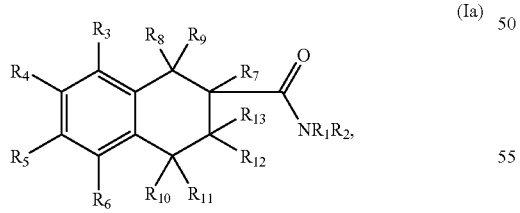

(Ia)

or a therapeutically suitable salt or prodrug thereof, wherein $R_1$ is selected from the group consisting of hydrogen, alkyl, aryl, arylalkyl, heterocycle, and heterocyclealkyl;

$R_2$ is selected from the group consisting of alkyl, aryl, arylalkyl, heterocycle, and heterocyclealkyl; or $R_1$ and $R_2$ taken together with the nitrogen atom to which they are attached, together form a heterocycle;

$R_3$, $R_4$, $R_5$, and $R_6$ are each independently a member selected from the group consisting of hydrogen, alkoxyalkyl, alkyl, alkenyl, alkenylalkoxy, aryl, cyano, cycloalkyl, halo, haloalkyl, heterocycle, hydroxy, hydroxyalkyl, nitro, sulfonyl, $R_aR_bN$—, $R_aR_b$Nalkyl, $R_aR_b$Ncarboxyalkyl, $R_aR_b$Ncarboxyalkenyl, $R_aR_b$Nsulfonyl;

$R_7$ is a member selected from the group consisting of alkenyl, alkoxy, alkoxycarbonyl, aryl, haloalkyl, cycloalkyl, heterocycle, $R_cR_dN$—, $R_cR_d$Ncarboxy and $R_cR_d$Nsulfonyl;

$R_8$, $R_9$, $R_{10}$, and $R_{11}$ are each independently a member selected from the group consisting of hydrogen, alkoxy, alkoxyalkyl, alkyl, alkenyl, alkenylalkoxy, aryl, cyano, halo, haloalkyl, heterocycle, hydroxy, hydroxyalkyl, $R_aR_bN$—, $R_aR_b$Nalkyl, $R_aR_b$Ncarboxyalkyl;

$R_{12}$ and $R_{13}$ are each independently a member selected from the group consisting of hydrogen, alkoxy, alkoxyalkyl, alkyl, alkenyl, alkenylalkoxy, aryl halo, haloalkyl, heterocycle, hydroxy, hydroxyalkyl, $R_aR_bN$—, $R_aR_b$Nalkyl, $R_aR_b$Ncarboxyalkyl;

$R_a$ and $R_b$ are each independently a member selected from the group consisting of hydrogen, alkenyloxycarbonyl, alkoxyalkyl, alkyl, alkylcarbonyl, alkoxycarbonyl, alkoxycarbonylalkylalkoxyalkoxycarbonyl, alkylsulfonyl, alkynyloxycarbonyl, aryl, arylalkyl, arylalkoxycarbonyl, aryloxyalkyl, aryloxyalkylcarbonyl, cycloalkyl, cycloalkoxycarbonyl, cycloalkylalkyl, cycloalkylalkoxycarbonyl, heterocycle, heterocyclecarbonyl, heterocyclealkyl, heterocyclealkoxylcarbonyl, hydroxyalkoxycarbonyl, haloalkoxycarbonyl, $R_cR_d$Ncarbonyl, $R_cR_d$Ncarbonylalkyl, $R_cR_d$Nalkyl, $R_cR_d$Nalkoxycarbonyl;

$R_c$ and $R_d$ are each independently a member selected from the group consisting of hydrogen, alkenyloxycarbonyl, alkoxyalkyl, alkyl, alkylcarbonyl, alkylNHalkylcarbonyl, alkoxycarbonyl, alkoxycarbonylalkyl,alkoxyalkoxycarbonyl, alkylsulfonyl, alkynyloxycarbonyl, aryl, arylalkyl, arylalkoxycarbonyl, aryloxyalkyl, aryloxyalkylcarbonyl, cycloalkyl, cycloalkoxycarbonyl, cycloalkylalkyl, cycloalkylalkoxycarbonyl, heterocycle, heterocyclecarbonyl, heterocyclealkyl, heterocyclealkoxylcarbonyl, hydroxyalkoxycarbonyl, haloalkoxycarbonyl, nitroalkoxycarbonyl, $R_eR_f$Ncarbonyl, $R_eR_f$Ncarbonylalkyl, $R_eR_f$Nalkyl, $R_eR_f$Nalkoxycarbonyl;

$R_e$ and $R_f$ are each independently a member selected from the group consisting of hydrogen, alkyl.

3. A compound according to formula (II),

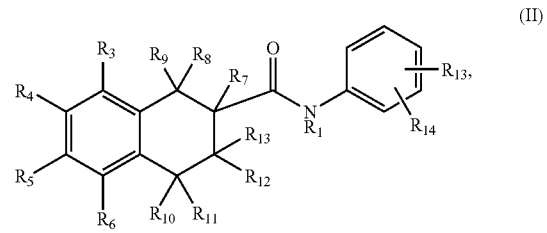

(II)

or a therapeutically suitable salt or prodrug thereof, wherein $R_1$ is selected from the group consisting of hydrogen, alkyl, aryl, arylalkyl, heterocycle, and heterocyclealkyl;

$R_3$, $R_4$, $R_5$, and $R_6$ are each independently a member selected from the group consisting of hydrogen, alkoxyalkyl, alkyl, alkenyl, alkenylalkoxy, aryl, cyano, cycloalkyl, halo, haloalkyl, heterocycle, hydroxy, hydroxyalkyl, nitro, sulfonyl, $R_aR_bN-$, $R_aR_bN$alkyl, $R_aR_b$Ncarboxyalkyl, $R_aR_b$Ncarboxyalkenyl, $R_aR_b$Nsulfonyl;

$R_7$ is a member selected from the group consisting of alkenyl, alkoxy, alkoxycarbonyl, aryl, haloalkyl, cycloalkyl, heterocycle, $R_cR_dN-$, $R_cR_d$Ncarboxy and $R_cR_d$Nsulfonyl;

$R_8$, $R_9$, $R_{10}$, and $R_{11}$ are each independently a member selected from the group consisting of hydrogen, alkoxy, alkoxyalkyl, alkyl, alkenyl, alkenylalkoxy, aryl, cyano, halo, haloalkyl, heterocycle, hydroxy, hydroxyalkyl, $R_aR_bN-$, $R_aR_b$Nalkyl, $R_aR_b$Ncarboxyalkyl;

$R_{12}$ and $R_{13}$ are each independently a member selected from the group consisting of hydrogen, alkoxy, alkoxyalkyl, alkyl, alkenyl, alkenylalkoxy, aryl halo, haloalkyl, heterocycle, hydroxy, hydroxyalkyl, $R_aR_bN-$, $R_aR_b$Nalkyl, $R_aR_b$Ncarboxyalkyl;

$R_{14}$ is alkyl;

$R_a$ and $R_b$ are each independently a member selected from the group consisting of hydrogen, alkenyloxycarbonyl, alkoxyalkyl, alkyl, alkylcarbonyl, alkoxycarbonyl, alkoxycarbonylalkylalkoxyalkoxycarbonyl, alkylsulfonyl, alkynyloxycarbonyl, aryl, arylalkyl, arylalkoxycarbonyl, aryloxyalkyl, aryloxyalkylcarbonyl, cycloalkyl, cycloalkoxycarbonyl, cycloalkylalkyl, cycloalkylalkoxycarbonyl, heterocycle, heterocyclecarbonyl, heterocyclealkyl, heterocyclealkoxylcarbonyl, hydroxyalkoxycarbonyl, haloalkoxycarbonyl, $R_cR_d$Ncarbonyl, $R_cR_d$Ncarbonylalkyl, $R_cR_d$Nalkyl, $R_cR_d$Nalkoxycarbonyl;

$R_c$ and $R_d$ are each independently a member selected from the group consisting of hydrogen, alkenyloxycarbonyl, alkoxyalkyl, alkyl, alkylcarbonyl, alkylNHalkylcarbonyl, alkoxycarbonyl, alkoxycarbonylalkyl,alkoxyalkoxycarbonyl, alkylsulfonyl, alkynyloxycarbonyl, aryl, arylalkyl, arylalkoxycarbonyl, aryloxyalkyl, aryloxyalkylcarbonyl, cycloalkyl, cycloalkoxycarbonyl, cycloalkylalkyl, cycloalkylalkoxycarbonyl, heterocycle, heterocyclecarbonyl, heterocyclealkyl, heterocyclealkoxylcarbonyl, hydroxyalkoxycarbonyl, haloalkoxycarbonyl, nitroalkoxycarbonyl, $R_eR_f$Ncarbonyl, $R_eR_f$Ncarbonylalkyl, $R_eR_f$Nalkyl, $R_eR_f$Nalkoxycarbonyl;

$R_e$ and $R_f$ are each independently a member selected from the group consisting of hydrogen, alkyl.

4. A compound according to formula (IIb),

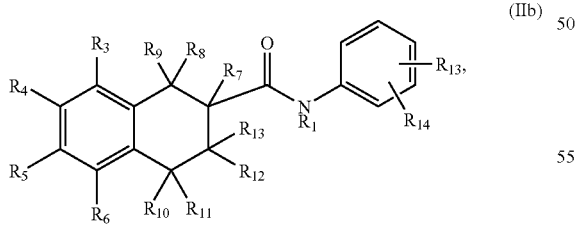

(IIb)

or a therapeutically suitable salt or prodrug thereof, wherein $R_1$ is selected from the group consisting of hydrogen, alkyl, aryl, arylalkyl, heterocycle, and heterocyclealkyl;

$R_3$, $R_4$, $R_5$, and $R_6$ are each independently a member selected from the group consisting of hydrogen, alkoxyalkyl, alkyl, alkenyl, alkenylalkoxy, aryl, cyano, halo, haloalkyl, heterocycle, hydroxy, hydroxyalkyl, nitro, sulfonyl, $R_aR_bN-$, $R_aR_b$Nalkyl, $R_aR_b$Ncarboxyalkyl;

$R_7$ is a member selected from the group consisting of alkenyl, alkyl, alkoxy, aryl, haloalkyl, cycloalkyl, heterocycle and $R_cR_dN-$;

$R_8$, $R_9$, $R_{10}$, and $R_{11}$ are each independently a member selected from the group consisting of hydrogen, alkoxy, alkoxyalkyl, alkyl, alkenyl, alkenylalkoxy, aryl, cyano, halo, haloalkyl, heterocycle, hydroxy, hydroxyalkyl, $R_aR_bN-$, $R_aR_b$Nalkyl, $R_aR_b$Ncarboxyalkyl;

$R_{12}$ and $R_{13}$ are each independently a member selected from the group consisting of hydrogen, alkoxy, alkoxyalkyl, alkyl, alkenyl, alkenylalkoxy, aryl halo, haloalkyl, heterocycle, hydroxy, hydroxyalkyl, $R_aR_bN-$, $R_aR_b$Nalkyl, $R_aR_b$Ncarboxyalkyl;

$R_{14}$ is alkyl;

$R_a$ and $R_b$ are each independently a member selected from the group consisting of hydrogen, alkenyloxycarbonyl, alkoxyalkyl, alkyl, alkylcarbonyl, alkoxycarbonyl, alkoxycarbonylalkylalkoxyalkoxycarbonyl, alkylsulfonyl, alkynyloxycarbonyl, aryl, arylalkyl, arylalkoxycarbonyl, aryloxyalkyl, aryloxyalkylcarbonyl, cycloalkyl, cycloalkoxycarbonyl, cycloalkylalkyl, cycloalkylalkoxycarbonyl, heterocycle, heterocyclecarbonyl, heterocyclealkyl, heterocyclealkoxylcarbonyl, hydroxyalkoxycarbonyl, haloalkoxycarbonyl, $R_cR_d$Ncarbonyl, $R_cR_d$Ncarbonylalkyl, $R_cR_d$Nalkyl, $R_cR_d$Nalkoxycarbonyl;

$R_c$ and $R_d$ are each independently a member selected from the group consisting of hydrogen, alkenyloxycarbonyl, alkoxyalkyl, alkyl, alkylcarbonyl, alkylNHalkylcarbonyl, alkoxycarbonyl, alkoxycarbonylalkyl,alkoxyalkoxycarbonyl, alkylsulfonyl, alkynyloxycarbonyl, aryl, arylalkyl, arylalkoxycarbonyl, aryloxyalkyl, aryloxyalkylcarbonyl, cycloalkyl, cycloalkoxycarbonyl, cycloalkylalkyl, cycloalkylalkoxycarbonyl, heterocycle, heterocyclecarbonyl, heterocyclealkyl, heterocyclealkoxylcarbonyl, hydroxyalkoxycarbonyl, haloalkoxycarbonyl, nitroalkoxycarbonyl, $R_eR_f$Ncarbonyl, $R_eR_f$Ncarbonylalkyl, $R_eR_f$Nalkyl, $R_eR_f$Nalkoxycarbonyl;

$R_e$ and $R_f$ are each independently a member selected from the group consisting of hydrogen, alkyl.

5. The compounds according to claim 4, that is a member selected from the group consisting of N-(4-(diethylamino)phenyl)-8-methoxy-2-methyl-1,2,3,4-tetrahydronaphthalene-2-carboxamide;

tert-butyl 2-(((4-(diethylamino)phenyl)amino)carbonyl)-1,2,3,4-tetrahydronaphthalen-2-ylcarbamate;

tert-butyl 2-(((4-(diethylamino)-2-methylphenyl)amino)carbonyl)-1,2,3,4-tetrahydronaphthalen-2-ylcarbamate;

ethyl 2-(((4-(diethylamino)phenyl)amino)carbonyl)-1,2,3,4-tetrahydronaphthalen-2-ylcarbamate;

isobutyl 2-(((4-(diethylamino)phenyl)amino)carbonyl)-1,2,3,4-tetrahydronaphthalen-2-ylcarbamate;

benzyl 2-(((4-(diethylamino)phenyl)amino)carbonyl)-1,2,3,4-tetrahydronaphthalen-2-ylcarbamate;

tert-butyl 2-(((4-(diethylamino)phenyl)amino)carbonyl)-1,2,3,4-tetrahydronaphthalen-2-yl(methyl)carbamate;

methyl 2-(((4-(diethylamino)-2-methylphenyl)amino)carbonyl)-8-methoxy-1,2,3,4-tetrahydronaphthalene-2-carboxylate;

N-(4-(diethylamino)phenyl)-2-((N-isopropylglycyl)amino)-1,2,3,4-tetrahydronaphthalene-2-carboxamide;

tert-butyl 8-bromo-2-(((4-(diethylamino)phenyl)amino)carbonyl)-1,2,3,4-tetrahydronaphthalen-2-ylcarbamate;

isobutyl 2-(((4-(diethylamino)phenyl)amino)carbonyl)-1,2,3,4-tetrahydronaphthalen-2-yl(methyl)carbamate;
2-fluoroethyl 2-(((4-(diethylamino)phenyl)amino)carbonyl)-1,2,3,4-tetrahydronaphthalen-2-ylcarbamate;
neopentyl 2-(((4-(diethylamino)phenyl)amino)carbonyl)-1,2,3,4-tetrahydronaphthalen-2-ylcarbamate;
3-chloropropyl 2-(((4-(diethylamino)phenyl)amino)carbonyl)-1,2,3,4-tetrahydronaphthalen-2-ylcarbamate;
but-3-enyl 2-(((4-(diethylamino)phenyl)amino)carbonyl)-1,2,3,4-tetrahydronaphthalen-2-ylcarbamate;
hexyl 2-(((4-(diethylamino)phenyl)amino)carbonyl)-1,2,3,4-tetrahydronaphthalen-2-ylcarbamate;
but-3-ynyl 2-(((4-(diethylamino)phenyl)amino)carbonyl)-1,2,3,4-tetrahydronaphthalen-2-ylcarbamate;
allyl 2-(((4-(diethylamino)phenyl)amino)carbonyl)-1,2,3,4-tetrahydronaphthalen-2-ylcarbamate;
butyl 2-(((4-(diethylamino)phenyl)amino)carbonyl)-1,2,3,4-tetrahydronaphthalen-2-ylcarbamate;
propyl 2-(((4-(diethylamino)phenyl)amino)carbonyl)-1,2,3,4-tetrahydronaphthalen-2-ylcarbamate;
but-2-ynyl 2-(((4-(diethylamino)phenyl)amino)carbonyl)-1,2,3,4-tetrahydronaphthalen-2-ylcarbamate;
pentyl 2-(((4-(diethylamino)phenyl)amino)carbonyl)-1,2,3,4-tetrahydronaphthalen-2-ylcarbamate;
isobutyl 2-(((4-(diethylamino)phenyl)amino)carbonyl)-8-methoxy-1,2,3,4-tetrahydronaphthalen-2-ylcarbamate;
isobutyl 2-(((4-(diethylamino)-2-methylphenyl)amino)carbonyl)-8-methoxy-1,2,3,4-tetrahydronaphthalen-2-ylcarbamate;
isobutyl 2-(((4-(diethylamino)phenyl)amino)carbonyl)-8-methoxy-1,2,3,4-tetrahydronaphthalen-2-yl(methyl)carbamate;
isobutyl 2-(((4-(diethylamino)-2-methylphenyl)amino)carbonyl)-8-methoxy-1,2,3,4-tetrahydronaphthalen-2-yl(methyl)carbamate;
isobutyl 8-bromo-2-(((4-(diethylamino)phenyl)amino)carbonyl)-1,2,3,4-tetrahydronaphthalen-2-ylcarbamate;
isobutyl(2R)-8-chloro-2-(((4-(diethylamino)phenyl)amino)carbonyl)-1,2,3,4-tetrahydronaphthalen-2-ylcarbamate;
neopentyl(2R)-8-chloro-2-(((4-(diethylamino)phenyl)amino)carbonyl)-1,2,3,4-tetrahydronaphthalen-2-ylcarbamate;
neopentyl(2R)-8-chloro-2-(((4-(diethylamino)-2-methylphenyl)amino)carbonyl)-1,2,3,4-tetrahydronaphthalen-2-ylcarbamate;
isobutyl(2R)-8-chloro-2-(((4-(diethylamino)phenyl)amino)carbonyl)-1,2,3,4-tetrahydronaphthalen-2-yl(methyl)carbamate;
isobutyl(2S)-2-(((4-(dibutylamino)phenyl)amino)carbonyl)-1,2,3,4-tetrahydronaphthalen-2-ylcarbamate;
isobutyl(2S)-2-(((4-(2,4-diamino-6-ethylpyrimidin-5-yl)phenyl)amino)carbonyl)-1,2,3,4-tetrahydronaphthalen-2-ylcarbamate;
isobutyl(2S)-6-bromo-2-(((4-(diethylamino)phenyl)amino)carbonyl)-1,2,3,4-tetrahydronaphthalen-2-ylcarbamate;
2-methyl-2-nitropropyl(2R)-2-(((4-(diethylamino)phenyl)amino)carbonyl)-1,2,3,4-tetrahydronaphthalen-2-ylcarbamate;
isobutyl(2S)-6-((1E)-3-amino-3-oxoprop-1-enyl)-2-(((4-(diethylamino)phenyl)amino)carbonyl)-1,2,3,4-tetrahydronaphthalen-2-ylcarbamate;
isobutyl(2S)-2-(((4-(diethylamino)phenyl)amino)carbonyl)-6-methoxy-1,2,3,4-tetrahydronaphthalen-2-ylcarbamate;
2-(dimethylamino)-2-methylpropyl(2R)-2-(((4-(diethylamino)phenyl)amino)carbonyl)-1,2,3,4-tetrahydronaphthalen-2-ylcarbamate;
(2S)-tetrahydrofuran-2-ylmethyl(2S)-2-(((4-(diethylamino)phenyl)amino)carbonyl)-1,2,3,4-tetrahydronaphthalen-2-ylcarbamate;
pyridin-3-ylmethyl(2S)-2-(((4-(diethylamino)phenyl)amino)carbonyl)-1,2,3,4-tetrahydronaphthalen-2-ylcarbamate;
isopropyl(2S)-2-(((4-(diethylamino)phenyl)amino)carbonyl)-1,2,3,4-tetrahydronaphthalen-2-ylcarbamate;
2-chloroethyl(2S)-2-(((4-(diethylamino)phenyl)amino)carbonyl)-1,2,3,4-tetrahydronaphthalen-2-ylcarbamate;
2-bromoethyl(2S)-2-(((4-(diethylamino)phenyl)amino)carbonyl)-1,2,3,4-tetrahydronaphthalen-2-ylcarbamate;
2-methoxyethyl(2S)-2-(((4-(diethylamino)phenyl)amino)carbonyl)-1,2,3,4-tetrahydronaphthalen-2-ylcarbamate; and
isobutyl(2R)-2-(((4-(diethylamino)phenyl)amino)carbonyl)-1,2,3,4-tetrahydronaphthalen-2-yl(ethyl)carbamate.

6. A compound according to formula (IIc),

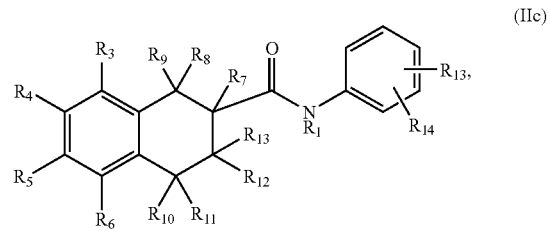

or a therapeutically suitable salt or prodrug thereof, wherein $R_1$ is selected from the group consisting of hydrogen, alkyl, aryl, arylalkyl, heterocycle, and heterocyclealkyl;

$R_3$, $R_4$, $R_5$, and $R_6$ are each independently a member selected from the group consisting of hydrogen, alkoxy, alkoxyalkyl, alkyl, alkenyl, alkenylalkoxy, aryl, cyano, halo, haloalkyl, heterocycle, hydroxy, hydroxyalkyl, nitro, sulfonyl, $R_aR_bN$—, $R_aR_b$Nalkyl, $R_aR_b$Ncarboxyalkyl;

$R_7$ is a member selected from the group consisting of alkoxycarbonyl, $R_cR_d$Ncarboxy and $R_cR_d$Nsulfonyl;

$R_{14}$ is alkyl;

$R_8$, $R_9$, $R_{10}$, $R_{11}$, are each independently a member selected from the group consisting of hydrogen, alkoxy, alkoxyalkyl, alkyl, alkenyl, alkenylalkoxy, aryl, cyano, halo, haloalkyl, heterocycle, hydroxy, hydroxyalkyl, $R_aR_bN$—, $R_aR_b$Nalkyl, $R_aR_b$Ncarboxyalkyl;

$R_{12}$ and $R_{13}$ are each independently a member selected from the group consisting of hydrogen, alkoxy, alkoxyalkyl, alkyl, alkenyl, alkenylalkoxy, aryl halo, haloalkyl, heterocycle, hydroxy, hydroxyalkyl, $R_aR_bN$—, $R_aR_b$Nalkyl, $R_aR_b$Ncarboxyalkyl;

$R_a$ and $R_b$ are each independently a member selected from the group consisting of hydrogen, alkenyloxycarbonyl, alkoxyalkyl, alkyl, alkylcarbonyl, alkoxycarbonyl, alkoxycarbonylalkylalkoxyalkoxycarbonyl, alkylsulfonyl, alkynyloxycarbonyl, aryl, arylalkyl, arylalkoxycarbonyl, aryloxyalkyl, aryloxyalkylcarbonyl, cycloalkyl, cycloalkoxycarbonyl, cycloalkylalkyl, cycloalkylalkoxycarbonyl, heterocycle, heterocyclecarbonyl, heterocyclealkyl, heterocyclealkoxylcarbonyl, hydroxyalkoxycarbonyl, haloalkoxycarbonyl, $R_cR_d$Ncarbonyl, $R_cR_d$Ncarbonylalkyl, $R_cR_d$Nalkyl, $R_cR_d$Nalkoxycarbonyl;

$R_c$ and $R_d$ are each independently a member selected from the group consisting of hydrogen, alkenyloxycarbonyl, alkoxyalkyl, alkyl, alkylcarbonyl, alkylNHalkylcarbonyl, alkoxycarbonyl, alkoxycarbonylalkyl, alkoxyalkoxycarbonyl, alkylsulfonyl, alkynyloxycarbonyl, aryl, arylalkyl, arylalkoxycarbonyl, aryloxyalkyl, aryloxyalkylcarbonyl, cycloalkyl, cycloalkoxycarbonyl, cycloalkylalkyl, cycloalkylalkoxycarbonyl, heterocycle, heterocyclecarbonyl, heterocyclealkyl, heterocyclealkoxylcarbonyl, hydroxyalkoxycarbonyl, haloalkoxycarbonyl, nitroalkoxycarbonyl, $R_e R_f$Ncarbonyl, $R_e R_f$Ncarbonylalkyl, $R_e R_f$Nalkyl, $R_e R_f$Nalkoxycarbonyl;

$R_e$ and $R_f$ are each independently a member selected from the group consisting of hydrogen, alkyl.

7. The compounds according to claim 6, that is a member selected from the group consisting of isobutyl 2-(((4-(diethylamino)phenyl)amino)carbonyl)-1,2,3,4-tetrahydronaphthalene-2-carboxylate;

3-methylbutyl 2-(((4-(diethylamino)phenyl)amino)carbonyl)-1,2,3,4-tetrahydronaphthalene-2-carboxylate;

methyl N-((2-(((4-(diethylamino)phenyl)amino)carbonyl)-1,2,3,4-tetrahydronaphthalen-2-yl)carbonyl)valinate; and $N^2$-(4-(diethylamino)phenyl)-($N^1,N^1$-dimethylglycinamide)-3,4-dihydronaphthalene-2,2(1H)-dicarboxamide.

8. A method of treating anorexia, comprising administration of a compound of formula (I) of claim 1.

9. A method of treating anorexia, comprising administration of a compound of formula (II) of claim 3.

10. A method of treating cancer cachexia, comprising administration of a compound of formula (I) of claim 1.

11. A method of treating cancer cachexia, comprising administration of a compound of formula (II) of claim 3.

12. A method of treating eating disorders, comprising administration of a compound of formula (I) of claim 1.

13. A method of treating eating disorders, comprising administration of a compound of formula (II) of claim 3.

14. A method of treating weight gain, comprising administration of a compound of formula (I) of claim 1.

15. A method of treating weight gain, comprising administration of a compound of formula (II) of claim 3.

16. A method of treating obesity, comprising administration of a compound of formula (I) of claim 1.

17. A method of treating obesity, comprising administration of a compound of formula (II) of claim 3.

18. A method of treating diabetes mellitus, comprising administration of a compound of formula (I) of claim 1.

19. A method of treating diabetes mellitus, comprising administration of a compound of formula (II) of claim 3.

20. A pharmaceutical composition comprising a therapeutically effective amount of a compound of formula (I) of claim 1 in combination with a pharmaceutically suitable carrier.

21. A pharmaceutical composition comprising a therapeutically effective amount of a compound of formula (II) of claim 3 in combination with a pharmaceutically suitable carrier.

\* \* \* \* \*